(12) United States Patent
Yamato et al.

(10) Patent No.: US 9,005,871 B2
(45) Date of Patent: Apr. 14, 2015

(54) SULFONIUM DERIVATIVES AND THE USE THEROF AS LATENT ACIDS

(75) Inventors: Hitoshi Yamato, Takarazuka (JP); Toshikage Asakura, Minoo (JP); Yuichi Nishimae, Osaka (JP)

(73) Assignee: BASF SE, Ludwigshafen (DE)

( * ) Notice: Subject to any disclaimer, the term of this patent is extended or adjusted under 35 U.S.C. 154(b) by 449 days.

(21) Appl. No.: 13/123,723

(22) PCT Filed: Oct. 8, 2009

(86) PCT No.: PCT/EP2009/063095
§ 371 (c)(1),
(2), (4) Date: Aug. 11, 2011

(87) PCT Pub. No.: WO2010/046240
PCT Pub. Date: Apr. 29, 2010

(65) Prior Publication Data
US 2011/0300484 A1  Dec. 8, 2011

(30) Foreign Application Priority Data
Oct. 20, 2008 (EP) ..................... 08167016

(51) Int. Cl.
*G03F 7/004* (2006.01)
*G03F 7/038* (2006.01)
*G03F 7/039* (2006.01)
*G03F 7/20* (2006.01)
*G03F 7/30* (2006.01)
*C07C 317/04* (2006.01)
*C07C 381/12* (2006.01)
*G03F 7/00* (2006.01)

(52) U.S. Cl.
CPC ............. *C07C 381/12* (2013.01); *C07C 317/04* (2013.01); *G03F 7/0007* (2013.01); *G03F 7/0045* (2013.01); *G03F 7/0046* (2013.01); *G03F 7/038* (2013.01); *G03F 7/0382* (2013.01); *G03F 7/0392* (2013.01); *Y10S 430/122* (2013.01); *Y10S 430/123* (2013.01); *Y10S 430/124* (2013.01); *Y10S 430/125* (2013.01); *Y10S 430/126* (2013.01)

(58) Field of Classification Search
None
See application file for complete search history.

(56) References Cited

U.S. PATENT DOCUMENTS

| 5,021,197 A | 6/1991 | Takeda et al. |
| 5,554,664 A | 9/1996 | Lamanna et al. |
| 6,368,769 B1 | 4/2002 | Ohkawa et al. |
| 6,613,486 B1 * | 9/2003 | Shimizu et al. ............ 430/7 |
| 7,829,257 B2 | 11/2010 | Oka et al. |
| 7,901,867 B2 | 3/2011 | Wolf et al. |
| 2003/0235782 A1 | 12/2003 | Padmanaban et al. |
| 2006/0055088 A1 | 3/2006 | Nakayashiki et al. |
| 2007/0190454 A1 | 8/2007 | Lee et al. |
| 2010/0297540 A1 | 11/2010 | Hayoz |
| 2010/0297541 A1 | 11/2010 | Hayoz |
| 2010/0297542 A1 | 11/2010 | Hayoz |

FOREIGN PATENT DOCUMENTS

| CN | 101236356 A | 8/2008 |
| EP | 0346756 A | 12/1989 |
| JP | 09-043844 | 2/1997 |
| JP | 09-269409 | 10/1997 |
| JP | 2001-235858 | 8/2001 |
| JP | 2004137172 | 5/2004 |
| JP | 2005263796 | 9/2005 |
| JP | 2007112728 | 5/2007 |
| WO | 03008404 | 1/2003 |
| WO | 03072567 | 9/2003 |
| WO | 03/107093 A | 12/2003 |
| WO | 2007118794 A1 | 10/2007 |
| WO | WO-2009/047105 A1 * | 4/2009 |
| WO | WO 2009/047152 A1 * | 4/2009 |

OTHER PUBLICATIONS

Copending U.S. Appl. No. 13/123,723, filed Apr. 12, 2011.
Copending U.S. Appl. No. 12/996,795, filed Dec. 8, 2010.
English language machine-generated translation of JP 09-269409 (13 Pages); 1997.
English language machine-generated translation of JP 09-043844 (6 Pages); 1997.
English language machine translation of JP2004137172 (2004).
English language machine translation of JP2005263796 (2005).
English language machine translation of JP2007112728 (2007).

\* cited by examiner

*Primary Examiner* — Sin J. Lee
(74) *Attorney, Agent, or Firm* — Shruti Costales

(57) ABSTRACT

Compounds of the formula (I), wherein $Ar_1$ is for example phenylene or biphenylene both unsubstituted or substituted; $Ar_2$ and $Ar_3$ are for example independently of each other phenyl, naphthyl, biphenylylyl or heteroaryl, all optionally substituted; or $Ar_1$ and $Ar_2$ for example together with a direct bond, O, S or (CO), form a fused ring system; R is for example hydrogen, $C_3$-$C_{30}$cycloalkyl or $C_1$-$C_{18}$alkyl; and $R_1$, $R_2$ and $R_3$ independently of each other are for example $C_1$-$C_{10}$haloalkyl; are effective photoacid generators (PAG).

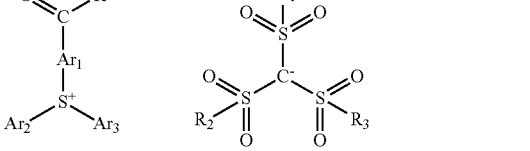

(I)

18 Claims, No Drawings

SULFONIUM DERIVATIVES AND THE USE THEROF AS LATENT ACIDS

The invention relates to new sulfonium salts, chemically amplified photoresist compositions comprising said compounds and to the use of the compounds as latent acids, which can be activated by irradiation with actinic electromagnetic radiation and electron beams.

Sulphonium salts are known in the art as photoinitiators. In U.S. Pat. No. 6,368,769 and JP2004-137172A phenylthiophenyl-diphenylsulfonium salts comprising acyl group are disclosed. WO03/072567 and WO03/008404 disclose sulphonium salts, wherein the sulphonium ion is located in a condensed ring system, for example in the thioxanthyl moiety. Other compounds of this type such as dibenzothiophenyl-diarylsulfonium salts comprising acyl group are disclosed in US2006/055088. In JP2005-263796A 5-aryl-dibenzothiophenium salts comprising acyl group are described. JP2007-112728A disclosed triarylsulfonium salts comprising acyl group. All of the sulfonium salts described above have $SbF_6^-$, $PF_6^-$, $AsF_6^-$, $BF_4^-$, $SbCl_6^-$, $ClO_4^-$, arylsulfonate, alkylsulfonate or tetraarylborate as the counter anion. U.S. Pat. No. 5,554,664 disclosed sulfonium salts having trifluoroalkylsulfonylmethide as the counter anion.

In the art exists a need for reactive latent acid donors that are thermally and chemically stable and that, after being activated by light, UV-radiation, X-ray irradiation or electron beams can be used as catalysts for a variety of acid-catalysed reactions, such as polycondensation reactions, acid-catalysed depolymerisation reactions, acid-catalysed electrophilic substitution reactions or the acid-catalysed removal of protecting groups. A particular need exists for latent acid catalysts with high stability, high sensitivity and high resolution not only in the Deep-UV range but also in a wide range of wavelengths such as for example g-line (436 nm), i-line (365 nm), KrF (248 nm), ArF (193 nm) and EUV (13.5 nm; extreme-ultraviolet).

Surprisingly, it has now been found that specific sulfonium salts, as described below, are stable and highly active against the wide range of light sources. The sulfonium salts in the present invention are suitable as catalysts for the aforementioned acid catalyzed reactions in chemically amplified photoresist applications. In addition, the sulfonium salts in the present invention are particularly suitable for i-line and broadband lithography due to their ideal UV absorption profile for such application, resulting in high sensitivity without sensitizer. Furthermore, chemically amplified photoresist compositions comprising sulfonium salts of the present invention provide a high resolution.

Subject of the invention is a compound of the formula I

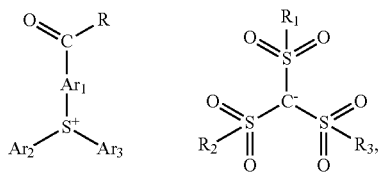

wherein $Ar_1$ is phenylene, biphenylene, naphthylene,

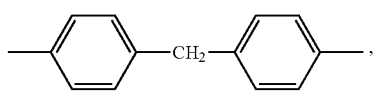

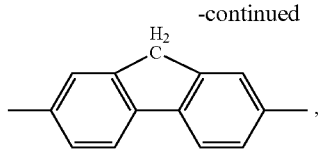

heteroarylene, oxydiphenylene or

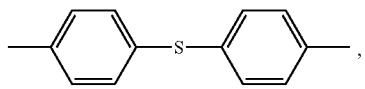

wherein the phenylene, biphenylene, naphthylene,

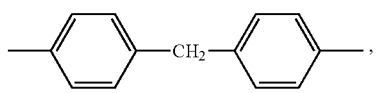

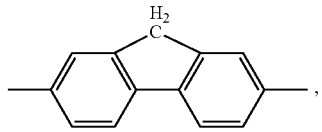

heteroarylene, oxydiphenylene or

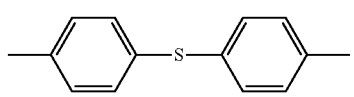

are unsubstituted or are substituted by one or more $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or are substituted by $C_2$-$C_{18}$alkyl which is interrupted by one or more O, S, $NR_7$, O(CO), (CO)O, (CO)$NR_7$ or $NR_7$(CO), or are substituted by $C_3$-$C_{30}$cycloalkyl which is interrupted by one or more O, S, $NR_7$, O(CO), (CO)O, (CO)$NR_7$ or $NR_7$(CO), or are substituted by $C_4$-$C_{30}$cycloalkenyl which is interrupted by one or more O, S, $NR_7$, O(CO), (CO)O, (CO)$NR_7$ or $NR_7$(CO), or are substituted by one or more halogen, $NO_2$, CN, Ar, (CO)$R_8$, (CO)$OR_4$, (CO)$NR_5R_6$, O(CO)$R_8$, O(CO)$OR_4$, O(CO)$NR_5R_6$, $NR_7$(CO)$R_8$, $NR_7$(CO)$OR_4$, $OR_4$, $NR_5R_6$, $SR_7$, $SOR_8$, $SO_2R_8$ or —$OSO_2R_8$, wherein optionally the substituents $C_1$-$C_{18}$alkyl, $C_2$-$C_{12}$alkenyl, (CO)$R_8$, (CO)$OR_4$, (CO)$NR_5R_6$, O(CO)$R_8$, O(CO)$OR_4$, O(CO)$NR_5R_6$, $NR_7$(CO)$R_8$, $NR_7$(CO)$OR_4$, $OR_4$, $NR_5R_6$, $SR_7$, $SOR_8$, $SO_2R_8$ or $OSO_2R_8$ form 5-, 6- or 7-membered rings, via the radicals $C_1$-$C_{18}$alkyl, $C_2$-$C_{12}$alkenyl, $R_4$, $R_5$, $R_6$, $R_7$ and/or $R_8$, with further substituents on the phenylene, biphenylene, naphthylene, -continued

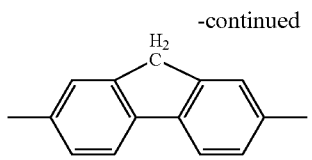

heteroarylene, oxydiphenylene or

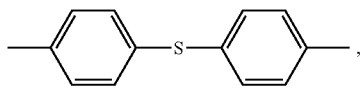

or with one of the carbon atoms of the phenylene, biphenylene, naphthylene,

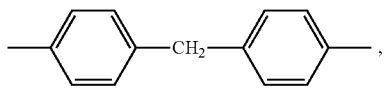

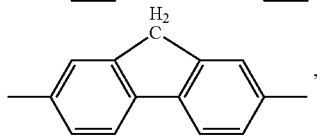

heteroarylene, oxydiphenylene or

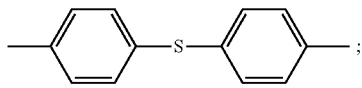

wherein all $Ar_1$ optionally additionally are substituted by a group having a —O—C-bond or a —O—Si-bond which cleaves upon the action of an acid;

$Ar_2$ and $Ar_3$ independently of each other are phenyl, naphthyl, biphenylyl or heteroaryl, wherein the phenyl, naphthyl, biphenylyl or heteroaryl are unsubstituted or are substituted by one or more $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or by $C_2$-$C_{18}$alkyl which is interrupted by one or more O, S, $NR_7$, O(CO), (CO)O, (CO)$NR_7$ or $NR_7$(CO), or by $C_3$-$C_{30}$cycloalkyl which is interrupted by one or more O, S, $NR_7$, O(CO), (CO)O, (CO)$NR_7$ or $NR_7$(CO), or by $C_4$-$C_{30}$cycloalkenyl which is interrupted by one or more O, S, $NR_7$, O(CO), (CO)O, (CO)$NR_7$ or $NR_7$(CO), or are substituted by one or more halogen, $NO_2$, CN, Ar, O(CO)$R_8$, O(CO)$OR_4$, O(CO)$NR_5R_6$, $NR_7$(CO)$R_8$, $NR_7$(CO)$OR_4$, $OR_4$, $NR_5R_6$, $SR_7$, $SOR_8$, $SO_2R_8$ or $OSO_2R_8$, optionally the substituents $C_1$-$C_{18}$alkyl, $C_2$-$C_{12}$alkenyl, O(CO)$R_8$, O(CO)$OR_4$, O(CO)$NR_5R_6$, $NR_7$(CO)$R_8$, $NR_7$(CO)$OR_4$, $OR_4$, $NR_5R_6$, $SR_7$, $SOR_8$, $SO_2R_8$ or $OSO_2R_8$ form 5-, 6- or 7-membered rings, via the radicals $C_1$-$C_{18}$alkyl, $C_2$-$C_{12}$alkenyl, $R_4$, $R_5$, $R_6$, $R_7$ and/or $R_8$, with further substituents on the phenyl, naphthyl, biphenylyl or heteroaryl or with one of the carbon atoms of the phenyl, naphthyl, biphenylyl or heteroaryl;

or $Ar_1$ and $Ar_2$ together with a direct bond, O, S, $NR_7$ or (CO), form a fused ring system;

or $Ar_1$ and $Ar_2$ together with $C_1$-$C_2$alkylene, O, S, $NR_7$ or (CO), form a 5-, 6-, or 7-membered ring;

or $Ar_2$ and $Ar_3$ together with a direct bond, O, S, $NR_7$ or (CO) form a fused ring system;

or $Ar_2$ and $Ar_3$ together with $C_1$-$C_2$alkylene, O, S, $NR_7$ or (CO), form a 5-, 6-, or 7-membered ring;

or $A_1$ and $Ar_2$ together with the

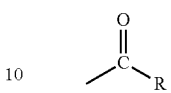

which is attached to the $Ar_1$, form

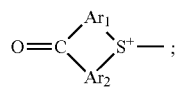

wherein all $Ar_2$ and $Ar_3$ optionally additionally are substituted by a group having a —O—C-bond or a —O—Si-bond which cleaves upon the action of an acid;

R is hydrogen, $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or is $C_2$-$C_{18}$alkyl which is interrupted by one or more O, S, $NR_7$, O(CO), (CO)O, (CO)$NR_7$ or $NR_7$(CO), or is $C_3$-$C_{30}$cycloalkyl which is interrupted by one or more O, S, $NR_7$, O(CO), (CO)O, (CO)$NR_7$ or $NR_7$(CO), or is $C_4$-$C_{30}$cycloalkenyl which is interrupted by one or more O, S, $NR_7$, O(CO), (CO)O, (CO)$NR_7$ or $NR_7$(CO), or R is Ar, $OR_4$, $NR_5R_6$, (CO)$R_8$, (CO)$OR_4$ or (CO)$NR_5R_6$, wherein R as $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl and interrupted $C_4$-$C_{30}$cycloalkenyl is unsubstituted or substituted by one or more halogen, $NO_2$, CN, Ar, (CO)$R_8$, (CO)$OR_4$, (CO)$NR_5R_6$, O(CO)$R_8$, O(CO)$OR_4$, O(CO)$NR_5R_6$, $NR_7$(CO)$R_8$, $NR_7$(CO)$OR_4$, $OR_4$, $NR_5R_6$, $SR_7$, $SOR_8$, $SO_2R_8$ or $OSO_2R_8$;

$R_1$, $R_2$ and $R_3$ independently of each other are $C_1$-$C_{10}$haloalkyl or Ar, or independently of each other are $C_2$-$C_{10}$haloalkyl which is interrupted by one or more O, S, $NR_7$, O(CO), (CO)O, (CO)$NR_7$ or $NR_7$(CO), wherein $R_1$, $R_2$ and $R_3$ as $C_1$-$C_{10}$haloalkyl, Ar and interrupted $C_2$-$C_{10}$haloalkyl are unsubstituted or substituted by one or more $NO_2$, CN, Ar, (CO)$R_8$, (CO)$OR_4$, (CO)$NR_5R_6$, O(CO)$R_8$, O(CO)$OR_4$, O(CO)$NR_5R_6$, $NR_7$(CO)$R_8$, $NR_7$(CO)$OR_4$, $OR_4$, $NR_5R_6$, $SR_7$, $SOR_8$, $SO_2R_8$ or $OSO_2R_8$;

or $R_1$ and $R_2$, together with the

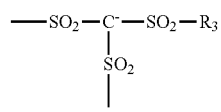

to which they are attached, form a 5-, 6- or 7-membered ring which optionally is interrupted by one or more O, $NR_7$ or CO;

$R_4$ is hydrogen, $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or is $C_2$-$C_{18}$alkyl which is interrupted by one or more O, S, $NR_7$, O(CO), (CO)O, (CO)$NR_7$ or $NR_7$(CO), or is $C_3$-$C_{30}$cycloalkyl which is interrupted by one or more O, S, $NR_7$, O(CO), (CO)O, (CO)$NR_7$ or $NR_7$(CO), or is $C_4$-$C_{30}$cycloalkenyl which is interrupted by one or more O, S, $NR_7$, O(CO), (CO)O, (CO)$NR_7$ or $NR_7$(CO), or $R_4$ is Ar, (CO)$R_8$, (CO)O$R_8$, (CO)$NR_5R_6$ or $SO_2R_8$, wherein $R_4$ as $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_4$-$C_{30}$cycloalkenyl and Ar is unsubstituted or substituted by one or more Ar, OH, $C_1$-$C_{18}$alkyl, $C_1$-$C_{10}$haloalkyl, phenyl-$C_1$-$C_3$-alkyl, $C_3$-$C_{30}$cycloalkyl, halogen, $NO_2$, CN, $C_1$-$C_{18}$alkoxy, phenoxy, phenoxycarbonyl, phenylthio, phenylthiocarbonyl, $NR_5R_6$, $C_1$-$C_{12}$alkylthio, $C_2$-$C_{18}$alkoxycarbonyl, $C_2$-$C_{10}$haloalkanoyl, halobenzoyl, $C_1$-$C_{18}$alkylsulfonyl, phenylsulfonyl, (4-methylphenyl)sulfonyl, $C_1$-$C_{18}$alkylsulfonyloxy, phenylsulfonyloxy, (4-methylphenyl)sulfonyloxy, $C_2$-$C_{18}$alkanoyl, $C_2$-$C_{18}$alkanoyloxy, benzoyl or by benzoyloxy;

$R_5$ and $R_6$ independently of each other are hydrogen, $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or independently of each other are $C_2$-$C_{18}$alkyl which is interrupted by one or more O, S, $NR_7$, O(CO), (CO)O, (CO)$NR_7$ or $NR_7$(CO), or independently of each other are $C_3$-$C_{30}$cycloalkyl which is interrupted by one or more O, S, $NR_7$, O(CO), (CO)O, (CO)$NR_7$ or $NR_7$(CO), or independently of each other are $C_4$-$C_{30}$cycloalkenyl which is interrupted by one or more O, S, $NR_7$, O(CO), (CO)O, (CO)$NR_7$ or $NR_7$(CO), or $R_5$ and $R_6$ independently of each other are Ar, (CO)$R_8$, (CO)O$R_4$ or —$SO_2R_8$, wherein $R_5$ and $R_6$ as $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_4$-$C_{30}$cycloalkenyl and Ar are unsubstituted or substituted by one or more Ar, OH, $C_1$-$C_{18}$alkyl, $C_1$-$C_{10}$haloalkyl, phenyl-$C_1$-$C_3$-alkyl, $C_3$-$C_{30}$cycloalkyl, halogen, $NO_2$, CN, $C_1$-$C_{18}$alkoxy, phenoxy, phenoxycarbonyl, phenylthio, phenylthiocarbonyl, $C_1$-$C_{18}$dialkylamino, $C_1$-$C_{12}$alkylthio, $C_2$-$C_{18}$alkoxycarbonyl, $C_2$-$C_{10}$haloalkanoyl, halobenzoyl, $C_1$-$C_{18}$alkylsulfonyl, phenylsulfonyl, (4-methylphenyl)sulfonyl, $C_1$-$C_{18}$alkylsulfonyloxy, phenylsulfonyloxy, (4-methylphenyl)sulfonyloxy, $C_2$-$C_{18}$alkanoyl, $C_2$-$C_{18}$alkanoyloxy, benzoyl or by benzoyloxy;

or $R_5$ and $R_6$, together with the nitrogen atom to which they are attached, form a 5-, 6- or 7-membered ring which optionally is interrupted by one or more O, $NR_7$ or CO;

$R_7$ is hydrogen, $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or is $C_2$-$C_{18}$alkyl which is interrupted by one or more O, S, O(CO) or (CO)O, or is $C_3$-$C_{30}$cycloalkyl which is interrupted by one or more O, S, O(CO) or (CO)O, or is $C_4$-$C_{30}$cycloalkenyl which is interrupted by one or more O, S, O(CO) or (CO)O; or $R_7$ is Ar, (CO)$R_8$, (CO)O$R_4$, (CO)$NR_5R_6$ or $SO_2R_8$, wherein $R_7$ as $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_4$-$C_{30}$cycloalkenyl and Ar is unsubstituted or substituted by one or more Ar, OH, $C_1$-$C_{18}$alkyl, $C_1$-$C_{10}$haloalkyl, phenyl-$C_1$-$C_3$-alkyl, $C_3$-$C_{30}$cycloalkyl, halogen, $NO_2$, CN, $C_1$-$C_{18}$alkoxy, phenoxy, phenoxycarbonyl, phenylthio, phenylthiocarbonyl, $NR_5R_6$, $C_1$-$C_{12}$alkylthio, $C_2$-$C_{18}$alkoxycarbonyl, $C_2$-$C_{10}$halolkanoyl, halobenzoyl, $C_1$-$C_{18}$alkylsulfonyl, phenylsulfonyl, (4-methylphenyl)sulfonyl, $C_1$-$C_{18}$alkylsulfonyloxy, phenylsulfonyloxy, (4-methylphenyl)sulfonyloxy, $C_2$-$C_{18}$alkanoyl, $C_2$-$C_{18}$alkanoyloxy, benzoyl or by benzoyloxy;

$R_8$ is hydrogen, $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, Ar, $NR_5R_6$, or is $C_2$-$C_{18}$alkyl which is interrupted by one or more O, S, $NR_7$, O(CO), (CO)O, (CO)$NR_7$ or $NR_7$(CO), or is $C_3$-$C_{30}$cycloalkyl which is interrupted by one or more O, S, $NR_7$, CO, O(CO), (CO)O, (CO)$NR_7$ or $NR_7$(CO), or is $C_4$-$C_{30}$cycloalkenyl which is interrupted by one or more O, S, $NR_7$, O(CO), (CO)O, (CO)$NR_7$ or $NR_7$(CO), wherein $R_8$ as $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, Ar interrupted $C_2$-$C_{18}$alkyl, interrupted $C_3$-$C_{30}$cycloalkyl and interrupted $C_4$-$C_{30}$cycloalkenyl is unsubstituted or substituted by one or more Ar, OH, $C_1$-$C_{18}$alkyl, $C_1$-$C_{10}$haloalkyl, phenyl-$C_1$-$C_3$-alkyl, $C_3$-$C_{30}$cycloalkyl, halogen, $NO_2$, CN, $C_1$-$C_{18}$alkoxy, phenoxy, phenoxycarbonyl, phenylthio, phenylthiocarbonyl, $NR_5R_6$, $C_1$-$C_{12}$alkylthio, $C_2$-$C_{18}$alkoxycarbonyl, $C_2$-$C_{10}$haloalkanoyl, halobenzoyl, $C_1$-$C_{18}$alkylsulfonyl, phenylsulfonyl, (4-methylphenyl)sulfonyl, $C_1$-$C_{18}$alkylsulfonyloxy, phenylsulfonyloxy, (4-methylphenyl)sulfonyloxy, $C_2$-$C_{18}$alkanoyl, $C_2$-$C_{18}$alkanoyloxy, benzoyl or by benzoyloxy; and Ar is phenyl, biphenylyl, fluorenyl, naphthyl, anthracyl, phenanthryl, or heteroaryl, wherein the phenyl, biphenylyl, fluorenyl, naphthyl, anthracyl, phenanthryl, or heteroaryl are unsubstituted or substituted by one or more $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or are substituted by $C_2$-$C_{18}$alkyl which is interrupted by one or more O, S, $NR_7$, O(CO), (CO)O, (CO)$NR_7$ or $NR_7$(CO), or are substituted by $C_3$-$C_{30}$cycloalkyl which is interrupted by one or more O, S, $NR_7$, O(CO), (CO)O, (CO)$NR_7$ or $NR_7$(CO), or are substituted by $C_4$-$C_{30}$cycloalkenyl which is interrupted by one or more O, S, $NR_7$, O(CO), (CO)O, (CO)$NR_7$ or $NR_7$(CO), or are substituted by one or more halogen, $NO_2$, CN, phenyl, biphenylyl, naphthyl, heteroaryl, (CO)$R_8$, (CO)O$R_4$, (CO)$NR_5R_6$, O(CO)$R_8$, O(CO)O$R_4$, O(CO)$NR_5R_6$, $NR_7$(CO)$R_8$, $NR_7$(CO)O$R_4$, O$R_4$, $NR_5R_6$, $SR_7$, SO$R_8$, $SO_2R_8$ or OSO$_2R_8$, optionally the substituents $C_1$-$C_{18}$alkyl, $C_2$-$C_{12}$alkenyl, (CO)$R_8$, (CO)O$R_4$, (CO)$NR_5R_6$, O(CO)$R_8$, O(CO)O$R_4$, O(CO)$NR_5R_6$, $NR_7$(CO)$R_8$, $NR_7$(CO)O$R_4$, O$R_4$, $NR_5R_6$, $SR_7$, SO$R_8$, $SO_2R_8$ or OSO$_2R_8$, form 5-, 6- or 7-membered rings, via the radicals $C_1$-$C_{18}$alkyl, $C_2$-$C_{12}$alkenyl, $R_4$, $R_5$, $R_6$, $R_7$ or $R_8$, with further substituents on the phenyl, biphenylyl, fluorenyl, naphthyl, anthracyl, phenanthryl or heteroaryl or with one of the carbon atoms of phenyl, biphenylyl, fluorenyl, naphthyl, anthracyl, phenanthryl, or heteroaryl.

The compounds of the formula I are characterized in that carbonyl functional group is substituted on one aryl ring of triarylsulfonium salts, and that they have trisulfonylmethide anion as the counter anion.

Of interest are in particular compounds of the formula I, wherein $Ar_1$ is phenylene, biphenylene, naphthylene or heteroarylene, all of which are unsubstituted or are substituted by one or more $C_1$-$C_{18}$alkyl, $C_1$-$C_{10}$haloalkyl, halogen, $NO_2$, CN, Ar, $OR_4$, $NR_5R_6$ or $SR_7$;

wherein optionally the substituents $C_1$-$C_{18}$alkyl, $OR_4$, $NR_5R_6$ or $SR_7$ form 5-, 6- or 7-membered rings, via the radicals $C_1$-$C_{18}$alkyl, $R_4$, $R_5$, $R_6$ or $R_7$ with further substituents on the phenylene, biphenylene, naphthylene or heteroarylene, or with one of the carbon atoms of the phenylene, biphenylene, naphthylene or heteroarylene;

$Ar_2$ and $Ar_3$ independently of each other are phenyl, naphthyl, biphenylyl or heteroaryl, wherein the phenyl, naphthyl, biphenylyl or heteroaryl are optionally substituted by one or more $C_1$-$C_{18}$alkyl, $C_1$-$C_{10}$haloalkyl, halogen, $NO_2$, CN, Ar, $OR_4$, $NR_5R_6$ or $SR_7$;

wherein optionally the substituents $C_1$-$C_{18}$alkyl, $OR_4$, $NR_5R_6$ or $SR_7$ form 5-, 6- or 7-membered rings, via the radicals $C_1$-$C_{18}$alkyl, $R_4$, $R_5$, $R_6$ or $R_7$ with further substituents on the phenyl, biphenylyl, naphthyl or heteroaryl, or with one of the carbon atoms of the phenyl, biphenylyl, naphthyl or heteroaryl;

or $Ar_1$ and $Ar_2$ together with a direct bond, O, S, $NR_7$ or (CO), form a fused ring system;

or $Ar_1$ and $Ar_2$ together with $C_1$-$C_2$alkylene, O, S, $NR_7$ or (CO), form a 5-, 6-, or 7-membered ring;

or $Ar_2$ and $Ar_3$ together with a direct bond, O, S, $NR_7$ or (CO) form a fused ring system;

or $Ar_2$ and $Ar_3$ together with $C_1$-$C_2$alkylene, O, S, $NR_7$ or (CO), form a 5-, 6-, or 7-membered ring;

or $Ar_1$ and $Ar_2$, together with the

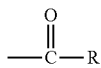

which is attached to $Ar_1$, form

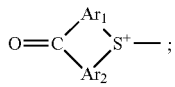

R is $C_1$-$C_{18}$alkyl, $C_1$-$C_{10}$haloalkyl, Ar, $OR_4$ or $NR_5R_6$;
wherein R as $C_1$-$C_{18}$alkyl and $C_1$-$C_{10}$haloalkyl, optionally is substituted by one or more halogen, $NO_2$, CN, Ar, $OR_4$, $NR_5R_6$ or $SR_7$;
$R_1$, $R_2$ and $R_3$ independently of each other are $C_1$-$C_{10}$haloalkyl;
$R_4$ is hydrogen, $C_1$-$C_{18}$alkyl, Ar, $(CO)R_8$ or $SO_2R_8$;
$R_5$ and $R_6$ independently of each other are hydrogen, $C_1$-$C_{18}$alkyl, Ar, $(CO)R_8$ or $SO_2R_8$;
$R_7$ is hydrogen, $C_1$-$C_{18}$alkyl, Ar, $(CO)R_8$ or $SO_2R_8$;
$R_8$ is hydrogen, $C_1$-$C_{18}$alkyl or Ar; and
Ar is phenyl, biphenylyl or naphthyl, which phenyl, biphenylyl or naphthyl are unsubstituted or are substituted by one or more $C_1$-$C_{18}$alkyl, halogen, $NO_2$, CN, $OR_4$, $NR_5R_6$ or $SR_7$; optionally the substituents $C_1$-$C_{18}$alkyl, $OR_4$, $NR_5R_6$ or $SR_7$, form 5-, 6- or 7-membered rings, via the radicals $C_1$-$C_{18}$alkyl, $R_4$, $R_5$, $R_6$ or $R_7$, with further substituents on the phenyl, biphenylyl or naphthyl or with one of the carbon atoms of the phenyl, biphenylyl or naphthyl.

Of interest further are such compounds of the formula I, wherein $Ar_1$ is phenylene or heteroarylene, both unsubstituted or are substituted by one or more $C_1$-$C_{18}$alkyl or $OR_4$;
$Ar_2$ and $Ar_3$ independently of each other are phenyl, biphenylyl or heteroaryl,
wherein the phenyl, biphenylyl or heteroaryl are unsubstituted or substituted by one or more $C_1$-$C_{18}$alkyl, Ar or $OR_4$;
or $Ar_1$ and $Ar_2$ together with a direct bond form a fused ring;
or $Ar_1$ and $Ar_2$ together with the

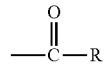

which is attached to the $Ar_1$, form

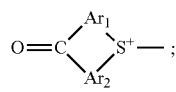

R is $C_1$-$C_{18}$alkyl or Ar;
$R_1$, $R_2$ and $R_3$ independently of each other are $C_1$-$C_{10}$haloalkyl;
$R_4$ is hydrogen, $C_1$-$C_{18}$alkyl, Ar, $(CO)R_8$ or $SO_2R_8$;
$R_5$ and $R_6$ independently of each other are hydrogen, $C_1$-$C_{18}$alkyl, Ar, $(CO)R_8$ or $SO_2R_8$;
$R_7$ is hydrogen, $C_1$-$C_{18}$alkyl, Ar, $(CO)R_8$ or $SO_2R_8$;
$R_8$ is hydrogen, $C_1$-$C_{18}$alkyl or Ar; and
Ar is phenyl, biphenylyl or naphthyl, which phenyl, biphenylyl or naphthyl are unsubstituted or substituted by one or more $C_1$-$C_{18}$alkyl, halogen, $NO_2$, CN, $OR_4$, $NR_5R_6$ or $SR_7$; optionally the substituents $C_1$-$C_{18}$alkyl, $OR_4$, $NR_5R_6$ or $SR_7$, form 5-, 6- or 7-membered rings, via the radicals $C_1$-$C_{18}$alkyl, $R_4$, $R_5$, $R_6$ or $R_7$, with further substituents on the phenyl, biphenylyl or naphthyl or with one of the carbon atoms of the phenyl, biphenylyl or naphthyl.

Further compounds of the invention encompass compounds of the formula I, wherein
$Ar_1$ is phenylene or heteroarylene, which are unsubstituted or substituted by $OR_4$; or $Ar_1$ is

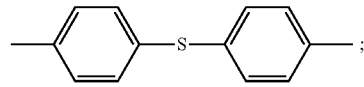

$Ar_2$ and $Ar_3$ independently of each other are phenyl or biphenylyl,
wherein the phenyl or biphenylyl are unsubstituted or are substituted by $C_1$-$C_{18}$alkyl;
or $Ar_1$ and $Ar_2$ together with a direct bond, form a fused ring system;
or $Ar_1$ and $Ar_2$ together with the

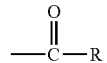

which is attached to $Ar_1$, form

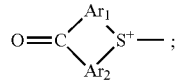

R is $C_1$-$C_{18}$alkyl or Ar;

$R_1$, $R_2$ and $R_3$ independently of each other are $C_1$-$C_{10}$haloalkyl, in particular trifluoromethyl;

$R_4$ is hydrogen, $C_1$-$C_{18}$alkyl, Ar, (CO)$R_8$ or $SO_2R_8$, in particular alkyl;

Ar is phenyl which phenyl is unsubstituted or is substituted by $OR_4$ or halogen.

A particular subject of the invention are compounds of the formula I, wherein $Ar_1$ is phenylene or heteroarylene, which are unsubstituted or substituted by $OR_4$;

$Ar_2$ and $Ar_3$ independently of each other are phenyl or biphenylyl, wherein the phenyl or biphenylyl are unsubstituted or are substituted by $C_1$-$C_{18}$alkyl;

or $Ar_1$ and $Ar_2$ together with a direct bond, form a fused ring system;

or $Ar_1$ and $Ar_2$ together with the

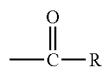

which is attached to $Ar_1$, form

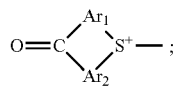

R is Ar;

$R_1$, $R_2$ and $R_3$ are $C_1$-$C_{10}$haloalkyl;

$R_4$ is $C_1$-$C_{18}$alkyl; and

Ar is phenyl which phenyl is unsubstituted or is substituted by $OR_4$.

Further interesting are compounds of the formula I, wherein $Ar_1$ is phenylene or heteroarylene, in particular phenylene or thioxantheylene, wherein the phenylene or heteroarylene are unsubstituted or substituted by $OR_4$;

$Ar_2$ and $Ar_3$ independently of each other are phenyl or biphenylyl, wherein the phenyl or biphenylyl are unsubstituted or are substituted by $C_1$-$C_{18}$alkyl;

or $Ar_1$ and $Ar_2$ together with the

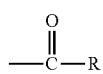

which is attached to $Ar_1$, form

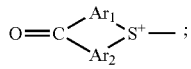

R is Ar;

$R_1$, $R_2$ and $R_3$ are $C_1$-$C_{10}$haloalkyl;

$R_4$ is $C_1$-$C_{18}$alkyl; and

Ar is phenyl which phenyl is unsubstituted or is substituted by $OR_4$.

In particular interesting are the compounds as given in the examples 1-4, as well as the compounds the following formulae (a)-(d):

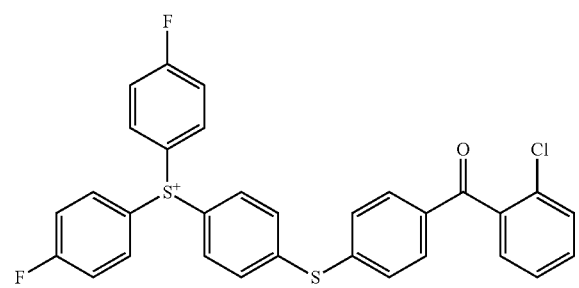
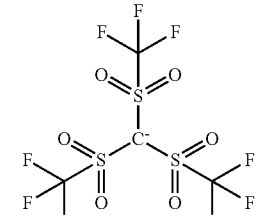

(a)

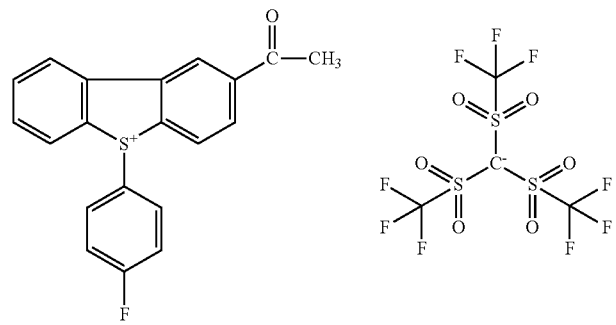

(b)

-continued

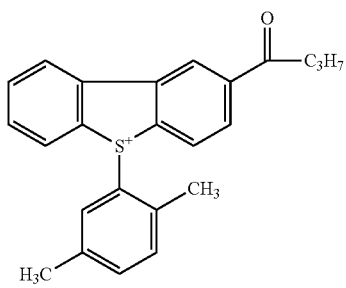
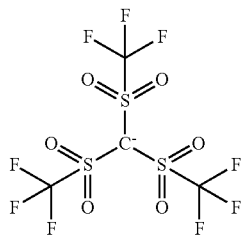

(c)

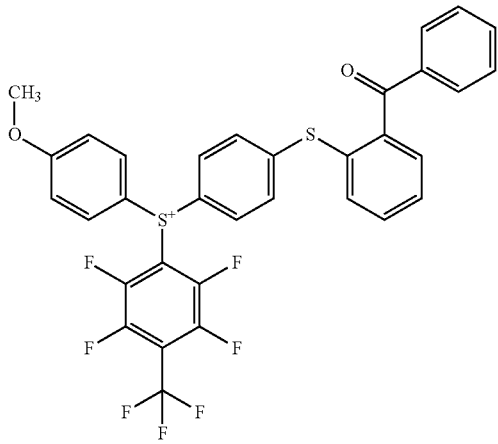
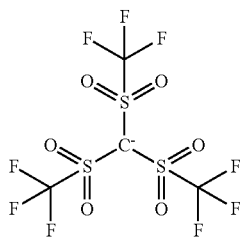

(d)

$C_1$-$C_{18}$alkyl is linear or branched and is, for example, $C_1$-$C_{16}$-, $C_1$-$C_{12}$-, $C_1$-$C_8$-, $C_1$-$C_6$- or $C_1$-$C_4$-alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl and octadecyl, preferably $C_1$-$C_4$alkyl, such as methyl, isopropyl or butyl.

$C_2$-$C_{18}$alkyl which is interrupted by one or more O, S, $NR_7$, O(CO), (CO)O, (CO)$NR_7$ and/or $NR_7$(CO) is, for example, interrupted from one to five times, for example from one to three times or once or twice, by non-successive O, S, $NR_7$, O(CO), (CO)O, (CO)$NR_7$ and/or $NR_7$(CO). Accordingly, resulting structural units are for example: O(CH$_2$)$_2$OH, O(CH$_2$)$_2$OCH$_3$, O(CH$_2$CH$_2$O)$_2$CH$_2$CH$_3$, CH$_2$—O—CH$_3$, CH$_2$CH$_2$—O—CH$_2$CH$_3$, [CH$_2$CH$_2$O]$_y$—CH$_3$, wherein y=1-5, (CH$_2$CH$_2$O)$_5$CH$_2$CH$_3$, CH$_2$—CH(CH$_3$)—O—CH$_2$—CH$_2$CH$_3$, CH$_2$—CH(CH$_3$)—O—CH$_2$—CH$_3$, S(CH$_2$)$_2$SCH$_3$, (CH$_2$)$_2$NHCH$_3$, (CH$_2$)$_2$O(CO)CH$_3$, (CH$_2$)$_2$(CO)OCH$_3$ or (CH$_2$)$_2$NH(CO)CH$_3$.

If, in the context of the present invention a group, e.g. alkyl or alkylene, is interrupted by one or more defined radicals, e.g. O, S, $NR_7$, O(CO), (CO)O, (CO)$NR_7$ and/or $NR_7$(CO), the "interrupting" radicals not only are meant to be situated in between the interrupted group, for example the alkyl or alkylene, but also are meant to be terminal.

$C_3$-$C_{30}$cycloalkyl is a mono- or polycyclic aliphatic ring, for example a mono-, bi- or tricyclic aliphatic ring, e.g. $C_3$-$C_{20}$-, $C_3$-$C_{18}$-, $C_3$-$C_{12}$-, $C_3$-$C_{10}$cycloalkyl. $C_3$-$C_{30}$cycloalkyl in the context of the present application is to be understood as alkyl which at least comprises one ring, i.e. also carbocyclic aliphatic rings, which are substituted by alkyl are covered by this definition. Examples of monocyclic rings are cyclopropyl, cyclobutyl, cyclopentyl, cyclohexyl, or cycloheptyl, especially cyclopentyl and cyclohexyl. Further examples are structures like

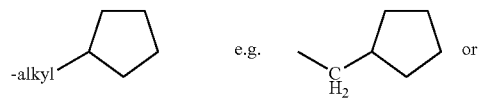
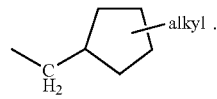

Examples of polycyclic rings are perhydroanthracyl, perhydrophenyathryl, perhydronaphthyl, perhydrofluorenyl, perhydrochrysenyl, perhydropicenyl, adamantyl, bicyclo[1.1.1]pentyl, bicyclo[4.2.2]decyl, bicyclo[2.2.2]octyl, bicyclo[3.3.2]decyl, bicyclo[4.3.2]undecyl, bicyclo[4.3.3]dodecyl, bicyclo[3.3.3]undecyl, bicyclo[4.3.1]decyl, bicyclo[4.2.1]nonyl, bicyclo[3.3.1]nonyl, bicyclo[3.2.1]octyl,

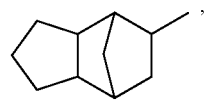

and the like. Also alkyl-substituted polycyclic and bridged rings are meant to be covered by the definition "cycloalkyl" in the context of the present invention, e.g.

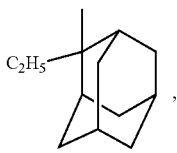 , 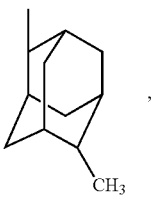 , etc.

Also "spiro"-cycloalkyl compounds are covered by the definition $C_3$-$C_{30}$cycloalkyl in the present context, e.g. spiro[5.2]octyl, spiro[5.4]decyl, spiro[5.5]undecyl. More examples of polycyclic cycloalkyl groups, which are subject of the respective definition in the compounds of the present invention are listed in EP 878738, page 11 and 12, wherein to the formulae (1)-(46) a bond to achieve the "yl" has to be added. The person skilled in the art is aware of this fact.

In general, the cycloaliphatic rings may form repeating structural units.

$C_3$-$C_{30}$cycloalkyl which is interrupted by one or more O, S, $NR_7$, O(CO), (CO)O, (CO)$NR_7$ and/or $NR_7$(CO) is a mono- or polycyclic aliphatic ring which is interrupted by one or more O, S, $NR_7$, O(CO), (CO)O, (CO)$NR_7$ and/or $NR_7$(CO), for example,

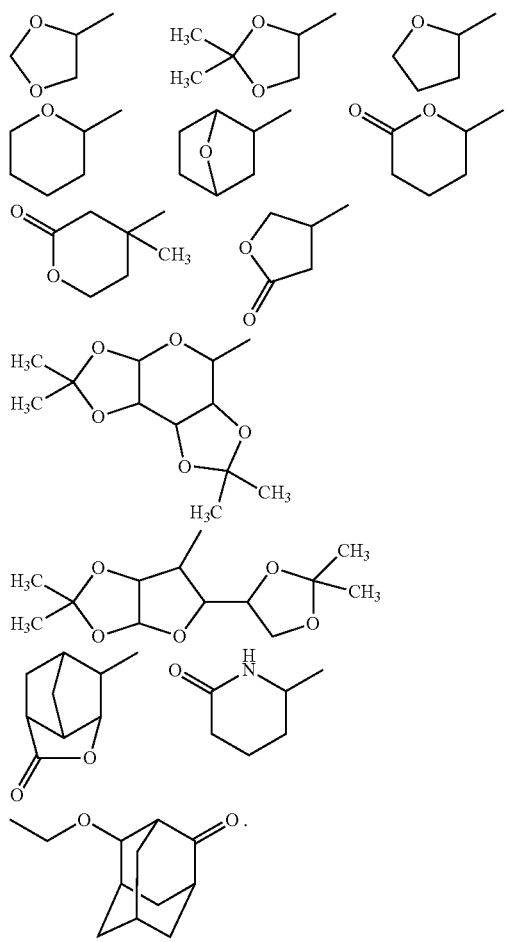

$C_2$-$C_{12}$alkenyl radicals are for example mono- or polyunsaturated, linear or branched and are for example $C_2$-$C_8$-, $C_2$-$C_6$- or $C_2$-$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

$C_4$-$C_{30}$cycloalkenyl is a mono- or polycyclic and mono- or polyunsaturated ring, for example a mono-, bi-, tri- or tetracyclic mono- or polyunsaturated ring, e.g. $C_4$-$C_{20}$-, $C_4$-$C_{18}$-, $C_4$-$C_{12}$-, $C_4$-$C_{10}$cycloalkenyl. Examples of cycloalkenyl are cyclobutenyl, cyclopentenyl, cyclohexenyl, cycloheptenyl. Also bridged alkenyl groups are covered by the above definition, for example

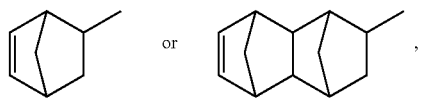

etc., especially cyclopentenyl, cyclohexenyl,

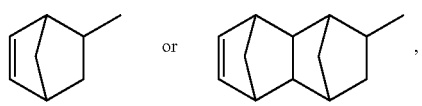

$C_4$-$C_{30}$cycloalkenyl which is interrupted by one or more O, S, $NR_7$, O(CO), (CO)O, (CO)$NR_7$ and/or $NR_7$(CO) is a mono- or polycyclic and mono- or polyunsaturated ring, which is interrupted by one or more O, S, $NR_7$, O(CO), (CO)O, (CO)$NR_7$ and/or $NR_7$(CO), for example,

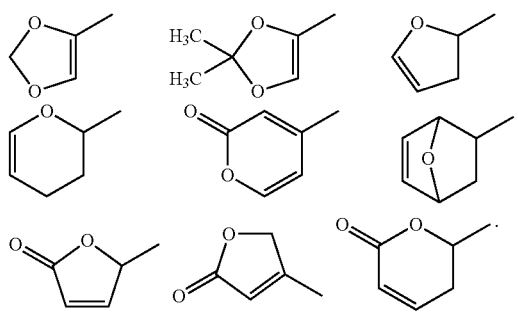

$C_1$-$C_{18}$alkylene is linear or branched alkylene, e.g. $C_1$-$C_2$-$C_2$-$C_5$alkylene. Examples are methylene, ethylene, propylene, butylene, pentylene, hexylene.

Substituted phenyl carries from one to five, for example one, two or three, especially one or two, substituents on the phenyl ring. The substitution is preferably in the 4-, 3,4-, 3,5- or 3,4,5-position of the phenyl ring.

When the radicals phenyl, biphenyl, naphthyl, fluorenyl, phenanthryl, anthracyl and heteroaryl are substituted by one or more radicals, they are, for example, mono- to pentasubstituted, for example mono-, di- or tri-substituted, especially mono- or di-substituted.

When Ar is phenyl, biphenyl, fluorenyl, naphthyl, anthracyl, phenanthryl, or heteroaryl substituted by one or more $C_1$-$C_{18}$alkyl, $C_2$-$C_{12}$alkenyl, (CO)$R_8$, (CO)$OR_4$, (CO)$NR_5R_6$, O(CO)$R_8$, O(CO)$OR_4$, O(CO)$NR_5R_6$, $NR_7$(CO)$R_8$, $NR_7$(CO)$OR_4$, $OR_4$, $NR_5R_6$, $SR_7$, $SOR_8$, $SO_2R_8$ and/or $OSO_2R_8$ and the substituents $C_1$-$C_{18}$alkyl, $C_2$-$C_{12}$alkenyl, (CO)$R_8$, (CO)$OR_4$, (CO)$NR_5R_6$, O(CO)$R_8$, O(CO)$OR_4$, O(CO)$NR_5R_6$, $NR_7$(CO)$R_8$, $NR_7$(CO)$OR_4$, $OR_4$, $NR_5R_6$, $SR_7$, $SOR_8$, $SO_2R_8$ and/or $OSO_2R_8$, form 5-, 6- or 7-membered rings, via the radicals $C_1$-$C_{18}$alkyl, $C_2$-$C_{12}$alkenyl, $R_4$, $R_5$, $R_6$, $R_7$ and/or $R_8$, with further substituents on the phenyl, biphenyl, fluorenyl, naphthyl, anthracyl, phenanthryl, or heteroaryl or with one of the carbon atoms of the phenyl, biphenyl, fluorenyl, naphthyl, anthracyl, phenanthryl, or heteroaryl, for example the following structural units are obtained

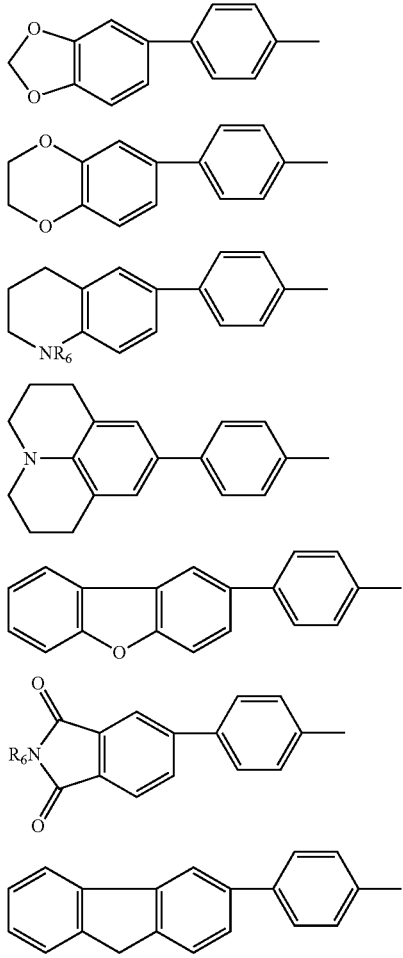

etc.

If in Ar the substituents $C_1$-$C_{18}$alkyl form alkylene bridges from one carbon atom of the biphenyl, naphthyl, or fluorenyl ring to another carbon atom of said ring, in particular ethylene, propylene and butylene bridges are formed and for example the following structures are obtained

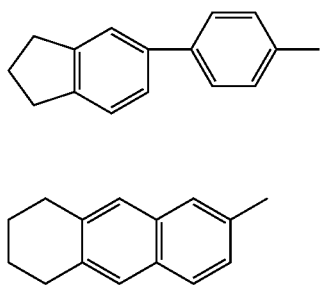

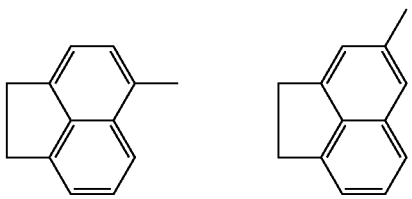

etc. The definition according to the present application in this connection also is intended to cover branched alkylene bridges:

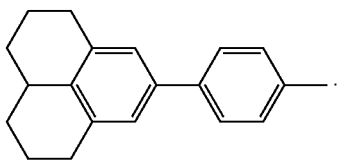 [SMILES: Cc1ccc(-c2cc3c4c(c2)CCCC4CCC3)cc1]

In case said alkylene bridges are condensed with further phenyl rings for example the following structure is given

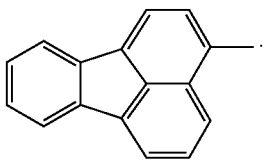 [SMILES: Cc1ccc2c3c(cccc13)-c1ccccc1-2]

When $Ar_1$ is phenylene, biphenylene, naphthylene,

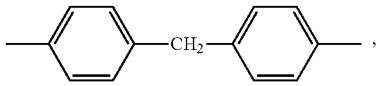

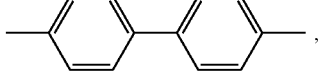

heteroarylene, oxydiphenylene or

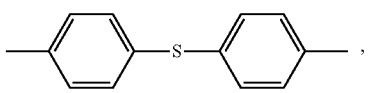

all of which are substituted by one or more $C_1$-$C_{18}$alkyl, $C_2$-$C_{12}$alkenyl, (CO)$R_8$, (CO)O$R_4$, (CO)N$R_5R_6$, O(CO)$R_8$, O(CO)O$R_4$, O(CO)N$R_5R_6$, N$R_7$(CO)$R_8$, N$R_7$(CO)O$R_4$, O$R_4$, N$R_5R_6$, S$R_7$, SO$R_8$, SO$_2R_8$ and/or OSO$_2R_8$, and the substituents $C_1$-$C_{18}$alkyl, $C_2$-$C_{12}$alkenyl, (CO)$R_8$, (CO)O$R_4$, (CO)N$R_5R_6$, O(CO)$R_8$, O(CO)O$R_4$, O(CO)N$R_5R_6$, N$R_7$(CO)$R_8$, N$R_7$(CO)O$R_4$, O$R_4$, N$R_5R_6$, S$R_7$, SO$R_8$, SO$_2R_8$ and/or OSO$_2R_8$ form 5-, 6- or 7-membered rings, via the radicals $C_1$-$C_{18}$alkyl, $C_2$-$C_{12}$alkenyl, $R_4$, $R_5$, $R_6$, $R_7$ and/or $R_8$, with further substituents on the phenylene, biphenylene, naphthylene,

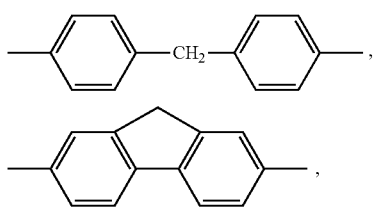

heteroarylene, oxydiphenylene or

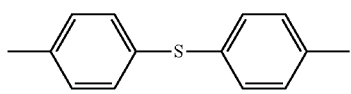

or with one of the carbon atoms of the phenylene, biphenylene, naphthylene,

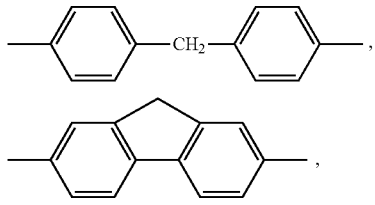

heteroarylene,

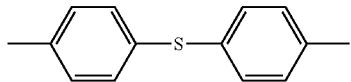

or oxydiphenylene, for example the following structural units are obtained

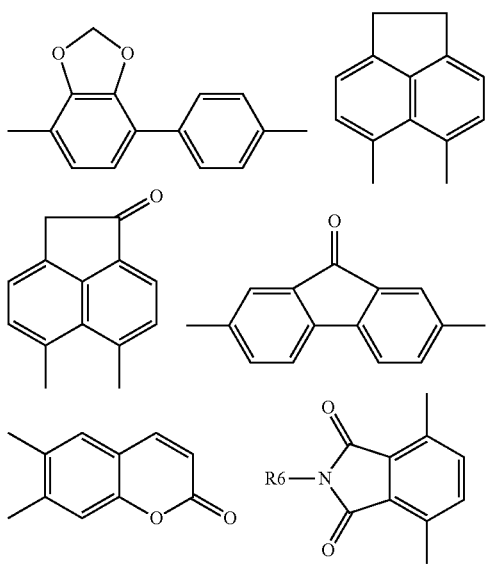

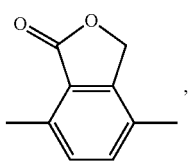

etc.

If $Ar_1$ and $Ar_2$ together with a direct bond, O, S, $NR_7$ or (CO), form a fused ring systems, for example the following structural units are obtained,

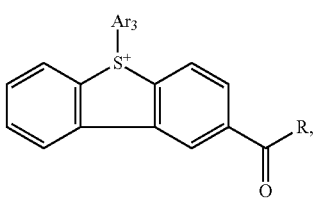

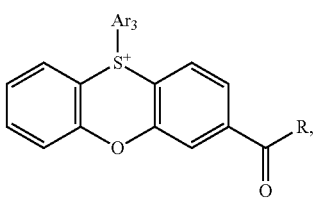

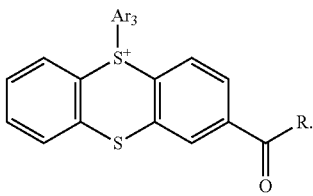

If $Ar_1$ and $Ar_2$ together with $C_1$-$C_2$alkylene, O, S, $NR_7$ or (CO), form a 5-, 6-, or 7-membered ring, for example the following structural units are obtained,

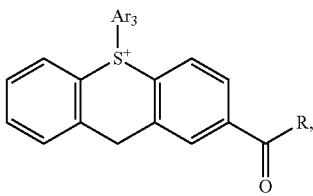

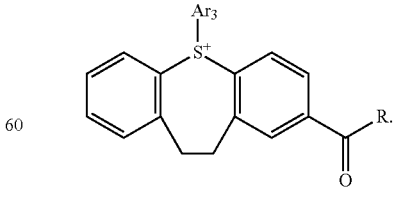

If $Ar_2$ and $Ar_3$ together with a direct bond, O, S, $NR_7$ or (CO), form a fused ring system, for example the following structural units are obtained,

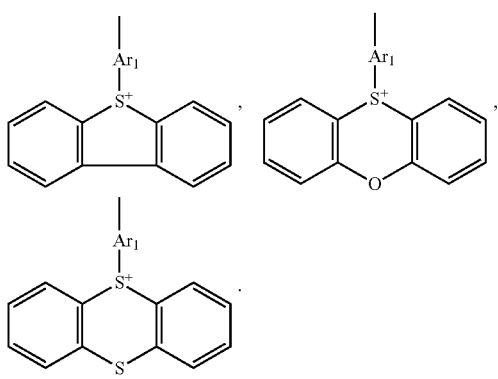

If Ar$_2$ and Ar$_3$ together with C$_1$-C$_2$alkylene, O, S, NR$_7$, (CO), form a 5-, 6-, or 7-membered ring, for example the following structural units are obtained,

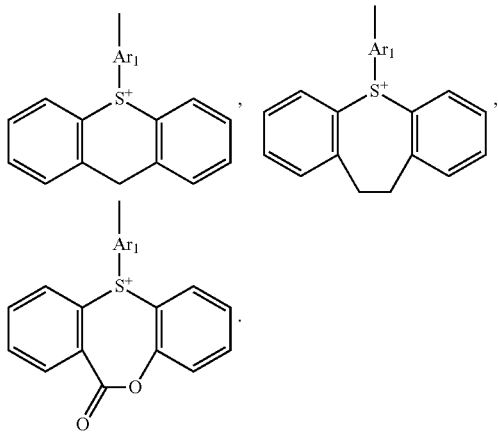

When Ar$_1$ and Ar$_2$ together the

which is attached to the Ar$_1$, form

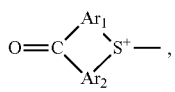

for example the following structural units are obtained,

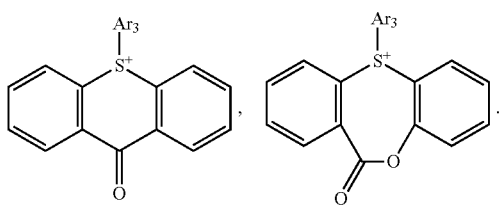

C$_2$-C$_{18}$alkanoyl is e.g. C$_2$-C$_{12}$, C$_2$-C$_8$-, C$_2$-C$_6$- or C$_2$-C$_4$alkanoyl, wherein the alkyl moiety is linear or branched. Examples are acetyl, propionyl, butanoyl or hexanoyl, especially acetyl. C$_1$-C$_{18}$alkoxy is e.g. C$_1$-C$_{12}$-, C$_1$-C$_8$-, C$_1$-C$_6$-, C$_1$-C$_4$alkoxy, and is linear or branched. Examples are methoxy, ethoxy, propoxy, n-butoxy, t-butoxy, octyloxy and dodecyloxy.

In C$_1$-C$_{12}$alkylthio the alkyl moiety is for example linear or branched. Examples are methylthio, ethylthio, propylthio or butylhtio.

C$_2$-C$_{10}$alkoxycarbonyl is (C$_1$-C$_{17}$alkyl)-O—C(O)—, wherein C$_1$-C$_{17}$alkyl is linear or branched and is as defined above up to the appropriate number of carbon atoms. Examples are C$_2$-C$_{10}$-, C$_2$-C$_8$-, C$_2$-C$_6$- or C$_2$-C$_4$alkoxycarbonyl, such as methoxycarbonyl, ethoxycarbonyl, propoxycarbonyl, butoxycarbonyl or pentoxycarbonyl.

C$_1$-C$_{10}$haloalkyl are for example C$_1$-C$_8$-, C$_1$-C$_6$- or C$_1$-C$_4$-alkyl mono- or poly-substituted by halogen, the alkyl moieties being, for example, as defined above. There are, for example, from 1 to 23 halogen substituents at the alkyl radical. Examples are chloromethyl, trichloromethyl, trifluoromethyl, nonafluorobutyl or 2-bromopropyl, especially trifluoromethyl or trichloromethyl. Preferred is C$_1$-C$_{10}$fluoroalkyl.

C$_2$-C$_{10}$haloalkanoyl is (C$_1$-C$_9$haloalkyl)-C(O)—, wherein C$_1$-C$_9$haloalkyl is as defined above up to the appropriate number of carbon atoms. Examples are chloroacetyl, trichloroacetyl, trifluoroacetyl, pentafluoropropionyl, perfluorooctanoyl, or 2-bromopropionyl, especially trifluoroacetyl or trichloroacetyl.

Halobenzoyl is benzoyl which is mono- or poly-substituted by halogen and/or C$_1$-C$_4$haloalkyl, C$_1$-C$_4$-haloalkyl being as defined above. Examples are pentafluorobenzoyl, trichlorobenzoyl, trifluoromethylbenzoyl, especially pentafluorobenzoyl.

Halogen is fluorine, chlorine, bromine or iodine, especially chlorine or fluorine, preferably fluorine.

Phenyl-C$_1$-C$_3$alkyl is, for example, benzyl, 2-phenylethyl, 3-phenylpropyl, α-methylbenzyl or α,α-dimethylbenzyl, especially benzyl.

If R$_5$ and R$_6$ together with the nitrogen atom to which they are bonded form a 5-, 6- or 7-membered ring that optionally is interrupted by O, NR$_7$ or CO, for example the following structures are obtained

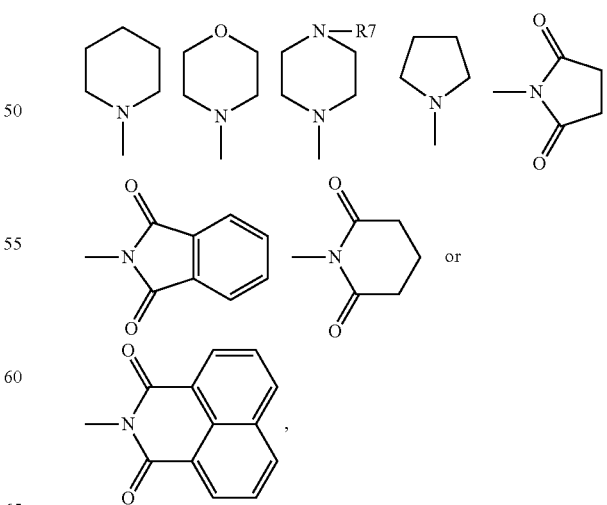

etc.

The definition $C_1$-$C_{18}$alkylsulfonyl, refers to the corresponding radical $C_1$-$C_{18}$alkyl, as described in detail above, being linked to a sulfonyl group (—$SO_2$—). Accordingly, also phenylsulfonyl and (4-methylphenyl)sulfonyl refer to the corresponding radicals linked to a sulfonyl group.

$C_2$-$C_{18}$alkanoyloxy is ($C_1$-$C_{17}$alkyl)-C(O)—O—, wherein $C_1$-$C_{17}$alkyl is linear or branched and is as defined above up to the appropriate number of carbon atoms. Examples are $C_2$-$C_{10}$-, $C_2$-$C_8$-, $C_2$-$C_6$- or $C_2$-$C_4$alkanoyloxy, such as acetyloxy, ethanoyloxy, propanoyloxy, butanoyloxy or hexanoyloxy.

$C_1$-$C_{18}$alkylsulfonyloxy is ($C_1$-$C_{18}$alkyl)-S(O)$_2$—O—, wherein $C_1$-$C_{18}$alkyl is linear or branched and is as defined above up to the appropriate number of carbon atoms. Examples are $C_1$-$C_{10}$-, $C_1$-$C_8$-, $C_1$-$C_6$- or $C_1$-$C_4$alkylsulfonyloxy, such as methanesulfonyloxy, propanesulfonyloxy or hexanesulfonyloxy.

Accordingly, also phenylsulfonyloxy and (4-methylphenyl)sulfonyloxy refer to the corresponding radicals linked to a —S(O)$_2$—O— group.

In the present application, the term "heteroaryl" denotes unsubstituted and substituted radicals, for example 3-thienyl, 2-thienyl,

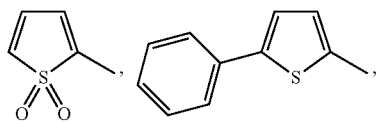

wherein $R_4$ and $R_5$ are as defined above, thianthrenyl, isobenzofuranyl, xanthenyl, thioxanthenyl, phenoxanthiinyl,

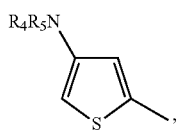

wherein Y is S, O or $NR_6$ and $R_6$ is as defined above. Examples thereof are pyrazolyl, thiazolyl, oxazolyl, isothiazolyl or isoxazolyl. Also included are, for example, furyl, pyrrolyl, 1,2,4-triazolyl,

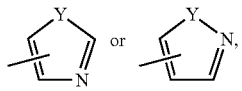

or 5-membered ring heterocycles having a fused-on aromatic group, for example benzimidazolyl, benzothienyl, benzofuranyl, benzoxazolyl and benzothiazolyl.

Other examples of "heteroaryls" are pyridyl, especially 3-pyridyl,

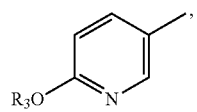

wherein $R_3$ is as defined above, pyrimidinyl, pyrazinyl, 1,3,5-triazinyl, 2,4-, 2,2- or 2,3-diazinyl, indolizinyl, isoindolyl, indolyl, indazolyl, purinyl, isoquinolyl, quinolyl, phenoxazinyl or phenazinyl. In this Application, the term "heteroaryl" also denotes the radicals thioxanthyl, xanthyl,

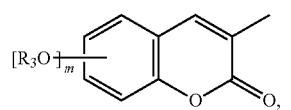

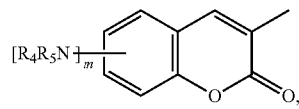

wherein m is 0 or 1 and $R_3$, $R_4$, $R_5$ are as defined above,

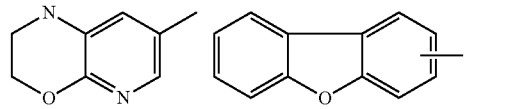

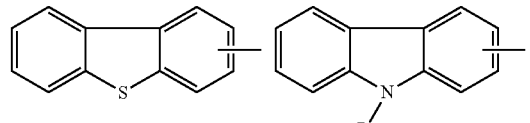

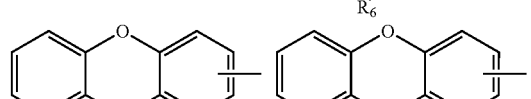

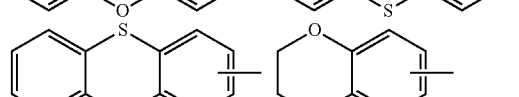

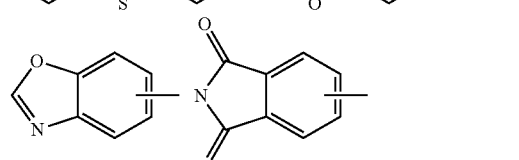

anthraquinonyl. Each of the heteroaryls may carry the substituents indicated above.

Phenylene is

Naphthylene is

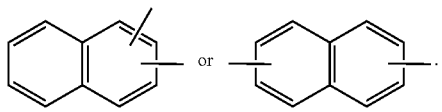

Biphenylene is

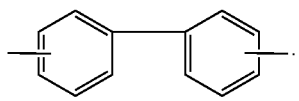

Oxydiphenylene is

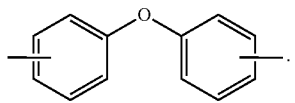

Heteroarylene is a divalent radical of the heteroaryl rings as described above, for example

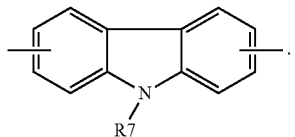

Groups having a —O—C-bond or a —O—Si-bond which cleaves upon the action of an acid, and being substituents of the radicals $Ar_1$, $Ar_2$ and $Ar_3$ are acid cleavable groups which increase the solubility of the compounds of formula I in the alkaline developer after reaction with an acid. This effect is for example described in U.S. Pat. No. 4,883,740.

Examples of groups suitable as such substituents are for example known orthoesters, trityl and benzyl groups, tert.-butyl esters of carboxylic acids, tert.-butyl carbonates of phenols or silyl ethers of phenols, e.g. $OSi(CH_3)_3$, $CH_2(CO)OC(CH_3)_3$, $(CO)OC(CH_3)_3$, $O(CO)OC(CH_3)_3$ or

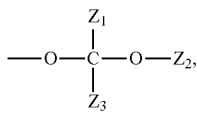

wherein $Z_1$ and $Z_2$ independently of one another are hydrogen, $C_1$-$C_5$alkyl, $C_3$-$C_8$-cycloalkyl, phenyl-$C_1$-$C_3$-alkyl, or $Z_1$ and $Z_2$ together are $C_2$-$C_5$alkylene, and $Z_3$ is unsubstituted or halogen-substituted $C_1$-$C_5$alkyl, unsubstituted or halogen-substituted $C_3$-$C_8$cycloalkyl, or phenyl-$C_1$-$C_3$-alkyl, or, if $Z_1$ and $Z_2$ together are no $C_2$-$C_5$alkylene, $Z_3$ and $Z_2$ together may be $C_2$-$C_5$alkylene, which may be interrupted by O or S.

Examples of

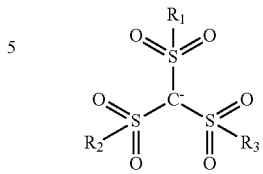

are $(C_8F_{17}SO_2)_3C^-$, $(CF_3SO_2)_3C^-$, $(C_4F_9SO_2)_3C^-$, $(CF_3SO_2)_2(C_4F_9SO_2)C^-$,

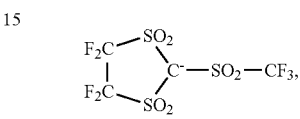

$C_6F_5SO_2C^-(SO_2CF_3)_2$ etc.

The terms "and/or" or "or/and" throughout the specification are meant to express that not only one of the defined alternatives (substituents) may be present, but also several of the defined alternatives (substituents) together, namely mixtures of different alternatives (substituents).

The term "optionally substituted" means unsubstituted or substituted.

The term "optionally interrupted" means uninterrupted or interrupted.

"optionally" is intended to cover both corresponding options which are defined.

The term "at least" is meant to define one or more than one, for example one or two or three, preferably one or two.

The preferences referring to the compounds of the formula I as given hereinbefore and in the context of the whole text, are intended not to refer to the compounds as such only, but to all the compositions, comprising the compounds of the formula I, to the photoinitiator mixtures comprising said compounds, as well as the use or process in which said compounds are employed.

The sulfonium salts of formula I can generally be prepared by a variety of methods described, for instance, by J. V. Crivello in Advances in Polymer Science 62, 1-48, (1984). For example, the desired sulfonium salts can be prepared by reaction of an aryl compound with sulfur monochloride in the presence of chlorine and a Lewis acid, reaction of an aryl Grignard reagent with a diaryl sulfoxide, condensation of a diaryl sulfoxide with an aryl compound in the presence of an acid, or the reaction of a diaryl sulfide with a diaryliodonium salt in the presence of a copper(II) salt. The person skilled in the art is well aware of the appropriate reactions as well as of the reaction conditions which have to be taken.

The compounds of the formula I can be used as photosensitive acid donors.

Subject of the invention therefore is a composition comprising (a) a compound which cures upon the action of an acid or a compound whose solubility is increased upon the action of an acid; and (b) at least one compound of the formula I as described above.

The compounds of the formula I can be used as photosensitive acid donors in a photoresist. They optionally also function as a compound whose solubility is increased upon the action of an acid, that is as part of component (a) as defined above. Resist systems can be prepared by image-wise irradiation of systems comprising compounds of formula I followed by a developing step.

The invention accordingly relates to a chemically amplified photoresist composition comprising
(a) a compound which cures upon the action of an acid; or a compound whose solubility is increased upon the action of an acid; and
(b) as photosensitive acid donor, at least one compound of the formula I.

A chemically amplified photoresist is understood to be a resist composition wherein the radiation sensitive component provides a catalytic amount of acid which subsequently catalyses a chemical reaction of at least one acid-sensitive component of the resist. Resulting is the induction of a solubility difference between the irradiated and non-irradiated areas of the resist. Because of the catalytic nature of this process one acid molecule can trigger reactions at multiple sites as it diffuses through the reactive polymer matrix, from one reaction site to the next, as long as it is not trapped or destroyed by any secondary reaction. Therefore, a small acid concentration is sufficient to induce a high difference in the solubility between exposed and unexposed areas in the resist. Thus, only a small concentration of the latent acid compound is necessary. As a result, resists with high contrast and high transparency at the exposure wavelength in optical imaging can be formulated, which in turn produce steep, vertical image profiles at high photosensitivity. However, as a result of this catalytic process, it is required that the latent acid catalysts are chemically and thermally very stable (as long as not irradiated) in order not to generate acid during resist storage or during processing, which—in most cases—requires a post exposure bake step to start or to complete the catalytic reaction which leads to the solubility differential. It is also required to have good solubility of the latent catalysts in the liquid resist formulation and the solid resist film to avoid any particle generation which would interfere with the application of these resists in microelectronic manufacturing processes.

In contrast, positive resist materials which are not based on the chemical amplification mechanism must contain a high concentration of the latent acid, because it is only the acid concentration which is generated from the latent acid under exposure which contributes to the increased solubility of the exposed areas in alkaline developer. Because small acid concentration has only a little effect on the change of the dissolution rate of such resist and the reaction proceeds typically without a post exposure bake here, the requirements regarding chemical and thermal stability of the latent acid are less demanding than for chemically amplified positive resists. These resists require also a much higher exposure dose to generate enough acid for achieving sufficient solubility in the alkaline developer in the exposed areas and also suffer from the relatively low optical transparency (due to the high concentration of latent acid necessary) and thus also lower resolution and sloped images. Resist compositions based on non-chemically amplified technology are therefore inferior in photosensitivity, resolution and image quality compared to chemically amplified resists.

From the above it becomes clear that chemical and thermal stability of a latent catalyst is vital for a chemically amplified resist and that latent acids which can work in a non-chemically amplified resist are not necessarily applicable to chemically amplified resists because of the different acid diffusion requirements, acid strength requirements and thermal and chemical stability requirements.

The difference in resist solubility between irradiated and non-irradiated sections that occurs as a result of the acid-catalysed reaction of the resist material during or after irradiation of the resist may be of two types depending upon which further constituents are present in the resist. If the compositions according to the invention comprise components that increase the solubility of the composition in the developer after irradiation, the resist is positive.

The invention accordingly relates to a chemically amplified photoresist composition, which is a positive resist.

If, on the other hand, the components of the formulation reduce the solubility of the composition after irradiation, the resist is negative.

The invention accordingly relates also to a chemically amplified photoresist composition, which is a negative photoresist.

A monomeric or polymeric compound which—in the unexposed areas—reduces the dissolution rate of an additionally present alkaline soluble binder resin in the resist formulation and which is essentially alkali-insoluble in the unexposed areas so that the resist film remains in the unexposed area after development in alkaline solution, but which is cleaved in the presence of acid, or is capable of being rearranged, in such a manner that its reaction product becomes soluble in the alkaline developer is referred to hereinafter as dissolution inhibitor.

The invention includes, as a special embodiment a chemically amplified positive alkaline-developable photoresist composition, comprising
(a1) at least one polymer having acid-labile groups which decompose in the presence of an acid and increase the solubility of the resist film in an aqueous alkaline developer solution in the exposed area and
(b) at least one compound of formula I.

A further embodiment of the invention is a chemically amplified positive alkaline-developable photoresist composition, comprising
(a2) at least one monomeric or oligomeric dissolution inhibitor having at least one acid-labile group which decomposes in the presence of acid and increases the solubility in an aqueous alkaline developer solution and at least one alkali-soluble polymer and,
(b) at least one compound of formula I.

Another specific embodiment of the invention resides in a chemically amplified positive alkaline-developable photoresist composition, comprising
(a1) at least one polymer having acid labile groups which decompose in the presence of an acid and increase the solubility in an alkaline developer in the exposed area;
(a2) a monomeric or oligomeric dissolution inhibitor, having at least one acid labile group, which decomposes in the presence of an acid and increase the alkaline solubility in the exposed area;
(a3) an alkali-soluble monomeric, oligomeric or polymeric compound at a concentration which still keeps the resist film in the unexposed area essentially insoluble in the alkaline developer, and
(b) at least one compound of formula I.

The invention therefore pertains to a chemically amplified positive photoresist composition, comprising as component
(a) at least one component selected from the group consisting of (a1), (a2) and (a3), wherein
(a1) is a polymer having an acid-labile group which decomposes in the presence of an acid to increase the solubility in aqueous alkaline developer solution;
(a2) is a monomeric or oligomeric dissolution inhibitor having an acid-labile group which decomposes in the presence of an acid to increase the solubility in aqueous alkaline developer solution; and
(a3) is an alkali-soluble monomeric, oligomeric or polymeric compound; and
(b) as photosensitive acid donor, at least one compound of formula I as defined above.

The compositions may comprise additionally to the component (b) other photosensitive acid donors and/or (c) other additives.

Such chemically amplified positive resist systems are described, for example, in E. Reichmanis, F. M. Houlihan, O. Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139.

Suitable examples of acid-labile groups which decompose in the presence of an acid to produce aromatic hydroxy groups, carboxylic groups, keto groups and aldehyde groups and increase the solubility in aqueous alkaline developer solution are, for example, alkoxyalkyl ether groups, tetrahydrofuranyl ether groups, tetrahydropyranyl ether groups, tert.-alkyl ester groups, trityl ether groups, silyl ether groups, alkyl carbonate groups as for example tert.-butyloxycarbonyloxy-, trityl ester groups, silyl ester groups, alkoxymethyl ester groups, cumyl ester groups, acetal groups, ketal groups, tetrahydropyranyl ester groups, tetrafuranyl ester groups, tertiary alkyl ether groups, tertiary alkyl ester groups, and the like. Examples of such group include alkyl esters such as methyl ester and tert-butyl ester, acetal type esters such as methoxymethyl ester, ethoxymethyl enter, 1-ethoxyethyl ester, 1-isobutoxyethyl ester, 1-isopropoxyethyl ester, 1-ethoxypropyl ester, 1-(2-methoxyethoxy)ethyl ester, 1-(2-acetoxyethoxy)ethyl ester, 1-[2-(1-adamantyloxy)ethoxy]ethyl ester, 1-[2-(1-adamantylcarbonyloxy)ethoxy]ethyl ester, tetrahydro-2-furyl ester and tetrahydro-2-pyranyl ester, and alicyclic ester such as isobornyl ester.

The polymer having functional groups capable of decomposing by the action of an acid to enhance solubility of the resist film comprising this polymer in an alkaline developing solution, which can be incorporated in the positive resist according to the present invention, may have the acid-labile groups in the backbone and/or side chains thereof, preferably in side chains thereof.

The polymer having acid-labile groups suitable for the use in the present invention can be obtained with a polymer analogous reaction where the alkaline soluble groups are partially or completely converted into the respective acid labile groups or directly by (co)-polymerization of monomers which have the acid labile groups already attached, as is for instance disclosed in EP254853, EP878738, EP877293, JP02-025850a, JP03-223860a, and JP04-251259a.

The polymers which have acid labile groups pendant to the polymer backbone, in the present invention preferably are polymers which have, for example silylether, acetal, ketal and alkoxyalkylester groups (called "low-activation energy blocking groups") which cleave completely at relatively low post exposure bake temperatures (typically between room temperature and 110° C.) and polymers which have, for example, tert-butylester groups or tert.-butyloxycarbonyl (TBOC) groups or other ester groups which contain a secondary or tertiary carbon atom next to the oxygen atom of the ester bond (called "high-activation energy blocking groups") which need higher bake temperatures (typically >110° C.) in order to complete the deblocking reaction in the presence of acid. Hybrid systems can also be applied, wherein, both, high activation energy blocking groups as well as low activation energy blocking groups are present within one polymer. Alternatively, polymer blends of polymers, each utilizing a different blocking group chemistry, can be used in the photosensitive positive resist compositions according to the invention.

Preferred polymers which have acid labile groups are polymers and co-polymers comprising the following distinct monomer types:
1) monomers that contain acid-labile groups which decompose in the presence of an acid to increase the solubility in aqueous alkaline developer solution and
2) monomers that are free of acid labile groups and free of groups that contribute to the alkaline solubility and/or
3) monomers that contribute to aqueous alkaline solubility of the polymer.

Examples of monomers of type 1) are:
non-cyclic or cyclic secondary and tertiary-alkyl(meth)acrylates such as butyl acrylate, including t-butyl acrylate, butyl methacrylate, including t-butyl methacrylate, 3-oxocyclohexyl(meth)acrylate, tetrahydropyranyl(meth)acrylate, 2-methyl-adamantyl(meth)acrylate, cyclohexyl(meth)acrylate, norbornyl(meth)acrylate, (2-tetrahydropyranyl)oxynorbonylalcohol acrylates, (2-tetrahydropyranyl)oxymethyltricyclododecanemethanol methacrylates, trimethylsilylmethyl (meth)acrylate, (2-tetrahydropyranyl)oxynorbonylalcohol acrylates, (2-tetrahydropyranyl)oxymethyltricyclododecanemethanol methacrylates, trimethylsilylmethyl(meth) acrylate o-/m-/p-(3-oxocyclohexyloxy)styrene, o-/m-/p-(1-methyl-1-phenylethoxy)styrene, o-/m-/p-tetrahydropyranyloxystyrene, o-/m-/p-adamantyloxystyrene, o-/m-/p-cyclohexyloxystyrene, o-/m-/p-norbornyloxystyrene, non-cyclic or cyclic alkoxycarbonylstyrenes such as o-/m-/p-butoxycarbonylstyrene, including p-t-butoxycarbonylstyrene, o-/m-/p-(3-oxocyclohexyloxycarbonyl)-styrene, o-/m-/p-(1-methyl-1-phenylethoxycarbonyl)styrene, o-/m-/p-tetrahydropyranyloxycarbonylstyrene, o-/m-/p-adamantyloxycarbonylstyrene, o-/m-/p-cyclohexyloxycarbonylsyrene, o-/m-/p-norbornyloxycarbonylstyrene, non-cyclic or cyclic alkoxycarbonyloxystyrenes such as o-/m-/p-butoxycarbonyloxystyrene, including p-t-butoxycarbonyloxystyrene, o-/m-/p-(3-oxocyclohexyloxycarbonyloxy)styrene, o-/m-/p-(1-methyl-1-phenylethoxycarbonyloxy)styrene, o-/m-/p-tetrahydropyranyloxycarbonyloxystyrene, o-/m-/p-adamantyloxycarbonyloxystyrene, o-/m-/p-cyclohexyloxycarbonyloxystyrene, o-/m-/p-norbornyloxycarbonyloxystyrene, non-cyclic or cyclic alkoxycarbonylalkoxystyrenes such as o/m/p-butoxycarbonylmethoxystyrene, p-t-butoxycarbonylmethoxystyrene, o-/m-/p-(3-oxocyclohexyloxycarbonylmethoxy)styrene, o-/m-/p-(1-methyl-1-phenylethoxycarbonylmethoxy)styrene, o-/m-/p-tetrahydropyranyloxycarbonylmethoxystyrene, o-/m-/p-adamantyloxycarbonylmethoxystyrene, o-/m-/p-cyclohexyloxycarbonylmethoxystyrene, o-/m-/p-norbornyloxycarbonylmethoxystyrene, trimethylsiloxystyrene, dimethyl(butyl)siloxystyrene, unsaturated alkyl acetates such as isopropenyl acetate and the derivatives of thereof.

Monomers of type 1) bearing low activation energy acid labile groups include, for example, p- or m-(1-methoxy-1-methylethoxy)-styrene, p- or m-(1-methoxy-1-methylethoxy)-methylstyrene, p- or m-(1-methoxy-1-methylpropoxy)styrene, p- or m-(1-methoxy-1-methylpropoxy) methylstyrene, p- or m-(1-methoxyethoxy)-styrene, p- or m-(1-methoxyethoxy)-methylstyrene, p- or m-(1-ethoxy-1-methylethoxy)styrene, p- or m-(1-ethoxy-1-methylethoxy)-methylstyrene, p- or m-(1-ethoxy-1-methylpropoxy)styrene, p- or m-(1-ethoxy-1-methylpropoxy)-methylstyrene, p- or m-(1-ethoxyethoxy)styrene, p- or m-(1-ethoxyethoxy)-methylstyrene, p-(1-ethoxyphenyl-ethoxy)styrene, p- or m-(1-n-propoxy-1-metylethoxy)styrene, p- or m-(1-n-propoxy-1- metylethoxy)-methylstyrene, p- or m-(1-n-propoxyethoxy) styrene, p- or m-(1-n-propoxyethoxy)-methylstyrene, p- or m-(1-isopropoxy-1-methylethoxy)styrene, p- or m-(1-isopropoxy-1-methylethoxy)-methylstyrene, p- or m-(1-isopropoxyethoxy)styrene, p- or m-(1-isopropoxyethoxy)-methylstyrene, p- or m-(1-isopropoxy-1-methylpropoxy)styrene, p- or m-(1-isopropoxy-1-methylporpoxy)-methylstyrene, p- or m-(1-isopropoxypropoxy)styrene, p- or m-(1-isopropoxyporpoxy)-methylstyrene, p- or m-(1-n-butoxy-1-methylethoxy)styrene, p- or m-(1-n-butoxyethoxy)styrene, p- or m-(1-isobutoxy-1-methylethoxy)styrene, p- or m-(1-tertbutoxy-1-methylethoxy)styrene, p- or m-(1-n-pentoxy-1-methylethoxy)styrene, p- or m-(1-isoamyloxy-1-methylethoxy) styrene, p- or m-(1-n-hexyloxy-1-methylethoxy)styrene, p- or m-(1-cyclohexyloxy-1-methylethoxy)styrene, p- or m-(1-trimethylsilyloxy-1-methylethoxy)-styrene, p- or m-(1-trimethylsilyloxy-1-methylethoxy)-methylstyrene, p- or m-(1-benzyloxy-1-methylethoxy)styrene, p- or m-(1-benzyloxy-1-methylethoxy)-methylstyrene, p- or m-(1-methoxy-1-methylethoxy)styrene, p- or m-(1-methoxy-1-methylethoxy)-methylstyrene, p- or m-(1-trimethylsilyloxy-1-methylethoxy)styrene p- or m-(1-trimethylsilyloxy-1-methylethoxy)-methylstyrene. Other examples of polymers having alkoxyalkylester acid labile groups are given in U.S. Pat. No. 5,225,316 and EP829766. Examples of polymers with acetal blocking groups are given in U.S. Pat. No. 5,670, 299, EP780732, U.S. Pat. No. 5,627,006, U.S. Pat. No. 5,558, 976, U.S. Pat. No. 5,558,971, U.S. Pat. No. 5,468,589, EP704762, EP762206, EP342498, EP553737 and described in ACS Symp. Ser. 614, Microelectronics Technology, pp. 35-55 (1995) and J. Photopolymer Sci. Technol. Vol. 10, No. 4 (1997), pp. 571-578. The polymer used in the present invention is not limited thereto.

With respect to polymers having acetal groups as acid-labile groups, it is possible to incorporate acid labile crosslinks as for example described in H.-T. Schacht, P. Falcigno, N. Muenzel, R. Schulz, and A. Medina, ACS Symp. Ser. 706 (Micro- and Nanopatterning Polymers), p. 78-94, 1997; H.-T. Schacht, N. Muenzel, P. Falcigno, H. Holzwarth, and J. Schneider, J. Photopolymer Science and Technology, Vol. 9, (1996), 573-586. This crosslinked system is preferred from the standpoint of heat resistance of the resist patterns.

Monomers with high activation energy acid labile groups are, for example, p-tert.-butoxycarbonyloxystyrene, tert.-butyl-acrylate, tert.-butyl-methacrylate, 2-methyl-2-adamantyl-methacrylate, isobornyl-methacrylate.

Monomers of type 1) suitable for ArF resist technology in particular include, for example, 2-methyl-2-adamantyl acrylate, 2-ethyl-2-adamantyl acrylate, 2-n-butyl-2-adamantyl acrylate, 2-n-butyl-2-adamantyl methacrylate, 2-methyl-2-adamantyl methacrylate, 2-ethyl-2-adamantyl methacrylate2-(1-adamantyl)isopropyl methacrylate, 2-(1-adamantyl) isopropyl acrylate, 2-(1-adamantyl)isobutyl methacrylate, 2-(1-adamantyl)isobutyl acrylate, t-butyl methacrylate, t-butyl acrylate, 1-methylcyclohexyl methacrylate, 1-methylcyclohexyl acrylate, 1-ethylcyclohexyl methacrylate, 1-ethylcyclohexyl acrylate, 1-(n-propyl)cyclohexyl methacrylate, 1-(n-propyl)cyclohexyl acrylate, tetrahydro-2-methacryloyloxy-2H-pyran and tetrahydro-2-acryloyloxy-2H-pyran. Other monomers comprising acid-labile adamantyl moieties are disclosed in JP2002-1265530A, JP2002-338627A, JP2002-169290A, JP2002-241442A, JP2002-145954A, JP2002-275215A, JP2002-156750A, JP2002-268222A, WO02/06901, JP2002-169292A, JP2002-162745A, JP2002-301161 A, JP2002-311590A, JP2002-182393A, JP2002-371114A, JP2002-162745A.

Particular olefins with acid labile-group are also suitable for ArF resist technology as shown in, for example, JP2002-308938A, JP2002-308869A, JP2002-206009A, JP2002-179624A, JP2002-161116A.

Examples of comonomers according to type 2) are: aromatic vinyl monomers, such as styrene, α-methylstyrene, acetoxystyrene, α-methylnaphthylene, acenaphthylene, vinyl alicyclic compounds such as vinyl norbornane, vinyl adamantine. vinyl cyclohexane, alkyl(meth)acrylates such as methyl methacrylate, (meth)-acrylonitrile, vinylcyclohexane, vinylcyclohexanol, itaconic anhydride, as well as maleic anhydride.

Comonomers according to type 2) suitable for ArF resist technology in particular include, for example, alpha-acryloyloxy-gamma-butyrolactone, alpha-methacryloyloxy-gamma-butyro-lactone, alpha-acryloyloxy-beta,beta-dimethyl-gamma-butyro-lactone, alpha-methacryloyl-oxy-beta, beta-dimethyl-gamma-butyrolactone, alpha-acryloyloxy-alpha-methyl-gamma-butyrolactone, alpha-methacryloyloxy-alpha-methyl-gamma-butyrolactone, beta-acryloyloxy-gamma,beta-methacryloyloxy-alpha-methyl-gamma-butyrolactone, 5-acryloyloxy-2,6-norbornanecarbolactone, 5-methacryloyloxy-2,6-norbolnanecarbolactone, 2-norbornene, methyl 5-norbornene-2-carboxylate, tert-butyl 5-norbornene-2-carboxylate, 1-cyclohexyl-1-methyl-ethyl 5-norbornene-2-carboxylate, 1-(4-methylcyclohexyl)-1-methylethyl 5-norbornene-2-carboxylate, 1-methyl-1-(4-oxocyclohexyl)ethyl 5-norbornene-2-carboxylate, 1-(1-adamatyl)-1-methylethyl 5-norbornene-2-carboxylate, 1-methylcyclohexyl 5-norbornene-2-carboxylate, 2-methyl-2-adamantyl 5-norbornene-2-carboxylate, 2-ethy-2-adamantyl 5-norbornene-2-carboxylate, 5-norbornene-2,3-dicarboxylic acid anhydrate, 2(5H)-furanone, 3-vinyl-gamma-butyrolactone, 3-methacryloyloxybicyclo[4,3,0]nonane, 3-acryloyloxybicyclo[4,3,0]nonane, 1-adamantyl methacrylate, 1-adamantyl acrylate, 3-methacryloyloxymethyltetra-cyclo[4,4,0,1$^{2.5}$,1$^{7.10}$]dodecane, 3-acryloyloxymethyltetracyclo[4,4,0,1$^{2.5}$,1$^{7.10}$]dodecane, 2-methacryloyloxynorbornane, 2-acryloyloxynorbornane, 2-methacryloyloxyisobornane, 2-acryloyloxyisobornane, 2-methacryloyloxymethylnorbornane, 2-acryloyloxymethyl-norbornane.

Examples of comonomers according to type 3) are: vinyl aromatic compounds such as hydroxystyrene, acrylic acid compounds such as methacrylic acid, ethylcarbonyloxystyrene and derivatives of thereof. These polymers are described, for example, in U.S. Pat. No. 5,827,634, U.S. Pat. No. 5,625,020, U.S. Pat. No. 5,492,793, U.S. Pat. No. 5,372, 912, EP660187, U.S. Pat. No. 5,679,495, EP813113 and EP831369. Further examples are crotonic acid, isocrotonic acid, 3-butenoic acid, acrylic acid, 4-pentenoic acid, propiolic acid, 2-butynoic acid, maleic acid, fumaric acid, and acetylenecarboxylic acid. The polymer used in the present invention is not limited thereto.

Comonomers according to type 3) suitable for ArF resist technology in particular include, for example, 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 2-hydroxy-5-norbornene, 5-norbornene-2-carboxylic acid, 1-(4-hydroxycyclohexyl)-1-methylethyl 5-norbornene-2-carboxylate, 2-hydroxy-1-ethyl 5-norbornene-2-carboxylate, 5-norbornene-2-methanol, 8-hydroxymethyl-4-methacryloyloxymethyltricyclo [5.2.1.0$^{2.6}$]decane, 8-hydroxymethyl-4-acryloyloxymethyltricyclo[5.2.1.0$^{2.6}$]decane, 4-hydroxymethyl-8-methacryloyloxy-methyltricyclo[5.2.1.0$^{2.6}$]decane, 4-hydroxymethyl-8-acryloyloxymethyltricyclo[5.2.1.0$^{2.6}$] decane.

Other monomers comprising lactone moieties suitable for ArF technology are disclosed in, for example, JP2002-006502A, JP2002-145955A, EP1127870, JP2002-357905A, JP2002-296783A. Other olefins suitable for ArF technology are published in, for example, JP2002-351078A, JP2002-234918A, JP2002-251009A, EP1127870, JP2002-328475A, JP2002-278069A, JP2003-43689A, JP2002-202604A, WO01/86353, JP2002-023371, JP2002-072484A, JP2002-202604A, JP2001-330959A, JP2002-003537A, U.S. Pat. No. 6,379,861, JP2002-30114A, JP2002-278071 A, JP2002-251011A, JP2003-122010A, U.S. Pat. No. 6,599,677, JP2002-139837A, JP2003-195504A, JP2001-264984A, JP2002-278069A, U.S. Pat. No. 6,277,538, JP2002-328475A, US2002/119391, US2003/78354.

The content of acid labile monomers in the polymer may vary over a wide range and depends on the amount of the other comonomers and the alkaline solubility of the deprotected polymer. Typically, the content of monomers with acid labile groups in the polymer is between 5 and 60 mol %. If the content is too small, too low development rates and residues of the resist in the exposed areas result. If the content of acid labile monomers is too high, resist patterns are poorly defined (eroded) after development and narrow features cannot be resolved anymore and/or the resist looses its adhesion to the substrate during development. Preferably the copolymers which have acid labile groups have a $M_W$ of from about 3'000 to about 200'000, more preferably from about 5'000 to about 50'000 with a molecular weight distribution of about 3 or less, more preferably a molecular weight distribution of about 2 or less. Non-phenolic polymers, e.g. a copolymer of an alkyl acrylate such as t-butyl acrylate or t-butyl-methacrylate and a vinyl alicyclic compound, such as a vinyl norbonanyl or vinyl cyclohexanol compound, also may be prepared by such free radical polymerization or other known procedures and suitably will have a $M_W$ of from about 8'000 to about 50'000, and a molecular weight distribution of about 3 or less.

Other comonomers may suitably be added in an appropriate amount for the purpose of controlling the glass transition point of the polymer and the like.

In the present invention a mixture of two or more polymers having acid-labile groups may be used. For example, use may be made of a mixture of a polymer having acid-labile groups, which are cleaved very easily, such as acetal groups or tetrahydropyranyloxy-groups and a polymer having acid-cleavable groups, that are less easily cleaved, such as for example tertiary alkyl ester groups. Also, acid cleavable groups of different size can be combined by blending two or more polymers having different acid cleavable groups, such as a tert-butylester group and 2-methyl-adamantyl group or an 1-ethoxy-ethoxy group and a tetrahydropyranyloxy group. A mixture of a non-crosslinked resin and a crosslinked resin may also be used. The amount of these polymers in the present invention is preferably from 30 to 99% by weight, more preferably from 50 to 98% by weight, based on the total amount of all solid components. An alkali-soluble resin or monomeric or oligomeric compound having no acid-labile groups may be further incorporated into the composition in order to control the alkali solubility.

Examples of polymer blends with polymers having different acid-labile groups are given in EP 780732, EP679951 and U.S. Pat. No. 5,817,444.

Preferably monomeric and oligomeric dissolution inhibitors (a2) are used in the present invention.

The monomeric or oligomeric dissolution inhibitor having the acid-labile group for use in the present invention is a compound which has at least one acid-labile group in the molecular structure, which decomposes in the presence of acid to increase the solubility in aqueous alkaline developer solution. Examples are alkoxymethyl ether groups, tetrahydrofuranyl ether groups, tetrahydropyranyl ether groups, alkoxyethyl ether groups, trityl ether groups, silyl ether groups, alkyl carbonate groups, trityl ester groups, silyl ester groups, alkoxymethyl ester groups, vinyl carbamate groups, tertiary alkyl carbamate groups, trityl amino groups, cumyl ester groups, acetal groups, ketal groups, tetrahydropyranyl ester groups, tetrafuranyl ester groups, tertiary alkyl ether groups, tertiary alkyl ester groups, and the like. The molecular weight of the acid-decomposable dissolution inhibitive compound for use in the present invention is 3'000 or lower, preferably from 100 to 3'000, more preferably from 200 to 2'500.

Examples of monomeric and oligomeric dissolution inhibitors having acid-labile groups are described as formulae (I) to (XVI) in EP 0831369. Other suitable dissolution inhibitors having acid-labile groups are shown in U.S. Pat. No. 5,356,752, U.S. Pat. No. 5,037,721, U.S. Pat. No. 5,015,554, JP01-289946A, JP01-289947A, JP02-002560A, JP03-128959A, JP03-158855A, JP03-179353A, JP03-191351A, JP03-200251A, JP03-200252A, JP03-200253A, JP03-200254A, JP03-200255A, JP03-259149A, JP03-279958A, JP03-279959A, JP04-001650A, JP04-001651A, JP04-011260A, JP04-012356A, JP04-123567A, JP04-271349A, JP05-045869A, JP05-158233A, JP05-257275A, JP05-297581A, JP05-297583A, JP05-303197A, JP05-303200A, JP05-341510A and JP06-080913A.

The composition can also contain polymeric dissolution inhibitors, for example, polyacetals as described for example in U.S. Pat. No. 5,354,643 or poly-N,O-acetals for example those described in U.S. Pat. No. 5,498,506, either in combination with an alkaline soluble polymer, or in combination with a polymer containing acid labile groups which increase the solubility of the resist film in the developer after exposure, or with a combination of both types of polymers.

In the case where the dissolution inhibitor having acid-labile groups is used in the present invention in combination with the compounds of formula I, the alkali-soluble polymer and/or the polymer having acid-labile groups, the amount of the dissolution inhibitor is from 3 to 55% by weight, preferably from 5 to 45% by weight, most preferably from 10 to 35% by weight, based on the total amount of all solid components of the photosensitive composition.

A polymer soluble in an aqueous alkali solution (a3) is preferably used in the present invention. Examples of these polymers include novolak resins, hydrogenated novolak resins, acetone-pyrogallol resins, poly(o-hydroxystyrene), poly(m-hydroxystyrene), poly(p-hydroxystyrene), hydrogenated poly(hydroxystyrene)s, halogen- or alkyl-substituted poly(hydroxystyrene)s, hydroxystyrene/N-substituted maleimide copolymers, o/p- and m/p-hydroxystyrene copolymers, partially o-alkylated poly(hydroxystyrene)s, [e.g., o-methylated, o-(1-methoxy)ethylated, o-(1-ethoxy)ethylated, o-2-tetrahydropyranylated, and o-(t-butoxycarbonyl)methylated poly(hydroxystyrene)s having a degree of substitution of from 5 to 30 mol % of the hydroxyl groups], o-acylated poly(hydroxystyrene)s [e.g., o-acetylated and o-(t-butoxy)carbonylated poly(hydroxystyrene)s having a degree of substitution of from 5 to 30 mol % of the hydroxyl groups], styrene/maleic anhydride copolymers, styrene/hydroxystyrene copolymers, α-methylstyrene/hydroxystyrene copolymers, carboxylated methacrylic resins, and derivatives thereof. Further suitable are poly(meth)acrylic acid [e.g. poly(acrylic acid)], (meth)acrylic acid/(meth)acrylate copolymers [e.g. acrylic acid/methyl acrylate copolymers, methacrylic acid/methyl methacrylate copolymers or methacrylic acid/methyl methacrylate/t- butyl methacrylate copolymers], (meth)acrylic acid/alkene copolymers [e.g. acrylic acid/ethylene copolymers], (meth)acrylic acid/(meth)acrylamide copolymers [e.g. acrylic acid/acrylamide copolymers], (meth)acrylic acid/vinyl chloride copolymers [e.g. acrylic acid/vinyl chloride copolymers], (meth)acrylic acid/vinyl acetate copolymer [e.g. acrylic acid/vinyl acetate copolymers], maleic acid/vinyl ether copolymers [e.g. maleic acid/methyl vinyl ether copolymers], maleic acid mono ester/methyl vinyl ester copolymers [e.g. maleic acid mono methyl ester/methyl vinyl ether copolymers], maleic acid/(meth)acrylic acid copolymers [e.g. maleic acid/acrylic acid copolymers or maleic acid/methacrylic acid copolymers], maleic acid/(meth)acrylate copolymers [e.g. maleic acid/methyl acrylate copolymers], maleic acid/vinyl chloride copolymers, maleic acid/vinyl acetate copolymers and maleic acid/alkene copolymers [e.g. maleic acid/ethylene copolymers and maleic acid/1-chloropropene copolymers]. However, the alkali-soluble polymer for use in the present invention should not be construed as being limited to these examples.

Especially preferred alkali-soluble polymers (a3) are novolak resins, poly(o-hydroxystyrene), poly(m-hydroxystyrene), poly(p-hydroxystyrene), copolymers of the respective hydroxystyrene monomers, for example with p-vinylcyclohexanol, alkyl-substituted poly(hydroxystyrene)s, partially o- or m-alkylated and o- or m-acylated poly(hydroxystyrene)s, styrene/hydroxystyrene copolymer, and α-methylstyrene/hydroxystyrene copolymers. The novolak resins are obtained by addition-condensing one or more given monomers as the main ingredient with one or more aldehydes in the presence of an acid catalyst.

Examples of monomers useful in preparing alkaline soluble resins include hydroxylated aromatic compounds such as phenol, cresols, i.e., m-cresol, p-cresol, and o-cresol, xylenols, e.g., 2,5-xylenol, 3,5-xylenol, 3,4-xylenol, and 2,3-xylenol, alkoxyphenols, e.g., p-methoxyphenol, m-methoxyphenol, 3,5-dimethoxyphenol, 2-methoxy-4-methylphenol, m-ethoxyphenol, p-ethoxyphenol, m-propoxyphenol, p-propoxyphenol, m-butoxyphenol, and p-butoxyphenol, dialkylphenols, e.g., 2-methyl-4-isopropylphenol, and other hydroxylated aromatics including m-chlorophenol, p-chlorophenol, o-chlorophenol, dihydroxybiphenyl, bisphenol A, phenylphenol, resorcinol, and naphthol. These compounds may be used alone or as a mixture of two or more thereof. The main monomers for novolak resins should not be construed as being limited to the above examples.

Examples of the aldehydes for polycondensation with phenolic compounds to obtain novolaks include formaldehyde, p-formaldehyde, acetaldehyde, propionaldehyde, benzaldehyde, phenylacetaldehyde, α-phenylpropionaldehyde, β-phenylpropionaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, o-methylbenzaldehyde, m-methylbenzaldehyde, p-methylbenzaldehyde, p-ethylbenzaldehyde, p-n-butylbenzaldehyde, furfural, chloroacetaldehyde, and acetals derived from these, such as chloroacetaldehyde diethyl acetal. Preferred of these is formaldehyde.

These aldehydes may be used alone or in combination of two or more thereof. Examples of the acid catalyst include hydrochloric acid, sulfuric acid, formic acid, acetic acid, and oxalic acid.

The weight-average molecular weight of the thus-obtained novolak resin suitably is from 1'000 to 30'000. If the weight-average molecular weight thereof is lower than 1'000, the film reduction at unexposed parts during development is liable to be large. If the weight-average molecular weight thereof exceeds 50'000, the developing rate may be too low. The especially preferred range of the molecular weight of the novolak resin is from 2'000 to 20'000.

The poly(hydroxystyrene)s and derivatives and copolymers thereof shown above as alkali-soluble polymers other than novolak resins each have a weight-average molecular weight of 2'000 or higher, preferably from 4'000 to 200'000, more preferably from 5'000 to 50'000. From the standpoint of obtaining a polymer film having improved heat resistance, the weight-average molecular weight thereof is desirably at least 5'000 or higher.

Weight-average molecular weight in the context of the present invention is meant to be the one determined by gel permeation chromatography and calibrated for with polystyrene standard.

In the present invention the alkali-soluble polymers may be used as a mixture of two or more thereof. In the case where a mixture of an alkali-soluble polymer and the polymer having groups which decompose by the action of an acid to enhance solubility in an alkaline developing solution is used, the addition amount of the alkali-soluble polymer is preferably up to 80% by weight, more preferably up to 60% by weight, most preferably up to 40% by weight, based on the total amount of the photosensitive composition (excluding the solvent). The amount exceeding 80% by weight is undesirable because the resist pattern suffers a considerable decrease in thickness, resulting in poor images and low resolution.

In the case where an alkali-soluble polymer is used together with a dissolution inhibitor, without the polymer having groups which decompose by the action of an acid, to enhance solubility in an alkaline developing solution, the amount of the alkali-soluble polymer is preferably from 40% to 90% by weight, more preferably from 50 to 85% by weight, most preferably 60 to 80% by weight. If the amount thereof is smaller than 40% by weight, undesirable results such as reduced sensitivity are caused. On the other hand, if it exceeds 90% by weight, the resist pattern suffers a considerable decrease in film thickness, resulting in poor resolution and image reproduction.

The use of the sulfonium salt derivatives according to the invention in chemically amplified systems, which operates on the principle of the removal of a protecting group from a polymer, generally produces a positive resist. Positive resists are preferred over negative resists in many applications, especially because of their higher resolution. There is, however, also interest in producing a negative image using the positive resist mechanism, in order to combine the advantages of the high degree of resolution of the positive resist with the properties of the negative resist. This can be achieved by introducing a so-called image-reversal step as described, for example, in EP361906. For this purpose, the image-wise irradiated resist material is before the developing step treated with, for example, a gaseous base, thereby image-wise neutralizing the acid which has been produced. Then, a second irradiation, over the whole area, and thermal aftertreatment are carried out and the negative image is then developed in the customary manner.

The compounds of the formula I according to the present invention are in particular suitable as photolatent acids in the ArF resist technology, i.e. a technology using ArF excimer lasers (193 nm) for the imaging step. This technology requests the use of specific polymers/copolymers. Suitable formulations and the preparation of suitable polymer/copolymers are for example published in
*Proceeding of SPIE* 2438, 474 (1995); *Proceeding of SPIE* 3049, 44 (1997); *Proceeding of SPIE* 3333, 144 (1998); *J.*

*Photopolym. Sci. Technol.* 14, 631 (2001); *Proceeding of SPIE* 3333, 546 (1998); *J. Photopolym. Sci. Technol.* 13, 601 (2000); JP2001-242627A; JP2001-290274A; JP2001-235863A; JP2001-228612A; *Proceeding of SPIE* 3333, 144 (1998); JP2001-5184A, commercially available as Lithomax alpha-7K from Mitsubishi Rayon; JP2001-272783A; U.S. patent application Ser. No. 09/413,763 (filed 1999.10.7); EP1091249; JP2000-292917A; JP2003-241385A; *J. Photopolym. Sci. Technol.* 14, 631 (2001); *Proceeding of SPIE* 3333, 11 (1998); ACS 1998 (University of Texas); JP2001-290274A; JP2001-235863A; JP2001-228612A; *Proceeding of SPIE* 3999, 13 (2000); JP2001-296663A; U.S. patent application Ser. No. 09/567,814 (filed 2000.5.9); EP1128213; *Proceeding of SPIE* 3049, 104 (1997); *J. Photopolym. Sci. Technol.* 10, 521 (1997); JP2001-290274A; JP2001-235863A; JP2001-228612A; *Proceeding of SPIE* 4345, 680 (2001); *J. Vac. Sci. Technol. B* 16(6), p. 3716, 1998; *Proceeding of SPIE* 2724, 356 (1996); *Proceeding of SPIE* 4345, 67 (2001); *Proceeding of SPIE* 3333, 546 (1998); *Proceeding of SPIE* 4345, 87 (2001); *Proceeding of SPIE* 4345, 159 (2001); *Proceeding of SPIE* 3049, 92 (1997); *Proceeding of SPIE* 3049, 92 (1997); *Proceeding of SPIE* 3049, 92 (1997); *Proceeding of SPIE* 3999, 2 (2000); *Proceeding of SPIE* 3999, 23 (2000); *Proceeding of SPIE* 3999, 54 (2000); *Proceeding of SPIE* 4345, 119 (2001).

The formulations disclosed in the aforementioned publications are incorporated herein by reference. It is understood, that the compounds of the present invention are in particular suitable for use as photolatent acid in all the polymers/copolymers and compositions described in these cited publications.

The compounds of the formula I according to the present invention are suitable as photolatent acids in the bi-layer resist. This technology requests the use of specific polymers/copolymers. Suitable formulations and the preparation of suitable polymer/copolymers are for example published in Proc. SPIE 4345, 361-370 (2001), Proc. SPIE 4345, 406-416 (2001), JP2002-278073A, JP2002-030116A, JP2002-030118A, JP2002-072477A, JP2002-348332A, JP2003-207896A, JP2002-082437A, US2003/65101, US2003/64321.

The compounds of the formula I according to the present invention are suitable as photolatent acids in the multi-layer resist. This technology requests the use of specific polymers/copolymers. Suitable formulations and the preparation of suitable polymer/copolyers are for example published in JP2003-177540A, JP2003-280207A, JP2003-149822A, JP2003-177544A.

In order to make fine hole pattern, thermal flow process or chemical shrink technology, so-called RELACS (resolution enhancement lithography assisted by chemical shrink) process, are applied for chemically amplified resist. The compounds of the formula I according to the present invention are suitable as photolatent acids in the resists for thermal flow process or RELACS process. These technologies request the use of specific polymers/copolymers. Suitable formulations and the preparation of suitable polymer/copolymers are for example published in JP2003-167357A, JP2001-337457A, JP2003-066626A, US2001/53496, *Proceeding of SPIE* 5039, 789 (2003), *IEDM*98, *Dig.*, 333 (1998), *Proceeding Silicon Technology* 11, 12 (1999), The compounds of the formula I according to the present invention are suitable as photolatent acids in the $F_2$ resist technology, i.e. a technology using $F_2$ excimer lasers (157 nm) for the imaging step. This technology requests the use of specific polymers/copolymers which have high transparency at 157 nm. Examples of polymer suitable for this application are fluoropolymers described in, for example, Proc. SPIE 3999, 330-334 (2000), Proc. SPIE 3999, 357-364 (2000), Proc. SPIE 4345, 273-284 (2001), Proc. SPIE 4345, 285-295 (2001), Proc. SPIE 4345, 296-307 (2001), Proc. SPIE 4345, 327-334 (2001), Proc. SPIE 4345, 350-360 (2001), Proc. SPIE 4345, 379-384 (2001), Proc. SPIE 4345, 385-395 (2001), Proc. SPIE 4345, 417-427 (2001), Proc. SPIE 4345, 428-438 (2001), Proc. SPIE 4345, 439-447 (2001), Proc. SPIE 4345, 1048-1055 (2001), Proc. SPIE 4345, 1066-1072 (2001), Proc. SPIE 4690, 191-199 (2002), Proc. SPIE 4690, 200-211 (2002), Proc. SPIE 4690, 486-496 (2002), Proc. SPIE 4690, 497-503 (2002), Proc. SPIE 4690, 504-511 (2002), Proc. SPIE 4690, 522-532 (2002), US2002/0031718, US2002/0051938, US2002/0055060, US2002/0058199, US 2002/0102490, US2002/0146639, US2003/0003379, US2003/0017404, WO02/021212, WO 02/073316, WO03/006413, JP2001-296662A, JP2001-350263A, JP2001-350264A, JP2001-350265A, JP2001-356480A, JP2002-60475A, JP2002-090996A, JP2002-090997A, JP2002-155112A, JP2002-155118A, JP2002-155119A, JP2002-303982A, JP2002-327013A, JP2002-363222A, JP2003-002925A, JP2003-015301 A, JP2003-177539A, JP2003-192735A, JP2002-155115A, JP2003-241386A, JP2003-255244A, US2003/36016, US2002/81499. Other suitable polymer for $F_2$ resist is silicon-containing polymers described in, for example, Proc. SPIE 3999, 365-374 (2000), Proc. SPIE 3999, 423-430 (2000), Proc. SPIE 4345, 319-326 (2001), US20020025495, JP2001-296664A, JP2002-179795A, JP2003-20335A, JP2002-278073A, JP2002-055456A, JP2002-348332A. Polymers containing (meth) acrylonitrile monomer unit described in, for example, JP2002-196495A is also suitable for $F_2$ resist.

The compounds of the formula I according to the present invention are suitable as photolatent acids in the EUV resist, i.e. a technology using light source of extreme ultra violet (13 nm) for the imaging step. This technology requests the use of specific polymers/copolymers. Suitable formulations and the preparation of suitable polymer/copolymers are for example published in JP2002-055452A, JP2003-177537A, JP2003-280199A, JP2002-323758A, US2002/51932.

The compounds of the formula I according to the present invention are suitable as photolatent acids in the EB (electron beam) or X-ray resist, i.e. a technology using EB or X-ray for the imaging step. These technologies request the use of specific polymers/copolymers. Suitable formulations and the preparation of suitable polymer/copolymers are for example published in JP2002-099088A, JP2002-099089A, JP2002-099090A, JP2002-244297A, JP2003-005355A JP2003-005356A, JP2003-162051A, JP2002-278068A, JP2002-333713A, JP2002-031892A.

The compounds of the formula I according to the present invention are suitable as photolatent acids in the chemically amplified resist for immersion lithography. This technology reduces minimum feature size of resist pattern using liquid medium between the light source and the resist as described in *Proceeding of SPIE* 5040, 667 (2003), *Proceeding of SPIE* 5040, 679 (2003), *Proceeding of SPIE* 5040, 690 (2003), *Proceeding of SPIE* 5040, 724 (2003).

The compounds of the formula I according to the present invention are suitable as photolatent acids in the positive and negative photosensitive polyimide. This technology requests the use of specific polymers/copolymers. Suitable formulations and the preparation of suitable polymer/copolymers are for example published in JP09-127697A, JP10-307393A, JP10-228110A, JP10-186664A, JP11-338154A, JP11-315141A, JP11-202489A, JP11-153866A, JP11-084653A, JP2000-241974A, JP2000-221681A, JP2000-034348A, JP2000-034347A, JP2000-034346A, JP2000-026603A, JP2001-290270A, JP2001-281440A, JP2001-264980A, JP2001-255657A, JP2001-214056A, JP2001-214055A, JP2001-166484A, JP2001-147533A, JP2001-125267A, JP2001-83704A, JP2001-066781A, JP2001-056559A, JP2001-033963A, JP2002-356555A, JP2002-356554A, JP2002-303977A, JP2002-284875A, JP2002-268221A, JP2002-162743A, JP2002-122993A, JP2002-099084A, JP2002-040658A, JP2002-037885A, JP2003-026919A.

The formulations disclosed in the aforementioned publications are incorporated herein by reference. It is understood, that the compounds of the present invention are in particular suitable for use as photolatent acid in all the polymers/copolymers and compositions described in these cited publications.

The difference in resist solubility between irradiated and non-irradiated sections that occurs as a result of the reaction of the resist material by an acid during or after irradiation of the resist may be of two types depending upon which further constituents are present in the resist. If the compositions according to the invention comprise components that decrease the solubility of the composition in the developer after irradiation, the resist is negative.

Subject of the invention also is a chemically amplified negative photoresist composition.

The invention includes, as a special embodiment a chemically amplified negative alkaline-developable photoresist composition, comprising
(a4) an alkali-soluble resin as binder;
(a5) a component which is cationically or acid-catalytically polymerizable or cross-linkable with itself and/or with the other components; and
(b) at least one compound of formula I.

A further embodiment of the invention is a chemically amplified negative alkaline-developable photoresist composition, comprising
(a5) a component which is cationically or acid-catalytically polymerizable or cross-linkable with itself and/or with the other components; and
(b) at least one compound of formula I.

The subject composition includes, as a special embodiment, chemically amplified negative solvent-developable photoresists, comprising
(a5) a component which is cationically or acid-catalytically polymerizable or cross-linkable with itself and/or with the other components; and
(b) at least one compound of formula I.

Another specific embodiment of the invention resides in a chemically amplified negative solvent-developable photoresist composition, comprising
(a5) a component which is cationically or acid-catalytically polymerizable or cross-linkable with itself and/or with the other components;
(a6) a solvent-developable resin as binder; and
(b) at least one compound of formula I.

The composition may comprise additionally to the component (b) other photosensitive acid donors (b1), other photoinitiators (d), sensitizere (e) and/or other additives (c).

The invention also pertains to a chemically amplified negative photoresist composition, comprising as component (a) at least one component selected from the group consisting of (a4), (a5) and (a6), wherein
(a4) is an alkali-soluble resin as binder;
(a6) is a solvent-developable resin as binder;
(a5) is a component which is cationically or acid-catalytically polymerizable or cross-linkable with itself and/or with the other components; and
(b) as photosensitive acid donor, at least one compound of the formula I as defined above.

The composition may comprise additionally to the components (a) and (b), or components (a1), (a2), (a3) and (b), or components (a4), (a5), (a6) and (b), further additives (c), further photosensitive acid donor compounds (b1), other photoinitiators (d), and/or sensitizers (e).

Acid-sensitive components (a5) that produce a negative resist characteristically are especially compounds which are capable of undergoing a cationic or acid-catalytic polymerization or cross-linking reaction with themselves and/or with one or more further components of the composition by an acid (e.g. the acid formed during irradiation of the compounds of formulae I). Examples thereof include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, or mixtures thereof. Amino resins, phenolic resins and epoxy resins are very suitable. Acid-curable resins are generally known and are described, for example, in Wagner, Sarx/Lackkunstharze (Munich, 1971), pages 86 to 123 and 229 to 238, or in Ullmann/Encyclopadie der techn. Chemie, $4^{th}$ edition, volume 15 (1978), pages 613 to 628, or Ullmann's Encyclopedia of Industrial Chemistry, Verlag Chemie, 1991, Vol. 18, 360 ff., Vol. A19, 371 ff.

It is possible, for example, to use all customary epoxides, such as aromatic, aliphatic or cycloaliphatic epoxy resins. These are compounds having at least one, preferably at least two, epoxy group(s) in the molecule. Examples thereof are the glycidyl ethers and β-methyl glycidyl ethers of aliphatic or cycloaliphatic diols or polyols, e.g. those of ethylene glycol, propane-1,2-diol, propane-1,3-diol, butane-1,4-diol, diethylene glycol, polyethylene glycol, polypropylene glycol, glycerol, trimethylolpropane or 1,4-dimethylolcyclohexane or of 2,2-bis(4-hydroxycyclohexyl)propane and N,N-bis(2-hydroxyethyl)aniline; the glycidyl ethers of di- and polyphenols, for example of resorcinol, of 4,4'-dihydroxyphenyl-2,2-propane, of novolaks or of 1,1,2,2-tetrakis(4-hydroxyphenyl)ethane. Examples thereof include phenyl glycidyl ether, p-tert-butyl glycidyl ether, o-icresyl glycidyl ether, polytetrahydrofuran glycidyl ether, n-butyl glycidyl ether, 2-ethylhexylglycidylether, $C_{12/15}$alkyl glycidyl ether and cyclohexanedimethanol diglycidyl ether. Further examples include N-glycidyl compounds, for example the glycidyl compounds of ethyleneurea, 1,3-propyleneurea or 5-dimethyl-hydantoin or of 4,4'-methylene-5,5'-tetramethyldihydantoin, or compounds such as triglycidyl isocyanurate.

Further examples of glycidyl ether components (a5) that are used in the formulations according to the invention are, for example, glycidyl ethers of polyhydric phenols obtained by the reaction of polyhydric phenols with an excess of chlorohydrin, such as, for example, epichlorohydrin (e.g. glycidyl ethers of 2,2-bis(2,3-epoxypropoxyphenol)propane. Further examples of glycidyl ether epoxides that can be used in connection with the present invention are described, for example, in U.S. Pat. No. 3,018,262 and in "Handbook of Epoxy Resins" by Lee and Neville, McGraw-Hill Book Co., New York (1967).

There is also a large number of commercially available glycidyl ether epoxides that are suitable as component (a5), such as, for example, glycidyl methacrylate, diglycidyl ethers of bisphenol A, for example those obtainable under the trade names EPON 828, EPON 825, EPON 1004 and EPON 1010

(Shell); DER-331, DER-332 and DER-334 (Dow Chemical); 1,4-butanediol diglycidyl ethers of phenolformaldehyde novolak, e.g. DEN-431, DEN-438 (Dow Chemical); and resorcinol diglycidyl ethers; alkyl glycidyl ethers, such as, for example, $C_8$-$C_{10}$glycidyl ethers, e.g. HELOXY Modifier 7, $C_{12}$-$C_{14}$glycidyl ethers, e.g. HELOXY Modifier 8, butyl glycidyl ethers, e.g. HELOXY Modifier 61, cresyl glycidyl ethers, e.g. HELOXY Modifier 62, p-tert-butylphenyl glycidyl ethers, e.g. HELOXY Modifier 65, polyfunctional glycidyl ethers, such as diglycidyl ethers of 1,4-butanediol, e.g. HELOXY Modifier 67, diglycidyl ethers of neopentyl glycol, e.g. HELOXY Modifier 68, diglycidyl ethers of cyclohexanedimethanol, e.g. HELOXY Modifier 107, trimethylolethane triglycidyl ethers, e.g. HELOXY Modifier 44, trimethylolpropane triglycidyl ethers, e.g. HELOXY Modifier 48, polyglycidyl ethers of aliphatic polyols, e.g. HELOXY Modifier 84 (all HELOXY glycidyl ethers are obtainable from Shell). Also suitable are glycidyl ethers that comprise copolymers of acrylic esters, such as, for example, styrene-glycidyl methacrylate or methyl methacrylate-glycidyl acrylate. Examples thereof include 1:1 styrene/glycidyl methacrylate, 1:1 methyl methacrylate/glycidyl acrylate, 62.5:24:13.5 methyl methacrylate/ethyl acrylate/glycidyl methacrylate.

The polymers of the glycidyl ether compounds can, for example, also comprise other functionalities provided that these do not impair the cationic curing.

Other glycidyl ether compounds suitable as component (a5) that are commercially available are polyfunctional liquid and solid novolak glycidyl ether resins, e.g. PY 307, EPN 1179, EPN 1180, EPN 1182 and ECN 9699.

It will be understood that mixtures of different glycidyl ether compounds may also be used as component (a5).

The glycidyl ethers (a5) are, for example, compounds of formula XX

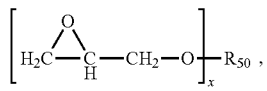

(XX)

wherein x is a number from 1 to 6; and $R_{50}$ is a mono- to hexavalent alkyl or aryl radical.

Preference is given, for example, to glycidyl ether compounds of formula XX, wherein x is the number 1, 2 or 3; and $R_{50}$ when x=1, is unsubstituted or $C_1$-$C_{12}$alkyksubstituted phenyl, naphthyl, anthracyl, biphenylyl, $C_1$-$C_{20}$alkyl, or $C_2$-$C_{20}$alkyl interrupted by one or more oxygen atoms, or $R_{50}$ when x=2, is 1,3-phenylene, 1,4-phenylene, $C_6$-$C_{10}$cycloalkylene, unsubstituted or halo-substituted $C_1$-$C_{40}$alkylene, $C_2$-$C_{40}$alkylene interrupted by one or more oxygen atoms, or a group

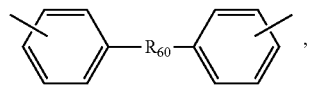

or $R_{50}$ when x=3, is a radical

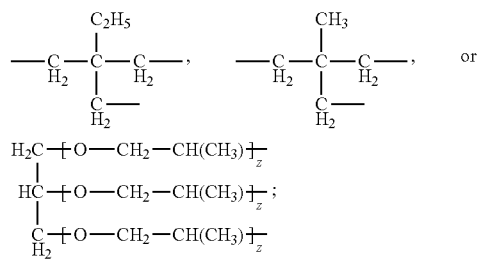

z is a number from 1 to 10; and $R_{60}$ is $C_1$-$C_{20}$alkylene, oxygen or

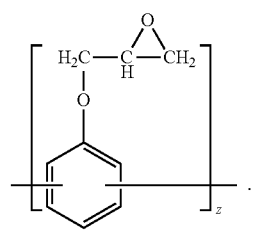

The glycidyl ethers (a5) are, for example, compounds of formula XXa

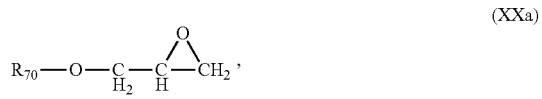

(XXa)

wherein $R_{70}$ is unsubstituted or $C_1$-$C_{12}$alkyl-substituted phenyl; naphthyl; anthracyl; biphenylyl;

$C_1$-$C_{20}$alkyl, $C_2$-$C_{20}$alkyl interrupted by one or more oxygen atoms; or a group of formula

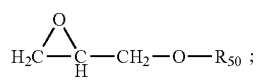

$R_{50}$ is phenylene, $C_1$-$C_{20}$alkylene, $C_2$-$C_{20}$alkylene interrupted by one or more oxygen atoms, or a group

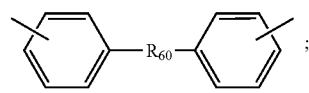

and $R_{60}$ is $C_1$-$C_{20}$alkylene or oxygen.

Preference is given to the glycidyl ether compounds of formula XXb

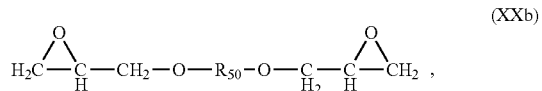

(XXb)

wherein
R$_{50}$ is phenylene, C$_1$-C$_{20}$alkylene, C$_2$-C$_{20}$alkylene interrupted by one or more oxygen atoms, or a group

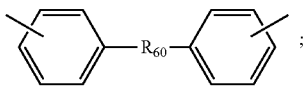

and
R$_{60}$ is C$_1$-C$_{20}$alkylene or oxygen.

Further examples for component (a5) are polyglycidyl ethers and poly(β-methylglycidyl) ethers obtainable by the reaction of a compound containing at least two free alcoholic and/or phenolic hydroxy groups per molecule with the appropriate epichlorohydrin under alkaline conditions, or alternatively in the presence of an acid catalyst with subsequent alkali treatment. Mixtures of different polyols may also be used.

Such ethers can be prepared with poly(epichlorohydrin) from acyclic alcohols, such as ethylene glycol, diethylene glycol and higher poly(oxyethylene) glycols, propane-1,2-diol and poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylol-propane, pentaerythritol and sorbitol, from cycloaliphatic alcohols, such as resorcitol, quinitol, bis(4-hydroxycyclohexyl)methane, 2,2-bis(4-hydroxycyclohexyl)propane and 1,1-bis-(hydroxymethyl)cyclohex-3-ene, and from alcohols having aromatic nuclei, such as N,N-bis(2-hydroxyethyl)aniline and p,p'-bis(2-hydroxyethylamino)diphenylmethane. They can also be prepared from mononuclear phenols, such as resorcinol and hydroquinone, and polynuclear phenols, such as bis(4-hydroxyphenyl)methane, 4,4-dihydroxydiphenyl, bis(4-hydroxyphenyl)sulphone, 1,1,2,2-tetrakis(4-hydroxyphenyl)ethane, 2,2-bis(4-hydroxyphenyl)-propane (bisphenol A) and 2,2-bis(3,5-dibromo-4-hydroxyphenyl)propane.

Further hydroxy compounds suitable for the preparation of polyglycidyl ethers and poly(β-methylglycidyl) ethers are the novolaks obtainable by the condensation of aldehydes, such as formaldehyde, acetaldehyde, chloral and furfural, with phenols, such as, for example, phenol, o-cresol, m-cresol, p-cresol, 3,5-dimethylphenol, 4-chlorophenol and 4-tert-butylphenol.

Poly(N-glycidyl) compounds can be obtained, for example, by dehydrochlorination of the reaction products of epichlorohydrin with amines containing at least two amino-hydrogen atoms, such as aniline, n-butylamine, bis(4-aminophenyl)methane, bis(4-aminophenyl)-propane, bis-(4-methylaminophenyl)methane and bis(4-aminophenyl) ether, sulphone and sulphoxide. Further suitable poly(N-glycidyl) compounds include triglycidyl isocyanurate, and N,N'-diglycidyl derivatives of cyclic alkyleneureas, such as ethyleneurea and 1,3-propyleneurea, and hydantoins, such as, for example, 5,5-dimethylhydantoin. Poly(S-glycidyl) compounds are also suitable. Examples thereof include the di-S-glycidyl derivatives of dithiols, such as ethane-1,2-dithiol and bis(4-mercaptomethylphenyl) ether.

There also come into consideration as component (a5) epoxy resins in which the glycidyl groups or β-methyl glycidyl groups are bonded to hetero atoms of different types, for example the N,N,O-triglycidyl derivative of 4-aminophenol, the glycidyl ether/glycidyl ester of salicylic acid or p-hydroxybenzoic acid, N-glycidyl-N'-(2-glycidyloxypropyl)-5,5-dimethyl-hydantoin and 2-glycidyloxy-1,3-bis(5,5-dimethyl-1-glycidylhydantoin-3-yl)propane.

Preference is given to diglycidyl ethers of bisphenols. Examples thereof include diglycidyl ethers of bisphenol A, e.g. ARALDIT GY 250, diglycidyl ethers of bisphenol F and diglycidyl ethers of bisphenol S. Special preference is given to diglycidyl ethers of bisphenol A.

Further glycidyl compounds of technical importance are the glycidyl esters of carboxylic acids, especially di- and poly-carboxylic acids. Examples thereof are the glycidyl esters of succinic acid, adipic acid, azelaic acid, sebacic acid, phthalic acid, terephthalic acid, tetra- and hexa-hydrophthalic acid, isophthalic acid or trimellitic acid, or of dimerised fatty acids.

Examples of polyepoxides that are not glycidyl compounds are the epoxides of vinyl-cyclohexane and dicyclopentadiene, 3-(3',4'-epoxycyclohexyl)-8,9-epoxy-2,4-dioxaspiro-[5.5]undecane, the 3',4'-epoxycyclohexylmethyl esters of 3,4-epoxycyclohexanecarboxylic acid, (3,4-epoxycyclohexyl-methyl 3,4-epoxycyclohexanecarboxylate), butadiene diepoxide or isoprene diepoxide, epoxidised linoleic acid derivatives or epoxidised polybutadiene.

Further suitable epoxy compounds are, for example, limonene monoxide, epoxidised soybean oil, bisphenol-A and bisphenol-F epoxy resins, such as, for example, ARALDIT® GY 250 (A), ARALDIT® GY 282 (F), ARALDIT® GY 285 (F)), and photocurable siloxanes that contain epoxy groups.

Further suitable cationically polymerisable or crosslinkable components (a5) can be found, for example, also in U.S. Pat. No. 3,117,099, U.S. Pat. No. 4,299,938 and U.S. Pat. No. 4,339,567.

From the group of aliphatic epoxides there are suitable especially the monofunctional symbol α-olefin epoxides having an unbranched chain consisting of 10, 12, 14 or 16 carbon atoms.

Because nowadays a large number of different epoxy compounds are commercially available, the properties of the binder can vary widely. One possible variation, for example depending upon the intended use of the composition, is the use of mixtures of different epoxy compounds and the addition of flexibilisers and reactive diluents.

The epoxy resins can be diluted with a solvent to facilitate application, for example when application is effected by spraying, but the epoxy compound is preferably used in the solvent-less state. Resins that are viscous to solid at room temperature can be applied hot.

Sulfonium salt derivatives can also be used as acid generators, which can be activated photochemically, for the acid-catalysed crosslinking of, for example, poly(glycidyl)-methacrylates in negative resist systems. Such crosslinking reactions are described, for example, by Chae et al. in Pollimo 1993, 17(3), 292.

Also suitable as component (a5) are all customary vinyl ethers, such as aromatic, aliphatic or cycloaliphatic vinyl ethers and also silicon-containing vinyl ethers. These are compounds having at least one, preferably at least two, vinyl ether groups in the molecule. Examples of vinyl ethers suitable for use in the compositions according to the invention include triethylene glycol divinyl ether, 1,4-cyclohexanedimethanol divinyl ether, 4-hydroxybutyl vinyl ether, the propenyl ether of propylene carbonate, dodecyl vinyl ether, tert-butyl vinyl ether, tert-amyl vinyl ether, cyclohexyl vinyl ether, 2-ethylhexyl vinyl ether, ethylene glycol monovinyl ether, butanediol monovinyl ether, hexanediol monovinyl ether, 1,4-cyclohexanedimethanol monovinyl ether, diethylene glycol monovinyl ether, ethylene glycol divinyl ether, ethylene glycol butylvinyl ether, butane-1,4-diol divinyl ether, hexanediol divinyl ether, diethylene glycol divinyl ether, triethylene glycol divinyl ether, triethylene glycol methylvinyl ether, tetra-ethylene glycol divinyl ether, pluriol-E-200 divinyl ether, polytetrahydrofuran divinyl ether-290, trimethylolpropane trivinyl ether, dipropylene glycol divinyl ether, octadecyl vinyl ether, (4-cyclohexyl-methyleneoxyethene)-glutaric acid methyl ester and (4-butoxyethene)-isophthalic acid ester.

Examples of hydroxy-containing compounds include polyester polyols, such as, for example, polycaprolactones or polyester adipate polyols, glycols and polyether polyols, castor oil, hydroxy-functional vinyl and acrylic resins, cellulose esters, such as cellulose acetate butyrate, and phenoxy resins.

Further cationically curable formulations can be found, for example, in EP119425.

As component (a5), preference is given to cycloaliphatic epoxides, or epoxides based on bisphenol A.

The formulations according to the invention can further comprise as component (a5) non-aqueous coating compositions based on an oxidatively drying alkyd resin which contains at least one, preferably two or more, functional group(s) capable of undergoing polymerisation or polycondensation reactions in the presence of an acid. Examples of such resins are vinyl-ether-functionalized alkyd resins, acetal-functionalised alkyd resins, and/or alkoxysilane-functionalized alkyd resins, as proposed, e.g., in WO99/47617. Those modified alkyd resins may be used alone or in combination with other alkyd resins. At least some of the alkyd resin composition in the non-aqueous coating is oxidatively drying as a result of the incorporation of a large number of unsaturated, aliphatic compounds, at least some of which are polyunsaturated.

Formulations containing those modified alkyd resins as component (a5) may optionally contain, in addition to the photoinitiator (d), an oxidative dryer. Suitable oxidative dryers are, for example, metal siccatives. There may be mentioned as suitable siccatives, for example, the metal salts of (cyclo)aliphatic acids, such as octanoic acid and naphthenic acid, the metals to be used being, for example, cobalt, manganese, lead, zirconium, calcium, zinc and rare earth metals. Mixtures of siccatives may be used. Preference is given to metal salts of cobalt, zirconium and calcium, or mixtures thereof. The siccatives (calculated as metal) are usually used in an amount of from 0.001 to 3% by weight.

Under certain conditions it may also be advantageous, when using the modified alkyd resins as component (a5), to use one or more mono- or bis-acylphosphine oxide photoinitiators in addition to the sulphonium salt of formula (I). Suitable monoacyl- or bisacyl-phosphine oxide photoinitiators include, for example, monoacylphosphine oxides such as (2,4,6-tri-methylbenzoyl)-diphenylphosphine oxide (DAROCUR® TPO) or (2,4,6-trimethylbenzoyl-phenylethoxy-phosphine oxide, or bisacylphosphine oxide photoinitiators such as bis(2,6-dimethoxybenzoyl)-2,4,4-trimethylpentyl-phosphine oxide, bis(2,4,6-trimethylbenzoyl)-(2,4-dipentyloxyphenyl)-phosphine oxide and bis(2,4,6-trimethylbenzoyl)phenyl-phosphine oxide (IRGACURE® 819). Those monoacyl- or bisacylphosphine oxides are advantageously used in an amount of from 0.5 to 5%.

When component (a5) contains modified alkyd resins, in addition to the photoinitiator (d) it is also possible to use an oxidative dryer and suitable monoacyl- or bisacyl-phosphine oxide photoinitiators.

The alkyd resins used as component (a5) contain a large number of unsaturated, aliphatic compounds, at least some of which are polyunsaturated. The unsaturated aliphatic compounds preferably used for the preparation of those alkyd resins are unsaturated aliphatic monocarboxylic acids, especially polyunsaturated aliphatic monocarboxylic acids.

Examples of mono-unsaturated fatty acids are myristoleic acid, palmitic acid, oleic acid, gadoleic acid, erucic acid and ricinoleic acid. Preferably fatty acids containing conjugated double bonds, such as dehydrogenated castor oil fatty acid and/or tung oil fatty acid, are used. Other suitable monocarboxylic acids include tetrahydrobenzoic acid and hydrogenated or non-hydrogenated abietic acid or the isomers thereof. If desired, the monocarboxylic acid in question may be used wholly or in part in the form of a triglyceride, e.g. as vegetable oil, in the preparation of the alkyd resin. If desired, mixtures of two or more such mono-carboxylic acids or triglycerides may be used, optionally in the presence of one or more saturated, (cyclo)aliphatic or aromatic monocarboxylic acids, e.g. pivalic acid, 2-ethyl-hexanoic acid, lauric acid, palmitic acid, stearic acid, 4-tert-butyl-benzoic acid, cyclopentanecarboxylic acid, naphthenic acid, cyclohexanecarboxylic acid, 2,4-dimethylbenzoic acid, 2-methylbenzoic acid and benzoic acid.

If desired, polycarboxylic acids may also be incorporated into the alkyd resin, such as phthalic acid, isophthalic acid, terephthalic acid, 5-tert-butylisophthalic acid, trimellitic acid, pyromellitic acid, succinic acid, adipic acid, 2,2,4-trimethyladipic acid, azelaic acid, sebacic acid, dimerised fatty acids, cyclopentane-1,2-dicarboxylic acid, cyclohexane-1,2-dicarboxylic acid, 4-methylcyclohexane-1,2-dicarboxylic acid, tetrahydrophthalic acid, endomethylene-cyclohexane-1,2-dicarboxylic acid, butane-1,2,3,4-tetracarboxylic acid, endoisopropylidene-cyclohexane-1,2-dicarboxylic acid, cyclohexane-1,2,4,5-tetracarboxylic acid and butane-1,2,3,4-tetracarboxylic acid. If desired, the carboxylic acid in question may be used as an anhydride or in the form of an ester, for example an ester of an alcohol having from 1 to 4 carbon atoms.

In addition, the alkyd resin can be composed of di- or poly-valent hydroxyl compounds. Examples of suitable divalent hydroxyl compounds are ethylene glycol, 1,3-propanediol, 1,6-hexanediol, 1,12-dodecanediol, 3-methyl-1,5-pentanediol, 2,2,4-trimethyl-1,6-hexane-diol, 2,2-dimethyl-1,3-propanediol and 2-methyl-2-cyclohexyl-1,3-propanediol. Examples of suitable triols are glycerol, trimethylolethane and trimethylolpropane. Suitable polyols having more than 3 hydroxyl groups are pentaerythritol, sorbitol and etherified products of the compounds in question, such as ditrimethylolpropane and di-, tri- and tetra-pentaerythritol.

Preferably, compounds having from 3 to 12 carbon atoms, e.g. glycerol, pentaerythritol and/or dipentaerythritol, are used.

The alkyd resins can be obtained by direct esterification of the constituents, with the option that some of those components may already have been converted into ester diols or polyester diols. The unsaturated fatty acids can also be used in the form of a drying oil, such as linseed oil, tuna fish oil, dehydrogenated castor oil, coconut oil and dehydrogenated coconut oil. The final alkyd resin is then obtained by transesterification with the other acids and diols added. The transesterification is advantageously carried out at a temperature in the range of from 115 to 250° C., optionally in the presence of solvents such as toluene and/or xylene. The reaction is advantageously carried out in the presence of a catalytic amount of a transesterification catalyst. Examples of suitable transesterification catalysts include acids, such as p-toluenesulphonic acid, basic compounds, such as an amine, or compounds such as calcium oxide, zinc oxide, tetraisopropyl orthotitanate, dibutyltin oxide and tri-phenylbenzylphosphonium chloride.

The vinyl ether, acetal and/or alkoxysilane compounds used as part of component (a5) preferably contain at least two vinyl ether, acetal and/or alkoxysilane groups and have a molecular weight of 150 or more. Those vinyl ether, acetal and/or alkoxysilane compounds can be obtained, for example, by the reaction of a commercially available vinyl ether, acetal and/or alkoxysilane compound containing a vinyl ether, acetal and/or alkoxysilane group and in addition a maximum of one functional amino, epoxy, thiol, isocyanate, acrylic, hydride or hydroxyl group, with a compound having at least two groups capable of reacting with an amino, epoxy, thiol, isocyanate, acrylic, hydride or hydroxyl group. As examples thereof there may be mentioned compounds having at least two epoxy, isocyanate, hydroxyl and/or ester groups or compounds having at least two ethylenically or ethynylenically unsaturated groups.

As component (a5), preference is given to a composition in which the vinyl ether, acetal and/or alkoxysilane compounds are covalently bonded to the alkyd resin by addition via a reactive group such as an amino, hydroxyl, thiol, hydride, epoxy and/or isocyanate group. For that purpose, the compounds must have at least one group capable of forming an adduct with the reactive groups present in the alkyd resin.

To incorporate vinyl ether groups into the alkyd resin, use is made of a vinyloxyalkyl compound, the alkyl group of which is substituted by a reactive group, such as a hydroxyl, amino, epoxy or isocyanate group, that is capable of forming an adduct with one or more of the reactive groups present in the alkyd resin.

As component (a5), preference is given to compositions in which the ratio of the number of oxidatively drying groups present in the alkyd resin to the number of groups that are reactive in the presence of an acid is in the range of from 1/10 to 15/1, especially from 1/3 to 5/1. Instead of a single modified alkyd resin, it is also possible to use a plurality of alkyd resins, with one alkyd resin being highly modified and the others being less modified or not modified at all.

Examples of vinyl ether compounds capable of being covalently bonded to the alkyd resin are ethylene glycol monovinyl ether, butanediol monovinyl ether, hexanediol monovinyl ether, triethylene glycol monovinyl ether, cyclohexanedimethanol monovinyl ether, 2-ethylhexanediol monovinyl ether, polytetrahydrofuran monovinyl ether, tetraethylene glycol monovinyl ether, trimethylolpropane divinyl ether and aminopropyl vinyl ether.

Adducts can be formed, for example, by reacting the vinyl ether compounds containing a hydroxyl group or amino group with an excess of a diisocyanate, followed by the reaction of that free-isocyanate-group-containing adduct with the free hydroxyl groups of the alkyd resin. Preferably, a process is used in which first the free hydroxyl groups of the alkyd resin react with an excess of a polyisocyanate, and then the free isocyanate groups react with an amino-group- or hydroxyl-group-containing vinyl ether compound. Instead of a diisocyanate, it is also possible to use a diester. Transesterification of the hydroxyl groups present in the alkyd resin with an excess of the diester, followed by transesterification or transamidation of the remaining ester groups with hydroxy-functional vinyl ether compounds or amino-functional vinyl ether compounds, respectively, yields vinyl-ether-functional alkyd resins. It is also possible to incorporate (meth)acrylate groups into the alkyd resin during preparation of the alkyd resin, by carrying out the preparation in the presence of a hydroxy-functional (meth)acrylate ester, such as hydroxy-ethyl methacrylate (HEMA), and then reacting the thus functionalised alkyd resin by means of a Michael reaction with a vinyl-ether-group-containing compound and a primary-amino-group-containing compound, followed by reaction with e.g. an isocyanate compound, in order to obtain a non-basic nitrogen atom.

An example of such a reaction is described, for example, in WO99/47617. Esterification of ricinine fatty acid with dipentaerythritol, followed by transesterification of the free hydroxyl groups with diethyl malonate and 4-hydroxybutyl vinyl ether in a suitable ratio, yields a vinyl-ether-functional alkyd resin suitable for use as component (a5).

For the preparation of acetal-functional alkyd resins, use is generally made of dialkyl acetal functionalised with an amino group. Examples of suitable acetal compounds include 4-aminobutyraldehyde dimethyl acetal and 4-aminobutyraldehyde diethyl acetal. The alkyd resin is modified by the addition of the aminoacetal monomer to an alkyd resin functionalised with isocyanate groups, with ester groups of a low-boiling alcohol or with (meth)acrylate groups. The resulting dialkyl-acetal-modified alkyd resin can be incorporated into the coating composition having a high solids content and low viscosity. The preparation of acetal-functional alkyd resins can also be carried out by reacting hydroxyacetal with the carboxyl groups of the alkyd resin or by reacting a diisocyanate or diester compound with the hydroxyl groups of the alkyd resin.

An example of this preparative method is described in WO99/47617, for example the esterification of a hydroxy-functional alkyd resin with diethyl malonate, followed by transamidation of the free ester group with 4-aminobutyraldehyde dimethyl acetal in a suitable ratio. The resulting acetal-modified alkyd resin is suitable as component (a5).

For the incorporation of alkoxysilane groups into the alkyd resin, use is made of a siloxane compound having one or more reactive group(s) which are subsequently reacted with one or more of the constituents making up the alkyd resin. These are, for example, alkoxy-silanes of the formula: $(E)_a\text{-}Si(R_{10})_b(R_{20})_c$, wherein $R_{10}$ is alkoxy or oxyalkylenealkoxy or, when E is hydrogen, $R_{10}$ is halogen, $R_{20}$ is an aliphatic, cycloaliphatic or aromatic group, and E is hydrogen or an alkyl group substituted by an amino, isocyanate, mercapto or epoxy group; a is from 1 to 3, b is from 1 to 3, c is from 0 to 2, and a+b+c=4.

$R_{10}$ is preferably an alkoxy group having from 1 to 4 carbon atoms in the alkoxy group, and $R_{20}$ is preferably a group having not more than 18 carbon atoms.

Examples of suitable siloxane compounds are 3-aminopropyl-triethoxysilane, polyglycol-ether-modified aminosilane, 3-aminopropyl-trimethoxysilane, 3-aminopropyltris-methoxy-ethoxyethoxysilane, 3-aminopropyl-methyl-diethoxysilane, N-2-aminoethyl-3-aminopropyl-trimethoxy-silane, N-2-aminoethyl-3-aminopropyl-methyldimethoxy-silane, N-methyl-3-aminopropyl-trimethoxysilane, 3-ureidopropyl-triethoxysilane, 3,4,5-dihydroimidazol-1-yl-propyltriethoxysilane, 3-methacryloxypropyl-trimethoxysilane, 3-glycidyloxypropyl-trimethoxysilane, 3-mercaptopropyl-trimethoxysilane and 3-mercaptopropyl-methyl-dimethoxysilane, triethoxysilane, diethoxymethylsilane, dimethoxymethylsilane, tri-methoxysilane, trichlorosilane, triiodosilane, tribromosilane, dichloromethylsilane and dibromomethylsilane.

The alkyd resin can be modified, for example, by the insertion of an amino-group-modified alkoxysilane into an alkyd resin modified with a polyisocyanate or a polyester of a low-boiling alcohol. Hydride-functional alkoxysilanes can be bonded directly to the alkyd, i.e. without modification with a binding molecule such as a diisocyanate or diester, by adding a compound containing a silylhydride group to an ethylenically unsaturated group in the alkyd resin. That addition is catalysed by a transition metal. In that process, use is preferably made of a halogenated silylhydride and, in order to terminate the addition reaction, conversion into an alkoxysilane compound with a low-boiling alcohol. The addition reaction is advantageously carried out in the absence of sterically hindering groups and proceeds in optimum manner when the ethylenically unsaturated groups are terminal groups, as is the case, for example, with esters of 10-undecenecarboxylic acid.

Examples of the preparation of alkoxysiloxane-modified alkyd resins are described in WO99/47617. Esterification of a hydroxy-functional alkyd resin with diethyl malonate, followed by transamidation of the free ester group with 3-aminopropyltriethoxysilane in a suitable ratio yields an alkoxysilane-modified alkyd resin. Hydroxy-modified alkyd resin can also be reacted with an excess of isophorone diisocyanate, followed by reaction of the free isocyanate groups with 3-aminopropyltriethoxysilane. Both alkoxysiloxane-modified alkyd resins obtained by the processes described are suitable for use in component (a5).

The sulphonium salt compounds of formula I can also be used, for example, as photo-activatable hardeners for siloxane-group-containing resins. Those resins can, for example, either undergo self-condensation by way of acid-catalysed hydrolysis or can be crosslinked with a second resin component, such as, for example, a polyfunctional alcohol, a hydroxygroup-containing acrylic or polyester resin, a partially hydrolysed polyvinylacetal or a poly-vinyl alcohol. That type of polycondensation of polysiloxanes is described, for example, in J. J. Lebrun, H. Pode, Comprehensive Polymer Science Vol. 5, page 593, Pergamon Press, Oxford, 1989.

Especially preferred as acid-curable resins (a5) are amino resins, such as non-etherified or etherified melamine, urea, guanidine or biuret resins, especially methylated melamine resins or butylated melamine resins, corresponding glycolurils and urones. By "resins" in this context, there are to be understood both customary technical mixtures, which generally also comprise oligomers, and pure and high purity compounds. N-hexa(methoxymethyl) melamine and tetramethoxymethyl glucoril and N,N'-dimethoxymethylurone are the acid-curable resins given the greatest preference.

The crosslinker components should generally be present in a concentration of from 2 to 40, preferably from 5 to 30, percent by weight, based on the total solids content of the negative resist composition.

The concentration of the compound of formula I in negative resists in general is from 0.1 to 30, preferably up to 20, percent by weight, based on the total solids content of the compositions. From 1 to 15 percent by weight is especially preferred.

Binders may also be added to the compositions according to the invention, this being especially advantageous when the photopolymerisable compounds are liquid or viscous substances. The amount of binder may be, for example, from 5 to 95% by weight, preferably from 10 to 90% by weight and especially from 40 to 90% by weight, based on total solids. The binder will be selected according to the field of use and the properties required therefor, such as developability in aqueous and organic solvent systems, adhesion to substrates and sensitivity to oxygen.

Suitable binders are, for example, polymers having a molecular weight of approximately from 2000 to 2 000 000, preferably from 5000 to 1 000 000. Examples thereof are: homo- and co-polymers of acrylates and methacrylates, for example copolymers of methyl meth-acrylate/ethyl acrylate/ methacrylic acid, poly(methacrylic acid alkyl esters), poly (acrylic acid alkyl esters); phenolic resins, cellulose derivatives, such as cellulose esters and ethers, for example cellulose acetate, cellulose acetate butyrate, methyl cellulose, ethyl cellulose; polyvinyl butyral, polyvinylformal, polyolefins, cyclised rubber, polyethers, such as poly-ethylene oxide, polypropylene oxide, polytetrahydrofuran; polystyrene, polycarbonate, poly-urethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethyleneadipamide), polyesters such as poly(ethylene glycol terephthalate) and poly(hexamethylene glycol succinate); and polyamides Where appropriate, the negative compositions may comprise a film-forming polymeric binder (a4). This binder is preferably an alkali-soluble phenolic resin. Well suited for this purpose are, for example, novolaks, derived from an aldehyde, for example acetaldehyde or furfuraldehyde, but especially from formaldehyde, and a phenol, for example unsubstituted phenol, mono- or di-chlorosubstituted phenol, such as p-chlorophenol, phenol mono- or di-substituted by $C_1$-$C_9$alkyl, such as o-, m- or p-cresol, the various xylenols, p-tert-butylphenol, p-nonylphenol, p-phenylphenol, resorcinol, bis(4-hydroxyphenyl)methane or 2,2-bis(4-hydroxyphenyl)propane. Also suitable are homo- and co-polymers based on ethylenically unsaturated phenols, for example homopolymers of vinyl- and 1-propenyl-substituted phenols, such as p-vinylphenol or p-(1-propenyl)phenol or copolymers of these phenols with one or more ethylenically unsaturated materials, for example styrenes. The amount of binder should generally be from 30 to 95 percent by weight or, preferably, from 40 to 80 percent by weight.

Suitable formulations and the preparation of suitable polymer/copolymers for the negative resist using the compounds of the formula I according to the present invention are for example published in JP2003-043688A, JP2003-114531A, JP2002-287359A, JP2001-255656A, JP2001-305727A, JP2003-233185A, JP2003-186195A, U.S. Pat. No. 6,576, 394.

The chemically amplified negative, solvent-developable photoresists request the use of a specific component that when catalysed by an acid undergoes a crosslinking reaction or a polymerization with itself and/or with other components in the formulation. Suitable formulations are for example published in U.S. Pat. No. 4,882,245, U.S. Pat. No. 5,026, 624, U.S. Pat. No. 6,391,523.

A suitable component (a5) that when catalysed by an acid undergoes a crosslinking reaction or a polymerization with itselve and/or with other components includes, for example, an epoxidized bisphenol A formaldehyde novolak resin and an epoxidized tetrabromo bisphenol A formaldehyde novolak resin. The preferred epoxy resin contains an average of eight epoxy groups, consisting of the glycidyl ether of the novolak condensation product of bisphenol A and formaldehyde, with an average molecular weight of about 1400 gram/mole, with an epoxy equivalent weight of about 215 gram/mole. Such a resin is, for example, commercially available from Shell Chemical under the trade name EPON® Resin SU-8.

Various kinds of polymers can be used as the binder resin (a6) in the chemically amplified negative solvent-developable photoresist. Suitable examples include a phenoxy polyol resin which is a condensation product between epichlorohydrin and bisphenol A. A resin of this type is, for example, sold by Union Carbide Corporation under the Trade Mark PKHC.

The positive and the negative resist compositions may comprise in addition to the photosensitive acid donor compound of formula I, further photosensitive acid donor compounds (b1), further additives (c), other photoinitiators (d), and/or sensitizers (e).

Therefore, subject of the invention also are chemically amplified resist compositions as described above, in addition to components (a) and (b), or components (a1), (a2), (a3) and (b), or components (a4), (a5) and (b) comprising further additives (c), further photosensitive acid donor compounds (b1), other photoinitiators (d), and/or sensitizers (e).

Sulfonium salt derivatives of the present invention in the positive and negative resist can also be used together with other, known photolatent acids (b1), for example, onium salts, 6-nitrobenzylsulfonates, bis-sulfonyl diazomethane compounds, cyano group-containing oxime sulfonate compounds., etc. Examples of known photolatent acids for chemically amplified resists are described in U.S. Pat. No. 5,731, 364, U.S. Pat. No. 5,800,964, EP704762, U.S. Pat. No. 5,468, 589, U.S. Pat. No. 5,558,971, U.S. Pat. No. 5,558,976, U.S. Pat. No. 6,004,724, GB2348644 and particularly in EP794457 and EP 795786.

If a mixture of photolatent acids is used in the resist compositions according to the invention, the weight ratio of sulfonium salt derivatives of formula I to the other photolatent acid (b1) in the mixture is preferably from 1:99 to 99:1.

Examples of photolatent acids which are suitable to be used in admixture with the compounds of formula I are
(1) onium salt compounds, for example,
iodonium salts, sulfonium salts, phosphonium salts, diazonium salts, pyridinium salts. Preferred are diphenyliodonium triflate, diphenyliodonium pyrenesulfonate, diphenyliodonium dodecylbenzenesulfonate, triphenylsulfonium triflate, triphenylsulfonium hexafluoroantimonate, diphenyliodonium hexafluoroantimonate, triphenylsulfonium naphthalenesulfonate, (hydroxyphenyl)benzylmethylsulfonium toluenesulfonate, bis(4-tert-butylphenyl)iodonium bis(nonafluorobutanesulfonyl)imide, bis(4-tert-butylphenyl)iodonium tris(trifluoromethanesulfonyl)methide, triphenylsulfonium bis(trifluoromethanesulfonyl)imide, triphenylsulfonium (octafluorobutane-1,4-disulfonyl)imide, triphenylsulfonium tris(trifluoromethanesulfonyl)-methide, tert-butyl-diphenylsulfonium tris(trifluoromethanesulfonyl)methide, triphenylsulfonium 1,3-disulfonylhexafluoropropyleneimide, triarylsulfonium tetrakis-(pentafluorophenyl) borates, e.g. triphenylsulfonium tetrakis-(pentafluorophenyl)borate, diaryliodonium tetrakis(pentafluorophenyl)borates, e.g. diphenyl tetrakis(pentafluorophenyl) borate, diphenyl-[4-(phenylthio)phenyl]sulfonium trifluorotris(pentafluoroethyl)phosphate and the like; the iodonium cation may also be 4-methylphenyl-4'-isobutylphenyliodonium or 4-methylphenyl-4'-isopropylphenyliodonium. Particularly preferred are triphenylsulfonium triflate, diphenyliodonium hexafluoroantimonate. Other examples are described in JP2002-229192A, JP2003-140332A, JP2002-128755A, JP2003-035948A, JP2003-149800A, JP2002-006480A, JP2002-116546A, JP2002-156750A, U.S. Pat. No. 6,458, 506, US2003/27061, U.S. Pat. No. 5,554,664, WO07/118794.
(2) halogen-containing compounds
haloalkyl group-containing heterocyclic compounds, haloalkyl group-containing hydrocarbon compounds and the like. Preferred are (trichloromethyl)-s-triazine derivatives such as phenyl-bis(trichloromethyl)-s-triazine, methoxyphenyl-bis(trichloromethyl)-s-triazine, naphthyl-bis-(trichloromethyl)-s-triazine and the like; 1.1-bis(4-chlorophnyl)-2,2,2-trichloroethane; and the like.
(3) sulfone compounds, for example of the formula

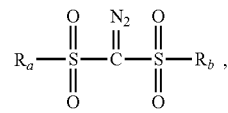

wherein $R_a$ and $R_b$ independently of one another are alkyl, cycloalkyl or aryl, each of which may have at least one substituent, e.g.

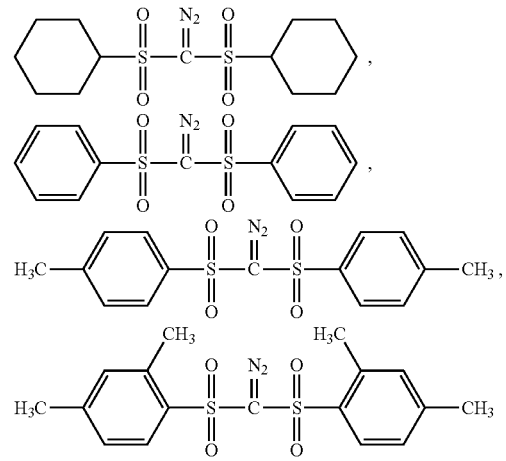

Such compounds are disclosed for example in US 2002/0172886-A, JP2003-192665A, US2002/9663. More examples are β-ketosulfones, β-sulfonylsulfones and their α-diazo derivatives and the like. Preferred are phenacylphenylsulfone, mesitylphenacylsulfone, bis(phenylsulfonyl)methane, bis(phenylsulfonyl)diazomethane.
(4) sulfonate compounds, for example
alkylsulfonic acid esters, haloalkylsulfonic acid esters, arylsulfonic acid esters, iminosulfonates, imidosulfonates and the like. Preferred imidosulfonate compounds are, for example, N-(trifluoromethlsulfonyloxy)succinimide, N-(trifluoromethylsulfonyloxy)phthalimide, N-(trifluoromethylsulfonyloxy)naphthylimide, N-(trifluoromethylsulfonyloxy)diphenylmaleimide, N-(trifluoromethylsulfonyloxy)-bicyclo-[2,2,1]-hept-5-ene-2,3-dicarboximide, N-(trifluoromethylsulfonyloxy)-7-oxabicyclo-[2,2,1]-hept-5-ene-2,3-dicarboximide, N-(trifluoromethylsulfonyloxy)-7-oxabicyclo-[2,2,1]-hept-5-ene-2,3-dicarboximide, N-(trifluoromethylsulfonyloxy)-bicyclo-[2,2,1]-heptan-5,6-oxy-2,3-dicarboximide,
N-(camphanylsulfonyloxy) succinimide, N-(camphanylsulfonyloxy)phthalimide, N-(camphanylsulfonyloxy)naphthylimide, N-(camphanylsulfonyloxy)diphenylmaleimide, N-(camphanylsulfonyloxy)-bicyclo-[2,2,1]-hept-5-ene-2,3-dicarboximide, N-(camphanylsulfonyloxy)-7-oxabicyclo-[2,2,1]-hept-5-ene-2,3-dicarboximide, N-(camphanylsulfonyloxy)-7-oxabicyclo-[2,2,1]hept-5-ene-2,3-dicarboximide, N-(camphanyl-sulfonyloxy)-bicyclo-[2,2,1]-heptan-5,6-oxy-2,3-dicarboximide, N-(4-methylphenylsulfonyl-oxy)succinimide, N-(4-methylphenylsulfonyloxy)phthalimide, N-(4-methylphenylsulfonyloxy)naphthylimide, N-(4-methylphenylsulfonyloxy)naphthylimide, N-(4-methylphenylsulfonyloxy)diphenylmaleimide, N-(4-methylphenylsulfonyloxy)-bicyclo-[2,2,1]-hept-5-ene-2,3-dicarboximide, N-(4-methylphenylsulfonyloxy)-7-oxabicyclo-[2,2,1]-hept-5-ene-2,3-dicarboximide, N-(4- methylphenylsulfonyloxy)-bicyclo-[2,2,1]-heptan-5,6-oxy-2,3-dicarboximide, N-(2-trifluoromethylphenylsulfonyloxy)succinimide, N-(2-trifluoromethylphenylsulfonyloxy)-naphthylimide, N-(2-trifluoromethylphenylsulfonyloxy)diphenylmaleimide, N-(2-trifluoromethylphenylsulfonyloxy)-bicyclo-[2,2,1]-hept-5-ene-2,3-dicarboximide, N-(2-trifluoromethylphenylsulfonyloxy)-7-oxabicyclo-[2,2,1]-hept-5-ene-2,3-dicarboximide, N-(2-trifluoromethylphenylsulfonyloxy)-bicyclo-[2,2,1]-heptan-5,6-oxy-2,3-dicarboximide and the like.

Other suitable sulfonate compounds preferably are, for example, benzoin tosylate, pyrogallol tristriflate, pyrogallolomethanesulfonic acid triester, nitorobenzyl-9,10-diethyoxyanthracene-2-sulfonate, α-(4-toluene-sulfonyloxyimino)-benzyl cyanide, α-(4-toluene-sulfonyloxyiimino)-4-methoxybenzyl cyanide, α-(4-toluene-sulfonyloxyimino)-2-thienylmethyl cyanide, α-(methanesulfonyloxyimino)-1-cyclohexenylacetonitrile, α-(butylsulfonyloxyimino)-1-cyclopentenylacetonitrile, (4-methylsulfonyloxyimino-cyclohexa-2,5-dienylidene)-phenylacetonitrile, (5-methylsulfonyloxyimino-5H-thiophen-2-ylidene)-phenyl-acetonitrile, (5-methylsulfonyloxyimino-5H-thiophen-2-ylidene)-(2-methylphenyl)-acetonitrile, (5-propylsulfonyloxyimino-5H-thiophen-2-ylidene)-(2-methylphenyl)-acetonitrile, (5-(p-toluenesulfonyloxyimino)-5H-thiophen-2-ylidene)-(2-methylphenyl)-acetonitrile, (5-(10-camphorsulfonyloxyimino)-5H-thiophen-2-ylidene)-(2-methylphenyl)-acetonitrile, (5-methylsulfonyloxyimino-5H-thiophen-2-ylidene)-(2-chlorophenyl)-acetonitrile, 2,2,2-trifluoro-1-{4-(3-[4-{2,2,2-trifluoro-1-(1-propanesulfonyloxyimino)-ethyl}-phenoxy]-propoxy)-phenyl}-ethanone oxime 1-propanesulfonate, 2,2,2-trifluoro-1-{4-(3-[4-{2,2,2-trifluoro-1-(1-p-toluenesulfonyloxyimino)-ethyl}-phenoxy]-propoxy)-phenyl}-ethanone oxime 1-p-toluenesulfonate, 2-[2,2,3,3,4,4,5,5,6,6,7,7-dodecafluoro-1-(nonafluorobutylsulfonyloxyimino)-heptyl]-fluorene, 2-[2,2,3,3,4,4,4-heptafluoro-1-(nonafluorobutylsulfonyloxyimino)-butyl]-fluorene, 2-[2,2,3,3,4,4,5,5-octafluoro-1-(nonafluoro-butylsulfonyloxyimino)-pentyl]-fluorene, 8-[2,2,3,3,4,4,5,5-octafluoro-1-(nonafluorobutylsulf-onyloxyimino)-pentyl]-fluoranthene and the like.

In the radiation sensitive resin composition of this invention, particularly preferred sulfonate compounds include pyrogallolmethanesulfonic acid triester, N-(trifluoromethylsulfonyloxy)bicyclo-[2,2,1]-hept-5-ene-2,3-dicarboximide, N-(camphanylsulfonyloxy)naphthylimide, N-(2-tri-fluoromethylphenylsulfonyloxy)phthalimide, N-(trifluoromethylsulfonyloxy)-bicyclo-[2,2,1]-hept-5-ene-2,3-dicarboximide, N-(camphanylsulfonyloxy)naphthylimide, N-(2-trifluoromethyl-phenylsulfonyloxy)phthalimide and the like.

(5) Quinonediazide compounds, for example
1,2-quinonediazidesulfonic acid ester compounds of polyhydroxy compounds. Preferred are compounds having a 1,2-quinonediazidesulfonyl group, e.g. a 1,2-benzoquinonediazide-4-sulfonyl group, a 1,2-naphthoquinonediazide-4-sulfonyl group, a 1,2-naphthoquinonediazide-5-sulfonyl group, a 1,2-naphthoquinonediazide-6-sulfonyl group or the like. Particularly preferred are compounds having a 1,2-naphthoquinonediazide-4-sulfonyl group or a 1,2-naphthoquinonediazide-5-sulfonyl group. In particular suitable are 1,2-quinonediazidesulfonic acid esters of (poly)hydroxy aryl ketones such as 2,3,4-trihydroxybenzophenone, 2,4,6-trihydroxybenzophenone, 2,3,4,4'-tetrahydroxybenzophenone, 2,2',3,4-tetrahydroxybenzophenone, 2,3,4,4'-tetrahydroxybenzophenone, 2,2',4,4'-tetrahydroxybenzophenone, 2,2',3,4,4'-pentahydroxybenzophenone, 2,2',3,2,6'-pentahydroxybenzophenone, 2,3,3',4,4',5'-hexahydroxybenzophenone, 2,3',4,4',5,6'-hexahydroxybenzophenone and the like; 1,2-quinonediazidesulfonic acid esters of bis-[(poly)hydroxylphenyl]alkanes such as bis(4-hydroxyphenyl)ethane, bis(2,4-dihydroxyphenyl)ethane, 2,2-bis(4-hydroxyphenyl)propane, 2,2-bis(2,4-dihydroxyphenyl)propane, 2,2-bis-(2,3,4-trihydroxyphenyl)propane and the like; 1,2-quinonediazidesulfonic acid esters of (poly)hydroxyphenylalkanes such as 4,4'-dihydroxytriphenylmethane, 4,4'4"-trihydroxytriphenylmethane, 4,4'5,5'-tetramethyl-2,2'2"-trihydroxytriphenylmethane, 2,2,5,5'-tetramethyl-4,4',4"-trihydroxytriphenylmethane, 1,1,1-tris(4-hydroxyphenyl)ethane, 1,1-bis(4-hydroxyphenyl)-1-phenylethane, 1,1-bis(4-hydroxyphenyl)-1-(4-[1-(hydroxyphenyl)-1-methylethyl]-phenyl)ethane and the like; 1,2-quinonediazidesulfonic acid esters of (poly)hydroxylphenylflavans such as 2,4,4-trimethyl-2',4',7-trihydroxy-2-phenylflavan, 2,4,4-trimethyl-2',4',5',6,7-pentahydroxy-2-phenylflavan and the like.

Other examples of photolatent acids which are suitable to be used in admixture with the compounds according to the present invention are described in JP2003-043678A, JP2003-005372A, JP-2003-043677A, JP2002-357904A, JP2002-229192A.

The positive and negative photoresist composition of the present invention may optionally contain one or more additives (c) customarily used in photoresists in the customary amounts known to a person skilled in the art, for example, dyes, pigments, plasticizers, surfactants, flow improvers, wetting agents, adhesion promoters, thixotropic agents, colourants, fillers, solubility accelerators, acid-amplifier, photosensitizers and organic basic compounds.

Further examples for organic basic compounds which can be used in the resist composition of the present invenion are compounds which are stronger bases than phenol, in particular, nitrogen-containing basic compounds. These compounds may be ionic, like, for example, tetraalkylammonium salts or non-ionic. Preferred organic basic compounds are nitrogen-containing basic compounds having, per molecule, two or more nitrogen atoms having different chemical environments. Especially preferred are compounds containing both at least one substituted or unsubstituted amino group and at least one nitrogen-containing ring structure, and compounds having at least one alkylamino group. Examples of such preferred compounds include guanidine, aminopyridine, amino alkylpyridines, aminopyrrolidine, indazole, imidazole, pyrazole, pyrazine, pyrimidine, purine, imidazoline, pyrazoline, piperazine, aminomorpholine, and aminoalkylmorpholines. Suitable are both, the unsubstituted compounds or substituted derivatives thereof. Preferred substituents include amino, aminoalkyl groups, alkylamino groups, aminoaryl groups, arylamino groups, alkyl groups, alkoxy groups, acyl groups acyloxy groups aryl groups, aryloxy groups, nitro, hydroxy, and cyano. Specific examples of especially preferred organic basic compounds include guanidine, 1,1-dimethylguanidine, 1,1,3,3-tetramethylguanidine, 2-aminopyridine, 3-aminopyridine, 4-aminopyridine, 2-dimethylaminopyridine, 4-dimethylaminopyridine, 2-diethylaminopyridine, 2-(aminomethyl)-pyridine, 2-amino-3-methylpyridine, 2-amino-4-methylpyridine, 2-amino-5-methylpyridine, 2-amino-6-methylpyridine, 3-aminoehtylpyridine, 4-aminoethylpyridine, 3-aminopyrrolidine, piperazine, N-(2-aminoethyl)piperazine, N-(2-aminoethyl)piperidine, 4-amino-2,2,6,6-tetramethylpiperidine, 4-piperidinopiperidine, 2-imimopiperidine, 1-(2-aminoethyl)pyrrolidine, pyrazole, 3-amino-5-methylpyrazole, 5-amino-3-methyl-1-p-tolyl pyrazole, pyrazine, 2-(aminomethyl)-5-methylpyrazine, pyrimidine, 2,4-diaminopyrimidine, 4,6-dihydroxypyrimidine, 2-pyrazoline, 3-pyrazoline, N-aminomorpholine, and N-(2-aminoethyl)morpholine.

Other examples of suitable organic basic compounds are described in DE4408318, U.S. Pat. No. 5,609,989, U.S. Pat. No. 5,556,734, EP762207, DE4306069, EP611998, EP813113, EP611998, U.S. Pat. No. 5,498,506, JP2003-043677A, JP2003-043678A, JP2002-226470A, JP2002-363146A, JP2002-363148A, JP2002-363152A, JP2003-98672A, JP2003-122013A, JP2002-341522A. However, the organic basic compounds suitable in the present invention are not limited to these examples.

The nitrogen-containing basic compounds may be used alone or in combination of two or more thereof. The added amount of the nitrogen-containing basic compounds is usually from 0.001 to 10 parts by weight, preferably from 0.01 to 5 parts by weight, per 100 parts by weight of the photosensitive resin composition (excluding the solvent). If the amount thereof is smaller than 0.001 part by weight, the effects of the present invention cannot be obtained. On the other hand, if it exceeds 10 parts by weight, reduced sensitivity and impaired developability at unexposed parts are liable to be caused.

The composition can further contain a basic organic compound which decomposes under actinic radiation ("suicide base") such as for example described in EP710885, U.S. Pat. No. 5,663,035, U.S. Pat. No. 5,595,855, U.S. Pat. No. 5,525,453 and EP611998.

Examples of dyes (c) suitable for the compositions of the present invention are oil-soluble dyes and basic dyes, e.g. Oil Yellow #101, Oil Yellow #103, Oil Pink #312, Oil Green BG, Oil Blue BOS, Oil Blue #603, Oil Black BY, Oil Black BS, Oil Black T-505 (all manufactured by Orient Chemical Industries Ltd., Japan), crystal violet (CI42555), methyl violet (CI 42535), rhodamine B (CI 45170B), malachite green (CI 42000), and methylene blue (CI52015).

Spectral sensitizers (e) may be further added to sensitize the photo latent acid to exhibit absorption in a region of longer wavelengths than far ultraviolet, whereby the photosensitive composition of the present invention can, for example, be rendered sensitive to an i-line or g-line radiation. Examples of suitable spectral sensitizers include benzophenones, p,p'-tetramethyldiaminobenzophenone, p,p'-tetraethylethylaminobenzophenone, thioxanthone, 2-chlorothioxanthone, anthrone, pyrene, perylene, phenothiazine, benzil, acridine orange, benzoflavin, cetoflavin T, 9,10-diphenylanthracene, 9-fluorenone, acetophenone, phenanthrene, 2-nitrofluorene, 5-nitroacenaphthene, benzoquinone, 2-chloro-4-nitroaniline, N-acetyl-p-nitroaniline, p-nitroaniline, N-acetyl-4-nitro-1-naphthylamine, picramide, anthraquinone, 2-ethylanthraquinone, 2-tert-butylanthraquinone, 1,2-benzanthraquinone, 3-methyl-1,3-diaza-1,9-benzanthrone, dibenzalacetone, 1,2-naphthoquinone, 3-acylcoumarin derivatives, 3,3'-carbonyl-bis-(5,7-dimethoxycarbonylcoumarin), 3-(aroylmethylene)thiazolines, eosin, rhodamine, erythrosine, and coronene. However, the suitable spectral sensitizers are not limited to these examples.

These spectral sensitizers can be used also as light absorbers for absorbing the far ultraviolet emitted by a light source. In this case, the light absorber reduces light reflection from the substrate and lessens the influence of multiple reflection within the resist film, thereby diminishing the effect of standing waves.

Specific examples of such compounds are
1. Thioxanthones

Thioxanthone, 2-isopropylthioxanthone, 2-chlorothioxanthone, 1-chloro-4-propoxythioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di-[2-(2-methoxyethoxy)ethoxycarbonyl]-thioxanthone, 1,3-dimethyl-2-hydroxy-9H-thioxanthen-9-one 2-ethylhexylether, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxythioxanthone, 6-ethoxycarbon-yl-2-methoxythioxanthone, 6-ethoxycarbonyl-2-methylthioxanthone, thioxanthone-2-carboxylic acid polyethyleneglycol ester, 2-hydroxy-3-(3,4-dimethyl-9-oxo-9H-thioxanthon-2-yloxy)-N,N,N-trimethyl-1-propanaminium chloride;
2. Benzophenones benzophenone, 4-phenyl benzophenone, 4-methoxy benzophenone, 4,4'-dimethoxy benzophenone, 4,4'-dimethyl benzophenone, 4,4'-dichlorobenzophenone 4,4'-bis(dimethylamino)-benzophenone, 4,4'-bis(diethylamino)benzophenone, 4,4'-bis(methylethylamino)benzophenone, 4,4'-bis(p-isopropylphenoxy)benzophenone, 4-methyl benzophenone, 2,4,6-trimethylbenzophenone, 3-methyl-4'-phenyl-benzophenone, 2,4,6-trimethyl-4'-phenyl-benzophenone, 4-(4-methylthiophenyl)-benzophenone, 3,3'-dimethyl-4-methoxy benzophenone, methyl-2-benzoylbenzoate, 4-(2-hydroxyethylthio)-benzophenone, 4-(4-tolylthio) benzophenone, 1-[4-(4-benzoyl-phenylsulfanyl)-phenyl]-2-methyl-2-(toluene-4-sulfonyl)-propan-1-one, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl-1,4,7,10,13-pentaoxatridecyl)-benzophenone, 4-benzoyl-N,N-dimethyl-N-[2-(1-oxo-2-propenyl)oxy]-ethyl-benzenemethanaminium chloride;
3. Coumarins Coumarin 1, Coumarin 2, Coumarin 6, Coumarin 7, Coumarin 30, Coumarin 102, Coumarin 106, Coumarin 138, Coumarin 152, Coumarin 153, Coumarin 307, Coumarin 314, Coumarin 314T, Coumarin 334, Coumarin 337, Coumarin 500, 3-benzoyl coumarin, 3-benzoyl-7-methoxycoumarin, 3-benzoyl-5,7-di methoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)-coumarin], 3,3'-carbonyl-bis(7-methoxycoumarin), 3,3'-carbonyl-bis(7-diethylamino-coumarin), 3-isobutyroyl-coumarin, 3-benzoyl-5,7-dimethoxy-coumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino- 3-phenylcoumarin, 7-diethylamino-3-phenylcoumarin, the coumarin derivatives disclosed in JP09-179299A and JP09-325209A, for example 7-[{4-chloro-6-(diethylamino)-S-triazine-2-yl}amino]3-phenyl-coumarin;
4. 3-(aroylmethylene)-thiazolines
3-methyl-2-benzoylmethylene-β-naphthothiazoline, 3-methyl-2-benzoylmethylene-benzothiazoline, 3-ethyl-2-propionylmethylene-β-naphthothiazoline;
5. Rhodanines
4-dimethylaminobenzalrhodanine, 4-diethylaminobenzalrhodanine, 3-ethyl-5-(3-octyl-2-benzothiazolinylidene)-rhodanine, the rhodanine derivatives, formulae [1], [2], [7], disclosed in JP08-305019A;
6. Other Compounds
acetophenone, 3-methoxyacetophenone, 4-phenylacetophenone, benzil, 4,4'-bis(dimethylamino)benzil, 2-acetylnaphthalene, 2-naphthaldehyde, dansyl acid derivatives, 9,10-anthraquinone, anthracene, pyrene, aminopyrene, perylene, phenanthrene, phenanthrenequinone, 9-fluorenone, dibenzosuberone, curcumin, xanthone, thiomichler's ketone, α-(4-dimethylaminobenzylidene) ketones, e.g. 2,5-bis(4-diethylaminobenzylidene)cyclopentanone, 2-(4-dimethylamino-benzylidene)-indan-1-one, 3-(4-dimethylamino-phenyl)-1-indan-5-yl-propenone, 3-phenylthiophthalimide, N-methyl-3,5-di(ethylthio)-phthalimide, N-methyl-3,5-di (ethylthio)-phthalimide, phenothiazine, methylphenothiazine, amines, e.g. N-phenylglycine, ethyl 4-dimethylaminobenzoate, butoxyethyl 4-dimethylaminobenzoate, 4-dimethylaminoacetophenone, triethanolamine, methyldiethanolamine, dimethylaminoethanol, 2-(dimethylamino) ethyl benzoate, poly(propylenegylcol)-4-(dimethylamino) benzoate, pyrromethenes, e.g., 1,3,5,7,9-pentamethyl pyrromethene $BF_2$ complex, 2,8-diethyl-1,3,5,7,9-pentamethyl pyrromethene $BF_2$ complex, 2,8-diethyl-5-phenyl-1,3, 7,9-tetramethyl pyrromethene $BF_2$ complex, 9,10-bis(phenylethynyl)-1,8-dimethoxyanthracene, benzo[1,2,3-kl:4,5,6-k'l']dixanthene.

Further suitable additives (c) are "acid-amplifiers", compounds that accelerate the acid formation or enhance the acid concentration. Such compounds may also be used in combination with the sulfonium salt derivatives of the formula I according to the invention in positive or negative resists, or in imaging systems as well as in all coating applications. Such acid amplifiers are described e.g. in Arimitsu, K. et al. J. Photopolym. Sci. Technol. 1995, 8, pp 43; Kudo, K. et al. J. Photopolym. Sci. Technol. 1995, 8, pp 45; Ichimura, K. et al. Chem: Letters 1995, pp 551.

If desired, the composition according to the invention can also contain free-radically poly-merisable components, such as ethylenically unsaturated monomers, oligomers or polymers. These radically polymerizable components may be added to the component (a). Said radically curable components may, however, also be part of (a1), (a2), (a3), (a4), (a5) or (a6). Suitable materials contain at least one ethylenically unsaturated double bond and are capable of undergoing addition polymerisation. Such compounds are also the subject of component (ax), accordingly, the description below also refers to component (ax).

Examples of suitable monomers that contain an ethylenic double bond include alkyl and hydroxyalkyl acrylates and methacrylates, such as methyl, ethyl, propyl, isopropyl, butyl, hexyl, 2-ethylhexyl and 2-hydroxyethyl(meth)acrylate, stearyl acrylate and isobornyl acrylates. Further suitable examples include acrylonitrile, acrylamide, methacrylamide, N-substituted (meth)acrylamides, vinyl esters, such as vinyl acetate, vinyl ethers, such as isobutylvinyl ether, styrene, alkyl- and halo-substituted styrene, N-vinylpyrrolidone, vinyl chloride and vinylidene chloride.

Examples of suitable monomers that contain at least two double bonds include glycerol diacrylates, glycerol triacrylates, ethylene glycol diacrylates, diethylene glycol diacrylates, diethylene glycol dimethacrylate, triethylene glycol dimethacrylates, 1,3-propanediol di-acrylate, 1,3-propanediol dimethacrylate, neopentyl glycol diacrylates, hexamethylene glycol diacrylate, bisphenol-A diacrylates, 4,4'-bis(2-acryloyloxyethoxy)diphenylpropane, penta-erythritol triacrylate or tetraacrylate, pentaerythritol tetramethacrylate, tri methylolpropane triacrylate, 1,2,4-butanetriol trimethacrylate, 1,4-cyclohexanediol diacrylate, sorbitol hexaacrylate, bis[1-(2-acryloxy)]-p-ethoxyphenyldimethylmethane, bis[1-(3-acryloxy-2-hydroxy)]p-propoxyphenyldimethylmethane and trishydroxyethyl isocyanurate trimethacrylate; the bis-acrylates and bis-methacrylates of poly(ethylene glycol) having a molecular weight of from 200 to 500, diallyl phthalate, divinyl succinate, divinyl adipate and divinyl phthalate, vinyl acrylate, divinyl benzene, triallyl phosphate, triallyl isocyanurates and tris(2-acryloyl-ethyl)isocyanurate.

Examples of higher-molecular-weight (oligomeric) poly-unsaturated compounds include acrylated epoxy resins, acrylated or vinyl ether- or epoxy-group-containing polyesters, polyurethanes and polyethers. Further examples of unsaturated oligomers are unsaturated polyester resins, which are usually prepared from maleic acid, phthalic acid and one or more diols and have molecular weights of approximately from 500 to 3000. Vinyl ether monomers and oligomers, and maleate-terminated oligomers having polyester, poly-urethane, polyether, polyvinyl ether and epoxy main chains can also be used. Also copolymers of vinyl ethers and monomers which are functionalised with maleic acid, as described in WO90/01512, are also very suitable. Also suitable, however, are copolymers of monomers functionalised with vinyl ether and maleic acid. Such unsaturated oligomers can also be referred to as pre-polymers. Functionalised acrylates are also suitable. Examples of suitable monomers that are normally used to form the base polymer (the backbone) of the functionalised acrylate or methacrylate polymer are acrylate, methacrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate, etc. In addition, suitable amounts of functional monomers are copolymerised during the polymerisation in order to obtain the functional polymers. Acid-functionalised acrylate or methacrylate polymers are obtained using acid-functional monomers, such as acrylic acid and methacrylic acid. Hydroxy-functional acrylate or methacrylate polymers are obtained from hydroxy-functional monomers, such as 2-hydroxyethyl methacrylate, 2-hydroxypropyl methacrylate and 3,4-dihydroxybutyl methacrylate. Epoxy-functionalised acrylate or methacrylate polymers are obtained using epoxy-functional monomers, such as glycidyl methacrylate, 2,3-epoxybutyl methacrylate, 3,4-epoxybutyl methacrylate, 2,3-epoxycyclohexyl methacrylate, 10,11-epoxyundecyl meth-acrylate, etc. It is also possible to obtain isocyanate-functional polymers from isocyanate-functionalised monomers, such as meta-isopropenyl-α,α-dimethylbenzyl isocyanate. Especially suitable are, for example, esters of ethylenically unsaturated mono- or poly-functional carboxylic acids and polyols or polyepoxides, and polymers having ethylenically unsaturated groups in the chain or in side groups, such as unsaturated polyesters, poly-amides and polyurethanes and copolymers thereof, alkyd resins, polybutadiene and buta-diene copolymers, polyisoprene and isoprene copolymers, polymers and copolymers having (meth) acrylic groups in side chains, and mixtures of one or more such polymers. Examples of suitable mono- or poly-functional unsaturated carboxylic acids are acrylic acid, methacrylic acid, crotonic acid, itaconic acid, cinnamic acid, maleic acid and fumaric acid and unsaturated fatty acids, such as linolenic acid or oleic acid. Preference is given to acrylic acid and methacrylic acid.

Mixtures of saturated di- or poly-carboxylic acids with unsaturated carboxylic acids may, however, also be used. Examples of suitable saturated di- or poly-carboxylic acids include, for example, tetrachlorophthalic acid, tetrabromophthalic acid, phthalic acid anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid, etc. Suitable polyols are aromatic and especially aliphatic and cycloaliphatic polyols. Examples of aromatic polyols are hydroquinone, 4,4'-dihydroxydiphenyl, 2,2-di(4-hydroxyphenyl)-propane, and novolaks and resoles. Examples of polyepoxides are those based on the polyols mentioned, especially the aromatic polyols and epichlorohydrin. Also suitable as polyols are polymers and copolymers containing hydroxyl groups in the polymer chain or in side groups, such as polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris((3-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to have been modified, for example etherified, or esterified by other carboxylic acids.

Examples of esters are:
trimethylolpropane triacrylate, trimethylolethane triacrylate, trimethylolpropane trimeth-acrylate, trimethylolethane trimethacrylate, tetramethylene glycol dimethacrylate, triethylene glycol dimethacrylate, tetraethylene glycol diacrylate, pentaerythritol diacrylate, penta-erythritol triacrylate, pentaerythritol tetraacrylate, dipentaerythritol diacrylate, dipenta-erythritol triacrylate, dipentaerythritol tetraacrylate, dipentaerythritol pentaacrylate, dipenta-erythritol hexaacrylate, tripentaerythritol octaacrylate, pentaerythritol di methacrylate, penta-erythritol trimethacrylate, dipentaerythritol di methacrylate, dipentaerythritol tetrameth-acrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetramethacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

Suitable unsaturated, free-radically polymerisable compounds are also the amides of the same or different unsaturated carboxylic acids and aromatic, cycloaliphatic and aliphatic polyamines having preferably from 2 to 6, especially from 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetraamine and di(β-aminoethoxy)- or di-(β-aminopropoxy)-ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, bis(methacrylamidopropoxy)ethane, β-methacrylamidoethyl methacrylate and N-[(β-hydroxyethoxy)ethyl]acrylamide.

Suitable unsaturated polyesters and polyamides are derived, for example, from maleic acid and diols or diamines. The maleic acid may have been partially replaced by other dicarboxylic acids. They can be used together with ethylenically unsaturated comonomers, for example styrene. The polyesters and polyamides can also be derived from dicarboxylic acids and ethylenically unsaturated diols or diamines, especially from those having longer chains of, for example, from 6 to 20 carbon atoms. Examples of polyurethanes are those composed of saturated or unsaturated diisocyanates and saturated or unsaturated diols.

Polybutadiene and polyisoprene and copolymers thereof are known. Suitable comonomers include, for example, olefins, such as ethylene, propene, butene, hexene, (meth)acrylates, acrylonitrile, styrene and vinyl chloride. Polymers having (meth)acrylate groups in the side chain are also known. They may be, for example, reaction products of novolak-based epoxy resins with (meth)acrylic acid; homo- or copolymers of vinyl alcohol or hydroxyalkyl derivatives thereof that have been esterified with (meth)acrylic acid; or homo- and co-polymers of (meth)acrylates that have been esterified with hydroxyalkyl(meth)acrylates.

It is also possible to use compounds that can be crosslinked equally both free-radically and cationically. Such compounds contain, for example, both a vinyl group and a cycloaliphatic epoxy group. Examples thereof are described in JP02-289611A and U.S. Pat. No. 6,048,953.

Mixtures of two or more such free-radically polymerisable materials can also be used.

The formulations can also comprise dyes and/or white or coloured pigments as additional additives (c). Depending upon the intended use, it is possible to use both inorganic and organic pigments. Such additives are known to the person skilled in the art; some examples thereof are titanium dioxide pigments, for example of the rutile or anatase type, carbon black, zinc oxide, such as zinc white, iron oxides, such as iron oxide yellow, iron oxide red, chromium yellow, chromium green, nickel titanium yellow, ultramarine blue, cobalt blue, bismuth vanadate, cadmium yellow and cadmium red. Examples of organic pigments are mono- or bis-azo pigments, and metal complexes thereof, phthalocyanine pigments, polycyclic pigments, such as, for example, perylene, anthraquinone, thioindigo, quinacridone and triphenylmethane pigments, and diketo-pyrrolo-pyrrole, isoindolinone, e.g. tetrachloro-isoindolinone, isoindoline, dioxazine, benzimidazolone and quinophthalone pigments.

The pigments can be used individually or in admixture in the formulations. Depending upon the intended use, the pigments are added to the formulations in amounts customary in the art, for example in an amount of from 1 to 60% by weight, or from 10 to 30% by weight, based on the total weight.

The formulations may, for example, also comprise organic dyes of a wide variety of classes. Examples thereof include azo dyes, methine dyes, anthraquinone dyes and metal complex dyes. Customary concentrations are, for example, from 0.1 to 20%, especially from 1 to 5%, based on the total weight.

The pigments, latent pigments or dyes or differently coloured precursors of such pigments and dyes that are added may be so selected that they undergo a colour change in the presence of the acid formed from the iodonium salt as a result of irradiation. Such compositions then show, by the colour change, that they have been irradiated and can be used, for example, as irradiation dose indicators, e.g. for UV radiation, electron beams, X-rays, etc.

Other additives (c) to improve the resist performance such as resolution, pattern profile, process latitude, line edge roughness, stability are described in JP2002-122992A, JP2002-303986A, JP2002-278071 A, JP2003-057827A, JP2003-140348A, JP2002-006495A JP2002-023374A, JP2002-090987A, JP2002-091004A, JP2002-131913A, JP2002-131916A, JP2002-214768A, JP2001-318464A, JP2001-330947A, JP2003-57815A, JP2003-280200A, JP2002-287362A, JP2001-343750A. Such compounds may also be used in combination with the sulfonium salt derivatives of the formula I according to the invention in positive or negative resists.

Usually, for the application to a substrate of the photosensitive composition of the present invention, the composition is dissolved in an appropriate solvent. Preferred examples of these solvents include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, 2-ethoxyethyl acetate, 2-ethoxyethanol, diethyl glycol dimethyl ether, ethylene glycol monoethyl ether acetate, propylene glycol monomethyl ether, propylene glycol monomethyl ether acetate, toluene, ethyl acetate, butyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone, and tetrahydrofuran. These solvents may be used alone or as mixtures. Preferred examples of the solvents are esters, such as 2-methoxyethyl acetate, ethylene glycolmonoethyl ether acetate, propylene glycol monomethyl ether acetate, methyl methoxypropionate, ethyl ethoxypropionate, and ethyl lactate. Use of such solvents is advantageous because the sulfonium salt derivatives represented by formula I according to the present invention have good compatibility therewith and better solubility therein.

A surfactant can be added to the solvent. Examples of suitable surfactants include nonionic surfactants, such as polyoxyethylene alkyl ethers, e.g. polyoxyethylene lauryl ether, polyoxyethylene stearyl ether, polyoxyethylene acetyl ether, and polyoxyethylene oleyl ether; polyoxyethylene alkylaryl ethers, e.g. polyoxyethylene, octylphenol ether and polyoxyethylene nonylphenol ether; polyoxyethylene/polyoxypropylene block copolymers, sorbitan/fatty acid esters, e.g. sorbitan monolaurate, sorbitan monopalmitate, sorbitan monostearate, sorbitan monooleate, sorbitan trioleate; fluorochemical surfactants such as F-top EF301, EF303, and EF352 (manufactured by New Akita Chemical Company, Japan). Megafac F171 and F17.3 (manufactured by Dainippon Ink & Chemicals, Inc,. Japan), Fluorad FC 430 and FC431 (manufactured by Sumitomo 3M Ltd., Japan), Asahi Guard AG710 and Surflon S-382, SC101, SC102, SC103, SC104, SC105, and SC106 (manufactured by Asahi Grass Col, Ltd., Japan); organosiloxane polymer KP341 (manufactured by Shin-Etsu Chemical Co., Ltd., Japan); and acrylic or methacrylic (co)polymers Poly-flow Now.75 and NO.95 (manufactured by Kyoeisha Chemical Co., Ltd., Japan). Other examples are described in JP2001-318459A, JP2002-006483A. The added amount of the surfactant usually is 2 parts by weight or lower, desirably 0.5 part by weight or lower, per 100 parts by weight of the solid components of the composition of the present invention. The surfactants may be added alone or in combination of two or more thereof.

The solution is uniformly applied to a substrate by means of known coating methods, for example by spin-coating, immersion, knife coating, curtain pouring techniques, brush application, spraying and roller coating. It is also possible to apply the photosensitive layer to a temporary, flexible support and then to coat the final substrate by coating transfer (laminating). The amount applied (coating thickness) and the nature of the substrate (coating substrate) are dependent on the desired field of application. The range of coating thicknesses can in principle include values from approximately 0.01 μm to more than 100 μm.

After the coating operation generally the solvent is removed by heating, resulting in a layer of the photoresist on the substrate. The drying temperature must of course be lower than the temperature at which certain components of the resist might react or decompose. In general, drying temperatures are in the range from 60 to 160° C.

The resist coating is then irradiated image-wise. The expression "image-wise irradiation" includes irradiation in a predetermined pattern using actinic radiation, i.e. both irradiation through a mask containing a predetermined pattern, for example a transparency, a chrome mask or a reticle, and irradiation using a laser beam or electron beam that writes directly onto the resist surface, for example under the control of a computer, and thus produces an image. Another way to produce a pattern is by interference of two beams or images as used for example in holographic applications. It is also possible to use masks made of liquid crystals that can be addressed pixel by pixel to generate digital images, as is, for example described by A. Bertsch; J. Y. Jezequel; J. C. Andre in Journal of Photochemistry and Photobiology A: Chemistry 1997, 107 pp. 275-281 and by K. P. Nicolay in Offset Printing 1997, 6, pp. 34-37.

After the irradiation and, if necessary, thermal treatment, the irradiated sites (in the case of positive resists) or the non-irradiated sites (in the case of negative resists) of the composition are removed in a manner known per se using a developer.

In order to accelerate the catalytic reaction and hence the development of a sufficient difference in solubility between the irradiated and unirradiated sections of the resist coating in the developer, the coating is preferably heated before being developed. The heating can also be carried out or begun during the irradiation. Temperatures of from 60 to 160° C. are preferably used. The period of time depends on the heating method and, if necessary, the optimum period can be determined easily by a person skilled in the art by means of a few routine experiments. It is generally from a few seconds to several minutes. For example, a period of from 10 to 300 seconds is very suitable when a hotplate is used and from 1 to 30 minutes when a convection oven is used. It is important for the latent acid donors according to the invention in the unirradiated sites on the resist to be stable under those processing conditins.

The coating is then developed, the portions of the coating that, after irradiation, are more soluble in the developer being removed. If necessary, slight agitation of the workpiece, gentle brushing of the coating in the developer bath or spray developing can accelerate that process step. The aqueous-alkaline developers customary in resist technology may, for example, be used for the development. Such developers comprise, for example, sodium or potassium hydroxide, the corresponding carbonates, hydrogen carbonates, silicates or metasilicates, but preferably metal-free bases, such as ammonia or amines, for example ethylamine, n-propylamine, diethylamine, di-n-propylamine, triethylamine, methyl diethylamine, alkanolamines, for example dimethyl ethanolamine, triethanolamine, quaternary ammonium hydroxides, for example tetramethylammonium hydroxide or tetraethylammonium hydroxide. The developer solutions are generally up to 0.5 N, but are usually diluted in suitable manner before use. For example solutions having a normality of approximately 0.1-0.3 are well suited. The choice of developer depends on the nature of the photocurable surface coating, especially on the nature of the binder used or of the resulting photolysis products. The aqueous developer solutions may, if necessary, also comprise relatively small amounts of wetting agents and/or organic solvents. Typical organic solvents that can be added to the developer fluids are, for example, cyclohexanone, 2-ethoxyethanol, toluene, acetone, isopropanol and also mixtures of two or more of these solvents. A typical aqueous/organic developer system is based on Butylcellosolve™/water.

Subject of the invention also is a process for the preparation of a photoresist by
(1) applying to a substrate a composition as described above;
(2) post apply baking the composition at temperatures between 60° C. and 160° C.;
(3) image-wise irradiating with light of wavelengths between 10 nm and 1500 nm;
(4) optionally post exposure baking the composition at temperatures between 60° C. and 160° C.; and
(5) developing with a solvent or with an aqueous alkaline developer.

Preferred is a process, wherein the image-wise irradiation is carried out with monochromatic or polychromatic radiation in the wavelength range from 10 to 450 nm, in particular in the range from 10 to 260 nm.

The photoresist compositions can be used on all substrates and with all exposure techniques known to the person skilled in the art. For example, semiconductor substrates can be used, such as silicon, gallium arsenide, germanium, indium antimonide; furthermore substrate covered by oxide or nitride layers, such as silicon dioxide, silicon nitride, titanium nitride, siloxanes, as well as metal substrates and metal coated substrates with metals such as aluminium, copper, tungsten, etc. The substrate can also be coated with polymeric materials, for example with organic antireflective coatings, insulation layers and dielectric coatings from polymeric materials prior to coating with the photoresist.

The photoresist layer can be exposed by all common techniques, such as direct writing, i.e. with a laser beam or projection lithography in step- and repeat mode or scanning mode, or by contact printing through a mask.

In case of projection lithography a wide range of optical conditions can be used such as coherent, partial coherent or incoherent irradiation. This includes off-axis illumination techniques, for example annular illumination and quadrupol illumination where the radiation is allowed to pass only certain regions of the lens, excluding the lens center.

The mask used to replicate the pattern can be a hard mask or a flexible mask. The mask can include transparent, semi-transparent and opaque patterns. The pattern size can include also patterns which are at or below the resolution limit of the projection optics and placed on the mask in a certain way in order to modify the aerial image, intensity and phase modulation of the irradiation after having passed the mask. This includes phase shift masks and half-tone phase shift masks.

The patterning process of the photoresist composition can be used to generate patterns of any desired geometry and shape, for example dense and isolated lines, contact holes, trenches, dots, etc.

The photoresists according to the invention have excellent lithographic properties, in particular a high sensitivity, and high resist transparency for the imaging radiation.

Possible areas of use of the composition according to the invention are as follows: use as photoresists for electronics, such as etching resists, ion-implantation resist, electroplating resists or solder resists, the manufacture of integrated circuits or thin film transistor-resist (TFT); the manufacture of printing plates, such as offset printing plates or screen printing stencils, use in the etching of mouldings or in stereolithography or holography techniques, which are employed for various applications, for example, 3D optical information storage described in J. Photochem. Photobio. A, 158, 163 (2003), Chem. Mater. 14, 3656 (2002).

The composition according to the invention is also suitable for making inter-metal dielectrics layer, buffer layer, passivation coat of semiconductor devices and suitable for making waveguide for optoelectronics. For MEMS (micro electro mechanical systems) application, the composition according to the invention can be used as etching resist, mold for material deposition, and three dimensional objects of device itself. The coating substrates and processing conditions vary accordingly. Such example is described in U.S. Pat. No. 6,391,523.

The compounds of formula I according to the present invention, in combination with a sensitizer compound as described above, can also be used in holographic data storage (HDS) systems as for example described in WO03/021358.

The compositions according to the invention include also adhesives, as used, for example, for adhesive bonding (DVD bonding) in the manufacture of digital versatile disks (DVD) and as described, for example, in: WO99/66506, WO99/63017, JP11-241055A, JP11-181391A, WO 98/31765, and also as radiation-curable laminating adhesives for flexible packaging (see, e.g., U.S. Pat. No. 5,328,940), optical adhesives (e.g. German Patent Application DD 225985) and pressure-sensitive adhesives (e.g. U.S. Pat. No. 4,988,741 and EP115870).

The compositions according to the invention are advantageously used where there is a need for hard coatings, adhesive bonds or photopolymerised dimensionally stable three-dimensional mouldings (e.g. for rapid prototyping) having good adhesion to paper, glass, metal, silicon, polycarbonate, acrylate polymers and other polymer substrates, and that exhibit only slight shrinkage during curing.

The compositions according to the invention are also outstandingly suitable as coating compositions for substrates of all types, including wood, textiles, paper, ceramics, glass, plastics, such as polyesters, polyethylene terephthalate, polyolefins or cellulose acetate, especially in the form of films, but especially for coating metals, such as Ni, Fe, Zn, Mg, Co or especially Cu and Al, and also Si, silicon oxides or nitrides, to which an image is to be applied by means of image-wise irradiation.

The invention relates also to the use of compounds of formula I as photolatent acid donors in compositions that can be crosslinked under the action of an acid and/or as dissolution enhancers in compositions wherein the solubility is increased under the action of an acid. Subject of the invention further is a process of crosslinking compounds that can be crosslinked under the action of an acid, which method comprises adding a compound of formula I to the above-mentioned compositions and irradiating imagewise or over the whole area with light having a wavelength of 10-1500 nm.

The invention relates also to the use of compounds of formulae I as photosensitive acid donors in the preparation of pigmented and non-pigmented surface coatings, adhesives, laminating adhesives, structural adhesives, pressure-sensitive adhesives, printing inks, printing plates, relief printing plates, planographic printing plates, intaglio printing plates, processless printing plates, screen printing stencils, dental compositions, colour filters, spacers, electroluminescence displays and liquid crystal displays (LCD), waveguides, optical switches, color proofing systems, resists, photoresists for electronics, electroplating resists, etch resists both for liquid and dry films, solder resist, photoresist materials for a UV and visible laser direct imaging system, photoresist materials for forming dielectric layers in a sequential build-up layer of a printed circuit board, image-recording materials, image-recording materials for recording holographic images, optical information storage or holographic data storage, decolorizing materials, decolorizing materials for image recording materials, image recording materials using microcapsules, magnetic recording materials, micromechanical parts, plating masks, etch masks, glass fibre cable coatings, microelectronic circuits; in particular to the use of compounds of the formula I, as photosensitive acid donors in the preparation of surface coatings, printing inks, printing plates, dental compositions, colour filters, resists or image-recording materials, or image-recording materials for recording holographic images; as well as to a process for the preparation for the preparation of pigmented and non-pigmented surface coatings, adhesives, laminating adhesives, structural adhesives, pressure-sensitive adhesives, printing inks, printing plates, relief printing plates, planographic printing plates, intaglio printing plates, processless printing plates, screen printing stencils, dental compositions, colour filters, spacers, electroluminescence displays and liquid crystal displays (LCD), waveguides, optical switches, color proofing systems, resists, photoresists for electronics, electroplating resists, etch resists both for liquid and dry films, solder resist, photoresist materials for a UV and visible laser direct imaging system, photoresist materials for forming dielectric layers in a sequential build-up layer of a printed circuit board, image-recording materials, image-recording materials for recording holographic images, optical information storage or holographic data storage, decolorizing materials, decolorizing materials for image recording materials, image recording materials using microcapsules, magnetic recording materials, micromechanical parts, plating masks, etch masks, glass fibre cable coatings, microelectronic circuits; in particular to a process for the preparation of surface coatings, printing inks, printing plates, dental compositions, colour filters, resists, or image-recording materials, or image-recording materials for recording holographic images.

Subject of the invention is also the use of compounds of formula I as photosensitive acid donors in the preparation of colour filters or chemically amplified resist materials; as well as to a process for the preparation of colour filters or chemically amplified resist materials.

The invention further pertains to a color filter prepared by providing red, green and blue picture elements and a black matrix, all comprising a photosensitive resin and a pigment and/or dye on a transparent substrate and providing a transparent electrode either on the surface of the substrate or on the surface of the color filter layer, wherein said photosensitive resin comprises compounds of formula I as photosensitive acid donors.

The person skilled in the art is aware of suitable pigments or dyes to provide the color elements, as well as the black matrix and corresponding suitable resins as shown in, for examples, JP09-203806A, JP10-282650A, JP10-333334A, JP11-194494A, JP10-203037A, JP2003-005371 A.

As already mentioned above, in photocrosslinkable compositions, sulfonium salt derivatives act as latent curing catalysts: when irradiated with light they release acid which catalyses the crosslinking reaction. In addition, the acid released by the radiation can, for example, catalyse the removal of suitable acid-sensitive protecting groups from a polymer structure, or the cleavage of polymers containing acid-sensitive groups in the polymer backbone. Other applications are, for example, colour-change systems based on a change in the pH or in the solubility of, for example, a pigment protected by acid-sensitive protecting groups.

Sulfonium salt derivatives according to the present invention can also be used to produce so-called "print-out" images when the compound is used together with a colourant that changes colour when the pH changes, as described e.g. in JP04-328552A or in U.S. Pat. No. 5,237,059. Such color-change systems can be used according to EP199672 also to monitor goods that are sensitive to heat or radiation.

In addition to a colour change, it is possible during the acid-catalysed deprotection of soluble pigment molecules (as described e.g. in EP648770, EP648817 and EP742255) for the pigment crystals to be precipitated; this can be used in the production of colour filters as described e.g. in EP654711 or print out images and indicator applications, when the colour of the latent pigment precursor differs from that of the precipitated pigment crystal.

Compositions using pH sensitive dyes or latent pigments in combination with sulfonium salt derivatives can be used as indicators for electromagnetic radiation, such as gamma radiation, electron beams, UV- or visible light, or simple throw away dosimeters. Especially for light, that is invisible to the human eye, like UV- or IR-light, such dosimeters are of interest.

Finally, sulfonium salt derivatives that are sparingly soluble in an aqueous-alkaline developer can be rendered soluble in the developer by means of light-induced conversion into the free acid, with the result that they can be used as solubility enhancers in combination with suitable film-forming resins.

Resins which can be crosslinked by acid catalysis and accordingly by the photolatent acids of formula I according to the invention, are, for example, mixtures of polyfunctional alcohols or hydroxy-group-containing acrylic and polyester resins, or partially hydrolysed polyvinylacetals or polyvinyl alcohols with polyfunctional acetal derivatives. Under certain conditions, for example the acid-catalysed self-condensation of acetal-functionalised resins is also possible.

Suitable acid-curable resins in general are all resins whose curing can be accelerated by acid catalysts, such as aminoplasts or phenolic resole resins. These resins are for example melamine, urea, epoxy, phenolic, acrylic, polyester and alkyd resins, but especially mixtures of acrylic, polyester or alkyd resins with a melamine resin. Also included are modified surface-coating resins, such as acrylic-modified polyester and alkyd resins. Examples of individual types of resins that are covered by the expression acrylic, polyester and alkyd resins are described, for example, in Wagner, Sarx, Lackkunstharze (Munich, 1971), pp. 86-123 and pp. 229-238, or in Ullmann, Encyclopädie der techn. Chemie, 4th Ed., Vol. 15

(1978), pp. 613-628, or Ullmann's Encyclopedia of Industrial Chemistry, Verlag Chemie, 1991, Vol. 18, p. 360 ff., Vol. A19, p. 371 ff.

In coating applications the surface coating preferably comprises an amino resin. Examples thereof are etherified or non-etherified melamine, urea, guanidine or biuret resins. Acid catalysis is especially important in the curing of surface coatings comprising etherified amino resins, such as methylated or butylated melamine resins (N-methoxymethyl- or N-butoxymethyl-melamine) or methylated/butylated glycolurils. Examples of other resin compositions are mixtures of polyfunctional alcohols or hydroxy-group-containing acrylic and polyester resins, or partially hydrolysed polyvinyl acetate or polyvinyl alcohol with polyfunctional dihydropropanyl derivatives, such as derivatives of 3,4-dihydro-2H-pyran-2-carboxylic acid. Polysiloxanes can also be crosslinked using acid catalysis. These siloxane group-containing resins can, for example, either undergo self-condensation by means of acid-catalysed hydrolysis or be crosslinked with a second component of the resin, such as a polyfunctional alcohol, a hydroxy-group-containing acrylic or polyester resin, a partially hydrolysed polyvinyl acetal or a polyvinyl alcohol. This type of polycondensation of polysiloxanes is described, for example, in J. J. Lebrun, H. Pode, Comprehensive Polymer Science, Vol. 5, p. 593, Pergamon Press, Oxford, 1989. Other cationically polymerisable materials that are suitable for the preparation of surface coatings are ethylenically unsaturated compounds polymerisable by a cationic mechanism, such as vinyl ethers, for example methyl vinyl ether, isobutyl vinyl ether, trimethylolpropane trivinyl ether, ethylene glycol divinyl ether; cyclic vinyl ethers, for example 3,4-dihydro-2-formyl-2H-pyran (dimeric acrolein) or the 3,4-dihydro-2H-pyran-2-carboxylic acid ester of 2-hydroxymethyl-3,4-dihydro-2H-pyran; vinyl esters, such as vinyl acetate and vinyl stearate, mono- and di-olefins, such as a-methylstyrene, N-vinylpyrrolidone or N-vinylcarbazole.

For certain purposes, resin mixtures having monomeric or oligomeric constituents containing polymerisable unsaturated groups are used. Such surface coatings can also be cured using compounds of formula I. In that process, radical polymerisation initiators or photoinitiators can additionally be used. The former initiate polymerisation of the unsaturated groups during heat treatment, the latter during UV irradiation.

The invention further pertains to a composition comprising
(a) a compound which cures upon the action of an acid or a compound whose solubility is increased upon the action of an acid; and
(b) as photosensitive acid donor, at least one compound of the formula I.

According to the invention, the compounds of formula I can be used together with further photosensitive acid donor compounds (b1), further photoinitiators (d), sensitisers (e) and/or additives (c).

Suitable photosensitive acid donor compounds (b1), sensitizers (e) and additives (c) are described above.

Examples of additional photoinitiators (d) are radical photoinitiators, such as for example camphor quinone; benzophenone, benzophenone derivatives; ketal compounds, as for example benzildimethylketal (IRGACURE® 651); acetophenone, acetophenone derivatives, for example α-hydroxycycloalkyl phenyl ketones or α-hydroxyalkyl phenyl ketones, such as for example 2-hydroxy-2-methyl-1-phenyl-propanone (DAROCUR® 1173), 1-hydroxy-cyclohexyl-phenyl-ketone (IRGACURE® 184), 1-(4-dodecylbenzoyl)-1-hydroxy-1-methyl-ethane, 1-(4-isopropylbenzoyl)-1-hydroxy-1-methyl-ethane, 1-[4-(2-hydroxyethoxy)-phenyl]-2-hydroxy-2-methyl-1-propan-1-one (IRGACURE® 2959); 2-hydroxy-1-{4-[4-(2-hydroxy-2-methylpropionyl)-benzyl]-phenyl}-2-methyl-propan-1-one (IRGACURE® 127); 2-hydroxy-1-{4-[4-(2-hydroxy-2-methyl-propionyl)-phenoxy]-phenyl}-2-methyl-propan-1-one; dialkoxyacetophenones, α-hydroxy- or α-aminoacetophenones, e.g. (4-methylthiobenzoyl)-1-methyl-1-morpholinoethane (IRGACURE® 907), (4-morpholinobenzoyl)-1-benzyl-1-dimethylaminopropane (IRGACURE® 369), (4-morpholinobenzoyl)-1-(4-methylbenzyl)-1-dimethylaminopropane (IRGACURE® 379), (4-(2-hydroxyethyl)aminobenzoyl)-1-benzyl-1-dimethylaminopropane), (3,4-dimethoxybenzoyl)-1-benzyl-1-dimethylaminopropane; 4-aroyl-1,3-dioxolanes, benzoin alkyl ethers and benzil ketals, e.g. dimethyl benzil ketal, phenylglyoxalic esters and derivatives thereof, e.g. oxo-phenyl-acetic acid 2-(2-hydroxy-ethoxy)-ethyl ester, dimeric phenylglyoxalic esters, e.g. oxo-phenyl-acetic acid 1-methyl-2-[2-(2-oxo-2-phenyl-acetoxy)-propoxy]-ethyl ester (IRGACURE® 754); oximeesters, e.g. 1,2-octanedione 1-[4-(phenylthio)phenyl]-2-(O-benzoyloxime) (IRGACURE® OXE01), ethanone 1-[9-ethyl-6-(2-methylbenzoyl)-9H-carbazol-3-yl]-1-(O-acetyloxime) (IRGACURE® OXE02), 9H-thioxanthene-2-carboxaldehyde 9-oxo-2-(O-acetyloxime), peresters, e.g. benzophenone tetracarboxylic peresters as described for example in EP 126541, monoacyl phosphine oxides, e.g. (2,4,6-trimethylbenzoyl)diphenylphosphine oxide (DAROCUR® TPO), ethyl (2,4,6-trimethylbenzoyl phenyl) phosphinic acid ester; bisacylphosphine oxides, e.g. bis(2,6-dimethoxy-benzoyl)-(2,4,4-trimethyl-pentyl)phosphine oxide, bis(2,4,6-trimethylbenzoyl)-phenylphosphine oxide (IRGACURE® 819), bis(2,4,6-trimethylbenzoyl)-2,4-dipentoxyphenylphosphine oxide, trisacylphosphine oxides, halomethyl-triazines, e.g. 2-[2-(4-methoxy-phenyl)-vinyl]-4,6-bis-trichloromethyl[1,3,5]triazine, 2-(4-methoxy-phenyl)-4,6-bis-trichloromethyl[1,3,5]triazine, 2-(3,4-dimethoxy-phenyl)-4,6-bis-trichloromethyl-[1,3,5]triazine, 2-methyl-4,6-bis-trichloromethyl[1,3,5]triazine, hexaarylbisimidazole/coinitiators systems, e.g. ortho-chlorohexaphenyl-bisimidazole combined with 2-mercaptobenzthiazole, ferrocenium compounds, or titanocenes, e.g. bis(cyclopentadien-yl)-bis(2,6-difluoro-3-pyrryl-phenyl)titanium (IRGACURE® 784). Further, borate compounds, as for example described in U.S. Pat. No. 4,772,530, EP775706, GB2307474, GB2307473 and GB 2304472. The borate compounds preferably are used in combination with electron acceptor compounds, such as, for example dye cations, or thioxanthone derivatives.

The DAROCUR® and IRGACURE® compounds are available from Ciba Inc., now part of BASF.

Further examples of additional photoinitiators are peroxide compounds, e.g. benzoyl peroxide (other suitable peroxides are described in U.S. Pat. No. 4,950,581, col. 19, l. 17-25) or cationic photoinitiators, such as aromatic sulfonium or iodonium salts, such as those to be found in U.S. Pat. No. 4,950,581, col. 18, l. 60 to col. 19, l. 10, or cyclopentadienyl-arene-iron(II) complex salts, for example ($\eta^6$-isopropylbenzene) ($\eta^5$-cyclopentadienyl)iron(II) hexafluorophosphate.

The compositions can also comprise thermally curable component as additional additives (c). Examples of component (c) include oligomers and/or polymers derived from α,β-unsaturated acids and derivatives thereof, for example polyacrylates and polymethacrylates, polymethyl methacrylates impact-resistant-modified with butyl acrylate, polyacrylamides and polyacrylonitriles. Further examples of component (c) are urethanes, polyurethanes derived on the one hand from polyethers, polyesters and polyacrylates having free hydroxyl groups and on the other hand from aliphatic or aromatic polyisocyanates, and educts thereof. Component (c) accordingly also includes, for example, crosslinkable acrylic resins derived from substituted acrylic acid esters, for example epoxy acrylates, urethane acrylates and polyester acrylates. Alkyd resins, polyester resins and acrylate resins and modifications thereof that are crosslinked with melamine resins, urea resins, isocyanates, isocyanurates, polyisocyanates, polyisocyanurates and epoxy resins, may also be a constituent of component (c). Component (c) is, for example, generally a film-forming binder based on a thermoplastic or thermocurable resin, especially on a thermocurable resin. Examples thereof are alkyd, acrylic, polyester, phenolic, melamine, epoxy and polyurethane resins and mixtures thereof. Examples thereof can be found, for example, in Ullmann's Encyclopedia of Industrial Chemistry, 5th Ed., Vol. A18, pp. 368-426, VCH, Weinheim 1991.

Component (c) may also be a cold-curable or hot-curable binder, in which case the addition of a curing catalyst may be advantageous. Suitable catalysts that accelerate the full cure of the binder can be found, for example, in Ullmann's Encyclopedia of Industrial Chemistry, Vol. A18, page 469, VCH Verlagsgesellschaft, Weinheim 1991.

Specific examples of binders suitable as component (c) are:
1. surface-coatings based on cold- or hot-crosslinkable alkyd, acrylate, polyester, epoxy or melamine resins or mixtures of such resins, optionally with the addition of a curing catalyst;
2. two-component polyurethane surface-coatings based on hydroxyl-group-containing acrylate, polyester or polyether resins and aliphatic or aromatic isocyanates, isocyanurates or polyisocyanates;
3. one-component polyurethane surface-coatings based on blocked isocyanates, isocyanurates or polyisocyanates, which are de-blocked during heating; it is also possible to add melamine resins as appropriate;
4. one-component polyurethane surface-coatings based on aliphatic or aromatic urethanes or polyurethanes and hydroxyl-group-containing acrylate, polyester or polyether resins;
5. one-component polyurethane surface-coatings based on aliphatic or aromatic urethane acrylates or polyurethane acrylates having free amine groups in the urethane structure and melamine resins or polyether resins, optionally with the addition of a curing catalyst;
6. two-component surface-coatings based on (poly)ketimines and aliphatic or aromatic isocyanates, isocyanurates or polyisocyanates;
7. two-component surface-coatings based on (poly)ketimines and an unsaturated acrylate resin or a polyacetoacetate resin or a methacrylamidoglycolate methyl ester;
8. two-component surface-coatings based on carboxyl- or amino-group-containing poly-acrylates and polyepoxides;
9. two-component surface-coatings based on anhydride-group-containing acrylate resins and a polyhydroxy or polyamino component;
10. two-component surface-coatings based on acrylate-containing anhydrides and polyepoxides;
11. two-component surface-coatings based on (poly)oxazolines and anhydride-group-containing acrylate resins or unsaturated acrylate resins or aliphatic or aromatic isocyanates, isocyanurates or polyisocyanates;
12. two-component surface-coatings based on unsaturated polyacrylates and polymalonates;
13. thermoplastic polyacrylate surface-coatings based on thermoplastic acrylate resins or extrinsically crosslinking acrylate resins in combination with etherified melamine resins;
14. surface-coating systems based on urethane(meth)acrylate having (meth)acryloyl groups and free isocyanate groups and on one or more compounds that react with iso-cyanates, for example free or esterified polyols. Such systems have been published, for example, in EP928800.

Blocked isocyanates that can also be used as component (c) are described, for example, in Organischer Metallschutz: Entwicklung and Anwendung von Beschichtungsstoffen, pages 159-160, Vincentz Verlag, Hanover (1993). These are compounds in which the highly reactive NCO group is "blocked" by reaction with specific radicals, for example a primary alcohol, phenol, acetic acid ethyl ester, ∈-caprolactam, phthalimide, imidazole, oxime or amine. The blocked isocyanate is stable in liquid systems and also in the presence of hydroxy groups. Upon heating, the blocking group (protecting group) is removed again and the NCO group is freed.

1-Component and 2-component systems may be used as component (c). Examples of such systems are described in Ullmann's Encyclopedia of Industrial Chemistry, Vol. A18, Paints and Coatings, pages 404-407, VCH Verlagsgesellschaft mbH, Weinheim (1991).

It is possible to optimise the composition by specific adaptation, for example by varying the binder/crosslinking agent ratios. Such measures will be known to the person skilled in the art and are customary in coating technology.

In the curing process according to the invention, component (c) is preferably a mixture based on acrylate/melamine (and melamine derivatives), 2-component polyurethane, 1-component polyurethane, 2-component epoxy/carboxy or 1-component epoxy/carboxy. Mixtures of such systems are also possible, for example the addition of melamine (or derivatives thereof) to 1-component polyurethanes.

Component (c) is preferably a binder based on a polyacrylate with melamine or on a melamine derivative or a system based on a polyacrylate and/or polyester polyol with an unblocked polyisocyanate or polyisocyanurate.

Component (c) may also comprise monomeric and/or oligomeric compounds having ethylenically unsaturated bonds (prepolymers) that additionally contain at least one or more OH, $NH_2$, COOH, epoxy or NCO group(s) (=c1) that are capable of reaction with the binder and/or the crosslinking agent constituent of component (c). After application and thermal curing, the ethylenically unsaturated bonds are converted to a crosslinked, high molecular weight form by irradiation with UV light. Examples of such components (c) are described, for example, in the above-mentioned publication, Ullmann's Encyclopedia of Industrial Chemistry, 5th Ed., Vol. A18, pages 451-453, or by S. Urano, K. Aoki, N. Tsuboniva and R. Mizuguchi in Progress in Organic Coatings, 20 (1992), 471-486, or by H. Terashima and O. Isozaki in JOCCA 1992 (6), 222.

(c1) may, for example, also be an OH-group-containing unsaturated acrylate, for example hydroxyethyl or hydroxybutyl acrylate or a glycidyl acrylate. Component (c1) may be of any desired structure (for example it may contain units of polyester, polyacrylate, polyether, etc.), provided that it contains an ethylenically unsaturated double bond and additionally free OH, COOH, $NH_2$, epoxy or NCO groups.

(c1) may, for example, also be obtained by reacting an epoxy-functional oligomer with acrylic acid or methacrylic acid. A typical example of an OH-functional oligomer having vinylic double bonds is

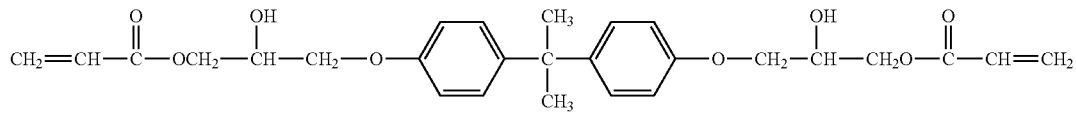

obtained by reaction of CH$_2$=CHCOOH with

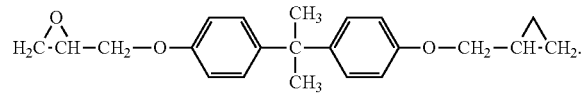

Another possible method of obtaining component (c1) is, for example, the reaction of an oligomer that contains only one epoxy group and has a free OH group at another position in the molecule.

The quantity ratio of the free-radically radiation-curable-polymerisable components to the thermally polymerisable component (c) in the UV- and thermally-crosslinkable formulations is not critical. "Dual-cure" systems are known to the person skilled in the art, who will therefore be familiar with the optimum mixing ratios of the free-radically- and thermally-crosslinkable components according to the intended use. For example, the ratio can be in the range from 5:95 to 95:5, from 20:80 to 80:20 or from 30:70 to 70:30, for example from 40:60 to 60:40. Examples of "dual-cure" systems, that is to say systems comprising both radiation-curable and thermally curable components, can be found inter alia in U.S. Pat. No. 5,922,473, columns 6 to 10.

The surface coatings may be solutions or dispersions of the surface-coating resin in an organic solvent or in water, but they may also be solventless. Of special interest are surface coatings having a low solvent content, so-called "high solids surface coatings", and powder coating compositions. The surface coatings may be clear lacquers, as used, for example, in the automobile industry as finishing lacquers for multilayer coatings. They may also comprise pigments and/or fillers, which may be inorganic or organic compounds, and metal powders for metal effect finishes.

The surface coatings may also comprise relatively small amounts of special additives customary in surface-coating technology, for example flow improvers, thixotropic agents, leveling agents, antifoaming agents, wetting agents, adhesion promoters, light stabilisers, antioxidants, or sensitisers.

UV absorbers, such as those of the hydroxyphenyl-benzotriazole, hydroxyphenyl-benzophenone, oxalic acid amide or hydroxyphenyl-s-triazine type may be added to the compositions according to the invention as light stabilisers. Individual compounds or mixtures of those compounds can be used with or without the addition of sterically hindered amines (HALS).

Examples of such UV absorbers and light stabilisers are 1. 2-(2'-Hydroxyphenyl)-benzotriazoles, such as 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)-benzotriazole, 2-(2'-hydroxy-5'-(1,1,3,3-tetramethylbutyl)phenyl)-benzotriazole, 2-(3',5'-di-t-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)-benzotriazole, 2-(2'-hydroxy-4'-octyloxyphenyl)-benzotriazole, 2-(3',5'-di-tert-amyl-2'-hydroxyphenyl)-benzotriazole, 2-(3',5'-bis-(α,α-dimethylbenzyl)-2'-hydroxyphenyl)-benzotriazole, mixture of 2-(3'-tert-butyl-2'-hydroxy-5'-(2-octyloxycarbonylethyl)phenyl)-5-chloro-benzotriazole, 2-(3'-t-butyl-5'-[2-(2-ethyl-hexyloxy)-carbonylethyl]-2'-hydroxyphenyl)-5-chloro-benzotriazole, 2-(3'-tertbutyl-2'-hydroxy-5'-(2-methoxycarbonylethyl)phenyl)-5-chloro-benzotriazole, 2(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)carbonylethyl]-2'-hydroxyphenylybenzotriazole, 2-(3'-dodecyl-2'-hydroxy-5'-methylphenyl)-benzotriazole and 2-(3'-tert-butyl-2'-hydroxy-5'-(2-isooctyloxycarbonylethyl) phenyl-benzotriazole, 2,2'-methylene-bis[4-(1,1,3,3-tetramethylbutyl)-6-benzotriazol-2-yl-phenol]; transesterification product of 2-[3'-tert-butyl-5'-(2-methoxycarbonylethyl)-2'-hydroxy-phenyl]-benzotriazole with polyethylene glycol 300; [R—CH$_2$CH$_2$—COO(CH$_2$)$_3$]$_2$—wherein R=3'-tert-butyl-4'-hydroxy-5'-2H-benzotriazol-2-yl-phenyl.

2. 2-Hydroxybenzophenones, such as the 4-hydroxy, 4-methoxy, 4-octyloxy, 4-decyloxy, 4-dodecyloxy, 4-benzyloxy, 4,2',4'-trihydroxy or 2'-hydroxy-4,4'-dimethoxy derivative.

3. Esters of unsubstituted or substituted benzoic acids, such as 4-tert-butyl-phenyl salicylate, phenyl salicylate, octylphenyl salicylate, dibenzoylresorcinol, bis(4-tert-butylbenzoyl) resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butyl-4-hydroxybenzoic acid octadecyl ester, 3,5-di-tert-butyl-4-hydroxybenzoic acid 2-methyl-4,6-di-tert-butylphenyl ester.

4. Acrylates, such as α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(b-carbomethoxy-β-cyanovinyl)-2-methyl-indoline.

5. Sterically hindered amines, such as bis(2,2,6,6-tetramethyl-piperidyl)sebacate, bis(2,2,6,-6-tetramethyl-piperidyl) succinate, bis(1,2,2,6,6-pentamethylpiperidyl)sebacate, n-butyl-3,-5-di-tert-butyl-4-hydroxybenzyl-malonic acid bis (1,2,2,6,6-pentamethylpiperidyl) ester, condensation product of 1-hydroxyethyl-2,2,6,6-tetramethyl-4-hydroxypiperidine and succinic acid, condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2,6, 6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5] decane-2,4-dione, bis(1-octyloxy-2,2,6,6-tetramethylpiperidyl)sebacate, bis(1-octyloxy-2,2,6,6-tetramethylpiperidyl)succinate, condensation product of N,N'-bis(2,2,6,6-tetra-methyl-4-piperidyl)-hexamethylenediamine and 4-morpholino-2,6-dichloro-1,3,5-triazine, condensation product of 2-chloro-4,6-di(4-n-butylamino-2,2,6, 6-tetramethylpiperidyl)-1,3,5-triazine and 1,2-bis(3- aminopropylamino)ethane, condensation product of 2-chloro-4,6-di(4-n-butylamino1,2,2,6,6-pentamethylpiperidyl)-1,3,5-triazine and 1,2-bis(3-aminopropylamino) ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)-pyrrolidine-2,5-dione.

6. Oxalic acid diamides, such as 4,4'-dioctyloxy-oxanilide, 2,2'-diethoxy-oxanilide, 2,2'-di-octyloxy-5,5'-di-tert-butyloxanilide, 2,2'-didodecyloxy-5,5'-di-tert-butyl-oxanilide, 2-ethoxy-2'-ethyl-oxanilide, N,N'-bis(3-dimethylaminopropyl)oxalamide, 2-ethoxy-5-tert-butyl-2'-ethyl-oxanilide and a mixture thereof with 2-ethoxy-2'-ethyl-5,4'-di-tert-butyl-oxanilide, mixtures of o- and p-methoxy- and of o- and p-ethoxy-di-substituted oxanilides.

7. 2-(2-Hydroxyphenyl)-1,3,5-triazines, such as 2,4,6-tris (2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxy-phenyl)-6-(2, 4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)phenyl]-4,6-bis(2,4-dimethyl-phenyl)-1, 3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl-/tridecyl-oxy-(2-hydroxypropyl)oxy-2-hydroxy-phenyl]-4,6-bis(2,4-dimethylphenyl)-1,3,5-triazine.

8. Phosphites and phosphonites, such as triphenyl phosphite, diphenyl alkyl phosphites, phenyl dialkyl phosphites, tris(nonylphenyl) phosphite, trilauryl phosphite, trioctadecyl phosphite, distearyl-pentaerythritol diphosphite, tris(2,4-di-tert-butylphenyl) phosphite, diisodecylpentaerythritol diphosphite, bis(2,4-di-tert-butylphenyl)pentaerythritol diphosphite, bis(2,6-di-tertbutyl-4-methylphenyl)pentaerythritol diphosphite, bis-isodecyloxy-pentaerythritol diphosphite, bis(2,4-di-tert-butyl-6-methylphenyl)pentaerythritol diphosphite, bis-(2,4,6-tri-tert-butylphenyl)pentaerythritol diphosphite, tristearyl-sorbitol triphosphite, tetrakis(2,4-di-tert-butylphenyl)-4,4'-biphenylene diphosphonite, 6-isooctyloxy-2,4,8,10-tetra-tert-butyl-12H-dibenzo-[d,g]-1,3,2-dioxaphosphocine, 6-fluoro-2,4,8,10-tetra-tert-butyl-12-methyl-dibenzo[d,g]-1,3,-2-dioxaphosphocine, bis(2,4-di-tert-butyl-6-methylphenyl)methyl phosphite, bis(2,4-di-tert-butyl-6-methylphenyl)ethyl phosphite.

Such light stabilisers can also be added, for example, to an adjacent surface-coating layer from which they gradually diffuse into the layer of stoving lacquer to be protected. The adjacent surface-coating layer may be a primer under the stoving lacquer or a finishing lacquer over the stoving lacquer.

It is also possible to add to the resin, for example, photosensitisers which shift or increase the spectral sensitivity so that the irradiation period can be reduced and/or other light sources can be used. Examples of photosensitisers are aromatic ketones or aromatic aldehydes (as described, for example, in U.S. Pat. No. 4,017,652), 3-acyl-coumarins (as described, for example, in U.S. Pat. No. 4,366,228, EP738928, EP022188), keto-coumarines (as described e.g. in U.S. Pat. No. 5,534,633, EP 538997, JP08-272095A), styryl-coumarines (as described e.g. in EP624580), 3-(aroylmethylene)-thiazolines, thioxanthones, condensed aromatic compounds, such as perylene, aromatic amines (as described, for example, in U.S. Pat. No. 4,069,954 or WO96/41237) or cationic and basic colourants (as described, for example, in U.S. Pat. No. 4,026,705), for example eosine, rhodanine and erythrosine colourants, as well as dyes and pigments as described for example in JP08-320551A, EP747771, JP07-036179A, EP619520, JP06-161109A, JP06-043641A, JP06-035198A, WO93/15440, EP568993, JP05-005005, JP05-027432A, JP05-301910A, JP04-014083A, JP04-294148A, EP359431, EP103294, U.S. Pat. No. 4,282,309, EP039025, EP005274, EP727713, EP726497 or DE2027467.

Other customary additives are—depending on the intended use—optical brighteners, fillers, pigments, colourants, wetting agents or flow improvers and adhesion promoters.

For curing thick and pigmented coatings, the addition of micro glass beads or powdered glass fibres, as described in U.S. Pat. No. 5,013,768, is suitable.

Sulfonium salt derivatives can also be used, for example, in hybrid systems. These systems are based on formulations that are fully cured by two different reaction mechanisms. Examples thereof are systems that comprise components that are capable of undergoing an acid-catalysed crosslinking reaction or polymerisation reaction, but that also comprise further components that crosslink by a second mechanism. Examples of the second mechanism are radical full cure, oxidative crosslinking or humidity-initiated crosslinking. The second curing mechanism may be initiated purely thermally, if necessary with a suitable catalyst, or also by means of light using a second photoinitiator. Suitable additional photoinitiators are described above.

If the composition comprises a radically crosslinkable component, the curing process, especially of compositions that are pigmented (for example with titanium dioxide), can also be assisted by the addition of a component that is radical-forming under thermal conditions, such as an azo compound, for example 2,2'-azobis(4-methoxy-2,4-dimethylvaleronitrile), a triazene, a diazosulfide, a pentazadiene or a peroxy compound, such as, for example, a hydroperoxide or peroxycarbonate, for example tert-butyl hydroperoxide, as described, for example, in EP245639. The addition of redox initiators, such as cobalt salts, enables the curing to be assisted by oxidative crosslinking with oxygen from the air.

The surface coating can be applied by one of the methods customary in the art, for example by spraying, painting or immersion. When suitable surface coatings are used, electrical application, for example by anodic electrophoretic deposition, is also possible. After drying, the surface coating film is irradiated. If necessary, the surface coating film is then fully cured by means of heat treatment.

The compounds of formula I can also be used for curing mouldings made from composites. A composite consists of a self-supporting matrix material, for example a glass fibre fabric, impregnated with the photocuring formulation.

It is known from EP592139 that sulfonate derivatives can be used as acid generators, which can be activated by light in compositions that are suitable for the surface treatment and cleaning of glass, aluminium and steel surfaces. The use of such compounds in organosilane systems results in compositions that have significantly better storage stability than those obtained when the free acid is used. The compounds of formula I are also suitable for this application.

The sulfonium salt derivatives of the present invention can also be used to shape polymers that undergo an acid induced transition into a state where they have the required properties using photolithography. For instance the sulfonium salt derivatives can be used to pattern conjugated emissive polymers as described, for example, in M. L. Renak; C. Bazan; D. Roitman; Advanced materials 1997, 9, 392. Such patterned emissive polymers can be used to manufacture microscalar patterned Light Emitting Diodes (LED) which can be used to manufacture displays and data storage media. In a similar way precursors for polyimides (e.g. polyimid precursors with acid labile protecting groups that change solubility in the developer) can be irradiated to form patterned polyimide layers which can serve as protective coatings, insulating layers and buffer layers in the production of microchips and printed circuit boards.

The formulations of the invention may also be used as conformal coatings, photoimagable insulating layers and dielectrics as they are used in sequential build up systems for printed circuit boards, stress buffer layers in the manufacturing of integrated circuits.

It is known that conjugated polymers like, e.g. polyanilines can be converted from semiconductive to conductive state by means of proton doping. The sulfonium salt derivatives of the present invention can also be used to imagewise irradiate compositions comprising such conjugated polymers in order to form conducting structures (exposed areas) embedded in insulating material (non exposed areas). These materials can be used as wiring and connecting parts for the production of electric and electronic devices.

Suitable radiation sources for the compositions comprising compounds of formula I are radiation sources that emit radiation of a wavelength of approximately from 10 to 1500, for example from 10 to 1000, or preferably from 10 to 700 nanometers as well as e-beam radiation and high-energy electromagnetic radiation such as X-rays. Both, point sources and planiform projectors (lamp carpets) are suitable. Examples are: carbon arc lamps, xenon arc lamps, medium pressure, high pressure and low pressure mercury lamps, optionally doped with metal halides (metal halide lamps), microwave-excited metal vapour lamps, excimer lamps, superactinic fluorescent tubes, fluorescent lamps, argon filament lamps, electronic flash lamps, photographic flood lights, electron beams and X-ray beams generated by means of synchrotrons or laser plasma. The distance between the radiation source and the substrate according to the invention to be irradiated can vary, for example, from 2 cm to 150 cm, according to the intended use and the type and/or strength of the radiation source. Suitable radiaiton sources are especially mercury vapour lamps, especially medium and high pressure mercury lamps, from the radiation of which emission lines at other wavelengths can, if desired, be filtered out. That is especially the case for relatively short wavelength radiation. It is, however, also possible to use low energy lamps (for example fluorescent tubes) that are capable of emitting in the appropriate wavelength range. An example thereof is the Philips TL03 lamp. Another type of radiation source that can be used are the light emitting diodes (LED) that emitt at different wavelengths throughout the whole spectrum either as small band emitting source or as broad band (white light) source. Also suitable are laser radiation sources, for example excimer lasers, such as Kr—F lasers for irradiation at 248 nm, Ar—F lasers at 193 nm, or $F_2$ laser at 157 nm. Lasers in the visible range and in the infrared range can also be used. Especially suitable is radiation of the mercury i, h and g lines at wavelengths of 365, 405 and 436 nanometers. As a light source further EUV (Extreme Ultra Violet) at 13 nm is also suitable. A suitable laser-beam source is, for example, the argon-ion laser, which emits radiation at wavelengths of 454, 458, 466, 472, 478, 488 and 514 nanometers. Nd-YAG-lasers emitting light at 1064 nm and its second and third harmonic (532 nm and 355 nm respectively) can also be used. Also suitable is, for example, a helium/cadmium laser having an emission at 442 nm or lasers that emit in the UV range. With that type of irradiation, it is not absolutely essential to use a photomask in contact with the photopolymeric coating to produce a positive or negative resist; the controlled laser beam is capable of writing directly onto the coating. For that purpose the high sensitivity of the materials according to the invention is very advantageous, allowing high writing speeds at relatively low intensities.

On irradiation, the sulfonium salt derivatives in the composition in the irradiated sections of the surface coating decompose to form the acids.

In contrast to customary UV curing with high-intensity radiation, with the compounds according to the invention activation is achieved under the action of radiation of relatively low intensity. Such radiation includes, for example, daylight (sunlight), and radiation sources equivalent to daylight. Sunlight differs in spectral composition and intensity from the light of the artificial radiation sources customarily used in UV curing. The absorption characteristics of the compounds according to the invention are as well suitable for exploiting sunlight as a natural source of radiation for curing. Daylight-equivalent artificial light sources that can be used to activate the compounds according to the invention are to be understood as being projectors of low intensity, such as certain fluorescent lamps, for example the Philips TL05 special fluorescent lamp or the Philips TL09 special fluorescent lamp. Lamps having a high daylight content and daylight itself are especially capable of curing the surface of a surface-coating layer satisfactorily in a tack-free manner. In that case expensive curing apparatus is superfluous and the compositions can be used especially for exterior finishes. Curing with daylight or daylight-equivalent light sources is an energy-saving method and prevents emissions of volatile organic components in exterior applications. In contrast to the conveyor belt method, which is suitable for flat components, daylight curing can also be used for exterior finishes on static or fixed articles and structures.

The surface coating to be cured can be exposed directly to sunlight or daylight-equivalent light sources. The curing can, however, also take place behind a transparent layer (e.g. a pane of glass or a sheet of plastics).

The examples, which follow, illustrate the invention in more detail. Parts and percentages are, as in the remainder of the description, by weight, unless stated otherwise. Where alkyl radicals having more than three carbon atoms are referred to without any mention of specific isomers, the n-isomers are meant in each case.

EXAMPLE 1

Preparation of

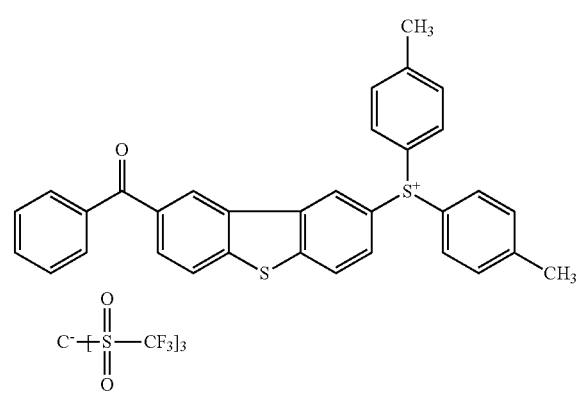

5 g (17.3 mmol) of 2-benzoyldibenzothiophene, 3.98 g (17.3 mmol) of p-tolylsulfoxide, 17.5 ml of acetic anhydride, 17.5 ml of acetic acid and 4.3 ml of CH$_2$Cl$_2$ are mixed in 200 ml three-necked flask under a nitrogen atomosphere and cooled by ice bath. To the suspension, 6.5 ml of sulfuric acid is added dropwise during 15 min with keeping the temperature below 10° C. The reaction mixture is stirred at room temperature for 18 hours, followed by at 50° C. for 7 hours. After the reaction mixture is cooled by ice bath, 8.5 g (20.8 mmol) of 58.5% aqueous solution of tris(trifluoromethanesulfonyl)methane is added with cooled. The reaction mixture is stirred at room temperature overnight, poured into water, and extracted with CH$_2$Cl$_2$. The organic phase is washed with water, dried over MgSO$_4$, and concentrated. The residue is purified by column chromatography using tert-butylmethylether/ethyl acetate (3:1) as eluent, yielding the title compound of example 1 as a pale yellow sold with melting point of 55° C.

The structure is confirmed by the $^1$H-NMR spectrum (CDCl$_3$). δ [ppm]: 2.50 (s, 6H), 7.47-7.60 (m, 10H), 7.60-7.70 (m, 2H), 7.83 (d, 2H), 7.97-8.06 (m, 2H), 8.24 (d, 1H), 8.35 (s, 1H), 8.57 (s, 1H); $^{19}$F-NMR (CDCl$_3$) δ-76.84 (s, 9F).

EXAMPLE 2

Preparation of

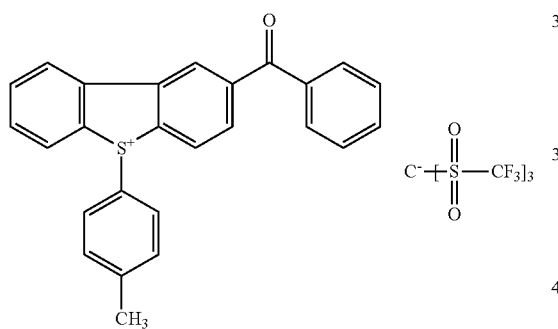

1.92 g of P$_2$O$_5$ is added to 13.1 ml of methanesulfonic acid and stirred at room temperature for hour under a nitrogen atomosphere. To the solution, 1.13 g (3.7 mmol) of 2-benzoyl-dibenzothiophene-5-oxide and 0.79 ml of toluene (7.4 mmol) are added and stirred at room temperature overnight. After the reaction mixture is cooled by ice bath, 1.81 g (4.4 mmol) of 58.5% aqueous solution of tris(trifluoromethanesulfonyl)methane is added with cooled, followed by addition of 15 ml of CH$_2$Cl$_2$. The reaction mixture is stirred at room temperature for 5 hours, poured into water, and extracted with CH$_2$Cl$_2$. The organic phase is washed with water, dried over MgSO$_4$, and concentrated. The residue is purified by column chromatography using CH$_2$Cl$_2$ as eluent, yielding the title compound of example 2 as a brownish sold with melting point of 77-78° C.

The structure is confirmed by the $^1$H-NMR spectrum (CDCl$_3$). δ [ppm]: 2.43 (s, 3H), 7.40 (d, 2H), 7.47 (d, 2H), 7.57 (t, 2H), 7.67-7.81 (m, 2H), 7.86 (d, 2H), 7.92-8.06 (m, 3H), 8.12 (d, 1H), 8.24 (d, 1H), 8.54 (s, 1H); $^{19}$F-NMR (CDCl$_3$) δ-76.82 (s, 9F).

EXAMPLE 3

Preparation of

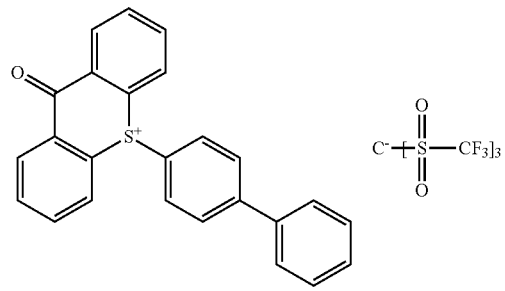

1.71 g (7.5 mmol) of thioxanthene-9-one-10-oxide and 1.60 g (10.4 mmol) of biphenyl are added to 7 ml of acetic acid at 15° C. 7 ml of acetic anhydride and 1.75 ml of CH$_2$Cl$_2$ are added to the mixture followed by addition of 2.6 ml of H$_2$SO$_4$, and the mixture is stirred at 15° C. for 2 hours. After the reaction mixture is cooled by ice bath, 3.71 g (9 mmol) of 58.5% aqueous solution of tris(trifluoromethanesulfonyl)methane is added to the reaction mixture the mixture is stirred for 5 hours. poured into water, and extracted with CH$_2$Cl$_2$. The organic phase is washed with water, dried over MgSO$_4$, and concentrated. The residue is purified by column chromatography using CH$_2$Cl$_2$/MeOH (20:1) as eluent, yielding the title compound of example 3 as a brown powder.

The structure is confirmed by the $^1$H-NMR spectrum (DMSO-d$_6$) δ [ppm] 7.40-7.49 (m, 3H), 7.69 (d, 2H), 7.91 (d, 2H), 7.99-8.00 (m, 4H), 8.05 (d, 2H), 8.16-8.17 (m, 2H), 8.57-8.58 (m, 2H); $^{19}$F-NMR (DMSO-d$_6$) δ-76.40 (s, 9F)

EXAMPLE 4

Preparation of

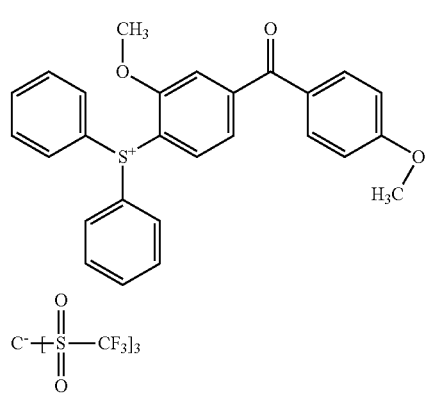

3.0 g of P$_2$O$_5$ is added to 20 ml of methanesulfonic acid and stirred at room temperature for 1 hour under a nitrogen atomosphere. To the solution, 2.25 g (11.1 mmol) of diphenylsulfoxide and 2.7 g (11.1 mmol) of 3,4'-dimethoxybenzophenone are added and stirred at room temperature overnight., followed by at 50° C. for 3.5 hours. After the reaction mixture is cooled by ice bath, 5.6 g (13.8 mmol) of 58.5% aqueous solution of tris(trifluoromethanesulfonyl)methane is added with cooled, followed by addition of 15 ml of CH$_2$Cl$_2$. The reaction mixture is stirred at room temperature for 5 hours, poured into water, and extracted with CH$_2$Cl$_2$. The organic phase is washed with water, dried over MgSO$_4$, and concentrated. The residue is purified by column chromatography using tert-butylmethylether/ethyl acetate (2:1) as eluent, yielding the title compound of example 4 as a brownish oil.

The structure is confirmed by the $^1$H-NMR spectrum (CDCl$_3$). δ [ppm]: 3.92 (s, 3H), 3.94 (s, 3H), 7.02 (d, 2H), 7.38-7.46 (m, 3H), 7.53 (d, 4H), 7.69-7.87 (m, 8H); $^{19}$F-NMR (CDCl$_3$) δ-76.84 (s, 9F).

APPLICATION EXAMPLES

Example A1

A chemically amplified negative resist formulation is prepared by mixing the following components:
100.00 parts of an epoxy resin (SU-8 R 2002 provided by MicroChem., USA)
245.00 parts of cyclopentanone (ibidem)
5.00 parts of the photoacid generator (PAG) of examples The resist formulation is spin-coated onto a silicone wafer, on which chemical treatment with hexamethyldisilazane is applied beforehand, and soft-baked for 60 seconds at 95° C. on a hotplate to obtain a film thickness of 2 µm. The resist film is then exposed to UV radiation through V-42 and UV-D35 filters (provided by Asahi Technoglass, Japan) and a multi-density quartz mask using an Ushio's high-pressure mercury lamp, HB-25106AP, and a mask aligner Canon PLA-501F. The samples then are post-exposure-baked for 120 seconds at 95° C. on a hotplate and developed. The dose (E$_{1:1}$), which is the dose just sufficient to give the same resist thickness after 60 seconds immersion development in ethyl lactate as the one before exposure, is determined from the measured contrast curve. The smaller the required dose the higher sensitive is the resist formulation. The results are summarized in Table 1.

TABLE 1

| PAG | E$_{1:1}$ (mJ/cm$^2$) |
|---|---|
| Example 1 | 54 |
| Example 2 | 18 |
| Example 3 | 13 |
| Example 4 | 38 |

The invention claimed is:
1. A compound of the formula I

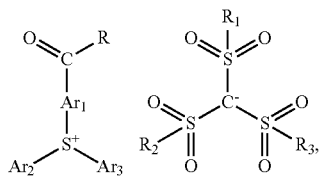

wherein
Ar$_1$ is phenylene, naphthylene, or heteroarylene,
wherein the phenylene, naphthylene, or heteroarylene, are unsubstituted or are substituted by one or more C$_3$-C$_{30}$cycloalkyl, C$_1$-C$_{18}$alkyl, C$_1$-C$_{10}$haloalkyl, C$_2$-C$_{12}$alkenyl, C$_4$-C$_{30}$cycloalkenyl, phenyl-C$_1$-C$_3$-alkyl,
or are substituted by C$_2$-C$_{18}$alkyl which is interrupted by one or more O, S, NR$_7$, O(CO), (CO)O, (CO)NR$_7$ or NR$_7$(CO),
or are substituted by C$_3$-C$_{30}$cycloalkyl which is interrupted by one or more O, S, NR$_7$, O(CO), (CO)O, (CO)NR$_7$ or NR$_7$(CO),
or are substituted by C$_4$-C$_{30}$cycloalkenyl which is interrupted by one or more O, S, NR$_7$, O(CO), (CO)O, (CO)NR$_7$ or NR$_7$(CO),
or are substituted by one or more halogen, NO$_2$, CN, Ar, (CO)R$_8$, (CO)OR$_4$, (CO)NR$_5$R$_6$, O(CO)R$_8$, O(CO)OR$_4$, O(CO)NR$_5$R$_6$, NR$_7$(CO)R$_8$, NR$_7$(CO)OR$_4$, OR$_4$, NR$_5$R$_6$, SR$_7$, SOR$_8$, SO$_2$R$_8$ or —OSO$_2$R$_8$,
wherein optionally the substituents C$_1$-C$_{18}$alkyl, C$_2$-C$_{12}$alkenyl, (CO)R$_8$, (CO)OR$_4$, (CO)NR$_5$R$_6$, O(CO)R$_8$, O(CO)OR$_4$, O(CO)NR$_5$R$_6$, NR$_7$(CO)R$_8$, NR$_7$(CO)OR$_4$, OR$_4$, NR$_5$R$_6$, SR$_7$, SOR$_8$, SO$_2$R$_8$ or OSO$_2$R$_8$ form 5-, 6- or 7-membered rings, via the radicals C$_1$-C$_{18}$alkyl, C$_2$-C$_{12}$alkenyl, R$_4$, R$_5$, R$_6$, R$_7$ and/or R$_8$, with further substituents on the phenylene, naphthylene, or heteroarylene, or with one of the carbon atoms of the phenylene, naphthylene, or heteroarylene;
wherein all Ar$_1$ optionally additionally are substituted by a group having a —O—C-bond or a —O—Si-bond which cleaves upon the action of an acid;
Ar$_2$ and Ar$_3$ independently of each other are phenyl, naphthyl, biphenylyl or heteroaryl, wherein the phenyl, naphthyl, biphenylyl or heteroaryl are unsubstituted or are substituted by one or more C$_3$-C$_{30}$cycloalkyl, C$_1$-C$_{18}$alkyl, C$_1$-C$_{10}$haloalkyl, C$_2$-C$_{12}$alkenyl, C$_4$-C$_{30}$cycloalkenyl, phenyl-C$_1$-C$_3$-alkyl,
or by C$_2$-C$_{18}$alkyl which is interrupted by one or more O, S, NR$_7$, O(CO), (CO)O, (CO)NR$_7$ or NR$_7$(CO),
or by C$_3$-C$_{30}$cycloalkyl which is interrupted by one or more O, S, NR$_7$, O(CO), (CO)O, (CO)NR$_7$ or NR$_7$(CO),
or by C$_4$-C$_{30}$cycloalkenyl which is interrupted by one or more O, S, NR$_7$, O(CO), (CO)O, (CO)NR$_7$ or NR$_7$(CO),
or are substituted by one or more halogen, NO$_2$, CN, Ar, O(CO)R$_8$, O(CO)OR$_4$, O(CO)NR$_5$R$_6$, NR$_7$(CO)R$_8$, NR$_7$(CO)OR$_4$, OR$_4$, NR$_5$R$_6$, SR$_7$, SOR$_8$, SO$_2$R$_8$ or OSO$_2$R$_8$, optionally the substituents C$_1$-C$_{18}$alkyl, C$_2$-C$_{12}$alkenyl, O(CO)R$_8$, O(CO)OR$_4$, O(CO)NR$_5$R$_6$, NR$_7$(CO)R$_8$, NR$_7$(CO)OR$_4$, OR$_4$, NR$_5$R$_6$, SR$_7$, SOR$_8$, SO$_2$R$_8$ or OSO$_2$R$_8$ form 5-, 6- or 7-membered rings, via the radicals C$_1$-C$_{18}$alkyl, C$_2$-C$_{12}$alkenyl, R$_4$, R$_5$, R$_6$, R$_7$ and/or R$_8$, with further substituents on the phenyl, naphthyl, biphenylyl or heteroaryl or with one of the carbon atoms of the phenyl, naphthyl, biphenylyl or heteroaryl;
or Ar$_1$ and Ar$_2$ together with a direct bond, O, S, NR$_7$ or (CO), form a fused ring system;
or Ar$_1$ and Ar$_2$ together with C$_1$-C$_2$alkylene, O, S, NR$_7$ or (CO), form a 5-, 6-, or 7-membered ring;
or Ar$_2$ and Ar$_3$ together with a direct bond, O, S, NR$_7$ or (CO) form a fused ring system;
or Ar$_2$ and Ar$_3$ together with C$_1$-C$_2$alkylene, O, S, NR$_7$ or (CO), form a 5-, 6-, or 7-membered ring;
or Ar$_1$ and Ar$_2$ together with the

which is attached to the Ar$_1$, form

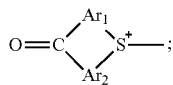

wherein all $Ar_2$ and $Ar_3$ optionally additionally are substituted by a group having a —O—C— bond or a —O—Si-bond which cleaves upon the action of an acid;

R is Ar;

$R_1$, $R_2$ and $R_3$ independently of each other are $C_1$-$C_{10}$haloalkyl or Ar, or independently of each other are $C_2$-$C_{10}$haloalkyl which is interrupted by one or more O, S, $NR_7$, O(CO), (CO)O, (CO)$NR_7$ or $NR_7$(CO), wherein $R_1$, $R_2$ and $R_3$ as $C_1$-$C_{10}$haloalkyl, Ar and interrupted $C_2$-$C_{10}$haloalkyl are unsubstituted or substituted by one or more $NO_2$, CN, Ar, (CO)$R_8$, (CO)$OR_4$, (CO)$NR_5R_6$, O(CO)$R_8$, O(CO)$OR_4$, O(CO)$NR_5R_6$, $NR_7$(CO)$R_8$, $NR_7$(CO)$OR_4$, $OR_4$, $NR_5R_6$, $SR_7$, $SOR_8$, $SO_2R_8$ or $OSO_2R_8$;

or $R_1$ and $R_2$, together with the

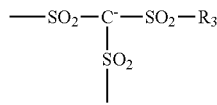

to which they are attached, form a 5-, 6- or 7-membered ring which optionally is interrupted by one or more O, $NR_7$ or CO;

$R_4$ is hydrogen, $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or is $C_2$-$C_{18}$alkyl which is interrupted by one or more O, S, $NR_7$, O(CO), (CO)O, (CO)$NR_7$ or $NR_7$(CO), or is $C_3$-$C_{30}$cycloalkyl which is interrupted by one or more O, S, $NR_7$, O(CO), (CO)O, (CO)$NR_7$ or $NR_7$(CO), or is $C_4$-$C_{30}$cycloalkenyl which is interrupted by one or more O, S, $NR_7$, O(CO), (CO)O, (CO)$NR_7$ or $NR_7$(CO), or $R_4$ is Ar, (CO)$R_8$, (CO)$OR_8$, (CO)$NR_5R_6$ or $SO_2R_8$, wherein $R_4$ as $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_4$-$C_{30}$cycloalkenyl and Ar is unsubstituted or substituted by one or more Ar, OH, $C_1$-$C_{18}$alkyl, $C_1$-$C_{10}$haloalkyl, phenyl-$C_1$-$C_3$-alkyl, $C_3$-$C_{30}$cycloalkyl, halogen, $NO_2$, CN, $C_1$-$C_{18}$alkoxy, phenoxy, phenoxycarbonyl, phenylthio, phenylthiocarbonyl, $NR_5R_6$, $C_1$-$C_{12}$alkylthio, $C_2$-$C_{18}$alkoxycarbonyl, $C_2$-$C_{10}$haloalkanoyl, halobenzoyl, $C_1$-$C_{18}$alkylsulfonyl, phenylsulfonyl, (4-methylphenyl)sulfonyl, $C_1$-$C_{18}$alkylsulfonyloxy, phenylsulfonyloxy, (4-methylphenyl)sulfonyloxy, $C_2$-$C_{18}$alkanoyl, $C_2$-$C_{18}$alkanoyloxy, benzoyl or by benzoyloxy;

$R_5$ and $R_6$ independently of each other are hydrogen, $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or independently of each other are $C_2$-$C_{18}$alkyl which is interrupted by one or more O, S, $NR_7$, O(CO), (CO)O, (CO)$NR_7$ or $NR_7$(CO), or independently of each other are $C_3$-$C_{30}$cycloalkyl which is interrupted by one or more O, S, $NR_7$, O(CO), (CO)O, (CO)$NR_7$ or $NR_7$(CO), or independently of each other are $C_4$-$C_{30}$cycloalkenyl which is interrupted by one or more O, S, $NR_7$, O(CO), (CO)O, (CO)$NR_7$ or $NR_7$(CO), or $R_5$ and $R_6$ independently of each other are Ar, (CO)$R_8$, (CO)$OR_4$ or —$SO_2R_8$, wherein $R_5$ and $R_6$ as $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_4$-$C_{30}$cycloalkenyl and Ar are unsubstituted or substituted by one or more Ar, OH, $C_1$-$C_{18}$alkyl, $C_1$-$C_{10}$haloalkyl, phenyl-$C_1$-$C_3$-alkyl, $C_3$-$C_{30}$cycloalkyl, halogen, $NO_2$, CN, $C_1$-$C_{18}$alkoxy, phenoxy, phenoxycarbonyl, phenylthio, phenylthiocarbonyl, $C_1$-$C_{18}$dialkylamino, $C_1$-$C_{12}$alkylthio, $C_2$-$C_{18}$alkoxycarbonyl, $C_2$-$C_{10}$haloalkanoyl, halobenzoyl, $C_1$-$C_{18}$alkylsulfonyl, phenylsulfonyl, (4-methylphenyl)sulfonyl, $C_1$-$C_{18}$alkylsulfonyloxy, phenylsulfonyloxy, (4-methylphenyl)sulfonyloxy, $C_2$-$C_{18}$alkanoyl, $C_2$-$C_{18}$alkanoyloxy, benzoyl or by benzoyloxy;

or $R_5$ and $R_6$, together with the nitrogen atom to which they are attached, form a 5-, 6- or 7-membered ring which optionally is interrupted by one or more O, $NR_7$ or CO;

$R_7$ is hydrogen, $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or is $C_2$-$C_{18}$alkyl which is interrupted by one or more O, S, O(CO) or (CO)O, or is $C_3$-$C_{30}$cycloalkyl which is interrupted by one or more O, S, O(CO) or (CO)O, or is $C_4$-$C_{30}$cycloalkenyl which is interrupted by one or more O, S, O(CO) or (CO)O; or $R_7$ is Ar, (CO)$R_8$, (CO)$OR_4$, (CO)$NR_5R_6$ or $SO_2R_8$, wherein $R_7$ as $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_4$-$C_{30}$cycloalkenyl and Ar is unsubstituted or substituted by one or more Ar, OH, $C_1$-$C_{18}$alkyl, $C_1$-$C_{10}$haloalkyl, phenyl-$C_1$-$C_3$-alkyl, $C_3$-$C_{30}$cycloalkyl, halogen, $NO_2$, CN, $C_1$-$C_{18}$alkoxy, phenoxy, phenoxycarbonyl, phenylthio, phenylthiocarbonyl, $NR_5R_6$, $C_1$-$C_{12}$alkylthio, $C_2$-$C_{18}$alkoxycarbonyl, $C_2$-$C_{10}$halolkanoyl, halobenzoyl, $C_1$-$C_{18}$alkylsulfonyl, phenylsulfonyl, (4-methylphenyl)sulfonyl, $C_1$-$C_{18}$alkylsulfonyloxy, phenylsulfonyloxy, (4-methylphenyl)sulfonyloxy, $C_2$-$C_{18}$alkanoyl, $C_2$-$C_{18}$alkanoyloxy, benzoyl or by benzoyloxy;

$R_8$ is hydrogen, $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, Ar, $NR_5R_6$, or is $C_2$-$C_{18}$alkyl which is interrupted by one or more O, S, NR, O(CO), (CO)O, (CO)$NR_7$ or $NR_7$(CO), or is $C_3$-$C_{30}$cycloalkyl which is interrupted by one or more O, S, $NR_7$, CO, O(CO), (CO)O, (CO)$NR_7$ or $NR_7$(CO), or is $C_4$-$C_{30}$cycloalkenyl which is interrupted by one or more O, S, $NR_7$, O(CO), (CO)O, (CO)$NR_7$ or $NR_7$(CO), wherein $R_8$ as $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, Ar interrupted $C_2$-$C_{18}$alkyl, interrupted $C_3$-$C_{30}$cycloalkyl and interrupted $C_4$-$C_{30}$cycloalkenyl is unsubstituted or substituted by one or more Ar, OH, $C_1$-$C_{18}$alkyl, $C_1$-$C_{10}$haloalkyl, phenyl-$C_1$-$C_3$-alkyl, $C_3$-$C_{30}$cycloalkyl, halogen, $NO_2$, CN, $C_1$-$C_{18}$alkoxy, phenoxy, phenoxycarbonyl, phenylthio, phenylthiocarbonyl, $NR_5R_6$, $C_1$-$C_{12}$alkylthio, $C_2$-$C_{18}$alkoxycarbonyl, $C_2$-$C_{10}$haloalkanoyl, halobenzoyl, $C_1$-$C_{18}$alkylsulfonyl, phenylsulfonyl, (4-methylphenyl)sulfonyl, $C_1$-$C_{18}$alkylsulfonyloxy, phenylsulfonyloxy, (4-methylphenyl)sulfonyloxy, $C_2$-$C_{18}$alkanoyl, $C_2$-$C_{18}$alkanoyloxy, benzoyl or by benzoyloxy; and Ar is phenyl, biphenylyl, fluorenyl, naphthyl, anthracyl, phenanthryl, or heteroaryl, wherein the phenyl, biphenylyl, fluorenyl, naphthyl, anthracyl, phenanthryl, or heteroaryl are unsubstituted or substituted by one or more $C_3$-$C_{30}$cycloalkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, or are substituted by $C_2$-$C_{18}$alkyl which is interrupted by one or more O, S, $NR_7$, O(CO), (CO)O, (CO)$NR_7$ or $NR_7$(CO), or are substituted by $C_3$-$C_{30}$cycloalkyl which is interrupted by one or more O, S, $NR_7$, O(CO), (CO)O, (CO)$NR_7$ or $NR_7$(CO), or are substituted by $C_4$-$C_{30}$cycloalkenyl which is interrupted by one or more O, S, $NR_7$, O(CO), (CO)O, (CO)$NR_7$ or $NR_7$(CO), or are substituted by one or more halogen, $NO_2$, CN, phenyl, biphenylyl, naphthyl, heteroaryl, (CO)$R_8$, (CO)$OR_4$, (CO)$NR_5R_6$, O(CO)$R_8$, O(CO)$OR_4$, O(CO)$NR_5R_6$, $NR_7$(CO)$R_8$, $NR_7$(CO)$OR_4$, $OR_4$, $NR_5R_6$, $SR_7$, $SOR_8$, $SO_2R_8$ or $OSO_2R_8$, optionally the substituents $C_1$-$C_{18}$alkyl, $C_2$-$C_{12}$alkenyl, (CO)$R_8$, (CO)$OR_4$, (CO)$NR_5R_6$, O(CO)$R_8$, O(CO)$OR_4$, O(CO)$NR_5R_6$, $NR_7$(CO)$R_8$, $NR_7$(CO)$OR_4$, $OR_4$, $NR_5R_6$, $SR_7$, $SOR_8$, $SO_2R_8$ or $OSO_2R_8$, form 5-, 6- or 7-membered rings, via the radicals $C_1$-$C_{18}$alkyl, $C_2$-$C_{12}$alkenyl, $R_4$, $R_5$, $R_6$, $R_7$ or $R_8$, with further substituents on the phenyl, biphenylyl, fluorenyl, naphthyl, anthracyl, phenanthryl or heteroaryl or with one of the carbon atoms of phenyl, biphenylyl, fluorenyl, naphthyl, anthracyl, phenanthryl, or heteroaryl.

2. A compound of the formula I according to claim 1, wherein $Ar_1$ is phenylene, naphthylene or heteroarylene, all of which are unsubstituted or are substituted by one or more $C_1$-$C_{18}$alkyl, $C_1$-$C_{10}$haloalkyl, halogen, $NO_2$, CN, Ar, $OR_4$, $NR_5R_6$ or $SR_7$;

wherein optionally the substituents $C_1$-$C_{18}$alkyl, $OR_4$, $NR_5R_6$ or $SR_7$ form 5-, 6- or 7-membered rings, via the radicals $C_1$-$C_{18}$alkyl, $R_4$, $R_5$, $R_6$ or $R_7$ with further substituents on the phenylene, naphthylene or heteroarylene, or with one of the carbon atoms of the phenylene, naphthylene or heteroarylene;

$Ar_2$ and $Ar_3$ independently of each other are phenyl, naphthyl, biphenylyl or heteroaryl, wherein the phenyl, naphthyl, biphenylyl or heteroaryl are optionally substituted by one or more $C_1$-$C_{18}$alkyl, $C_1$-$C_{10}$haloalkyl, halogen, $NO_2$, CN, Ar, $OR_4$, $NR_5R_6$ or $SR_7$;

wherein optionally the substituents $C_1$-$C_{18}$alkyl, $OR_4$, $NR_5R_6$ or $SR_7$ form 5-, 6- or 7-membered rings, via the radicals $C_1$-$C_{18}$alkyl, $R_4$, $R_5$, $R_6$ or $R_7$ with further substituents on the phenyl, biphenylyl, naphthyl or heteroaryl, or with one of the carbon atoms of the phenyl, biphenylyl, naphthyl or heteroaryl;

or $Ar_1$ and $Ar_2$ together with a direct bond, O, S, $NR_7$ or (CO), form a fused ring system;

or $Ar_1$ and $Ar_2$ together with $C_1$-$C_2$alkylene, O, S, $NR_7$ or (CO), form a 5-, 6-, or 7-membered ring;

or $Ar_2$ and $Ar_3$ together with a direct bond, O, S, $NR_7$ or (CO) form a fused ring system;

or $Ar_2$ and $Ar_3$ together with $C_1$-$C_2$alkylene, O, S, $NR_7$ or (CO), form a 5-, 6-, or 7-membered ring;

or $Ar_1$ and $Ar_2$, together with the

which is attached to $Ar_1$, form

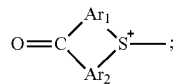

R is Ar;
$R_1$, $R_2$ and $R_3$ independently of each other are $C_1$-$C_{10}$haloalkyl;
$R_4$ is hydrogen, $C_1$-$C_{18}$alkyl, Ar, (CO)$R_8$ or $SO_2R_8$;
$R_5$ and $R_6$ independently of each other are hydrogen, $C_1$-$C_{18}$alkyl, Ar, (CO)$R_8$ or $SO_2R_8$;
$R_7$ is hydrogen, $C_1$-$C_{18}$alkyl, Ar, (CO)$R_8$ or $SO_2R_8$;
$R_8$ is hydrogen, $C_1$-$C_{18}$alkyl or Ar; and
Ar is phenyl, biphenylyl or naphthyl, which phenyl, biphenylyl or naphthyl are unsubstituted or are substituted by one or more $C_1$-$C_{18}$alkyl, halogen, $NO_2$, CN, $OR_4$, $NR_5R_6$ or $SR_7$; optionally the substituents $C_1$-$C_{18}$alkyl, $OR_4$, $NR_5R_6$ or $SR_7$, form 5-, 6- or 7-membered rings, via the radicals $C_1$-$C_{18}$alkyl, $R_4$, $R_5$, $R_6$ or $R_7$, with further substituents on the phenyl, biphenylyl or naphthyl or with one of the carbon atoms of the phenyl, biphenylyl or naphthyl.

3. A compound of the formula I according to claim 1, wherein
$Ar_1$ is phenylene or heteroarylene,
which are unsubstituted or substituted by $OR_4$;
$Ar_2$ and $Ar_3$ independently of each other are phenyl or biphenylyl,
wherein the phenyl or biphenylyl are unsubstituted or are substituted by $C_1$-$C_{18}$alkyl;
or $Ar_1$ and $Ar_2$ together with a direct bond, form a fused ring system;
or $Ar_1$ and $Ar_2$ together with the

which is attached to $Ar_1$, form

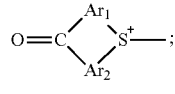

R is Ar;
$R_1$, $R_2$ and $R_3$ are $C_1$-$C_{10}$haloalkyl;
$R_4$ is $C_1$-$C_{18}$alkyl; and
Ar is phenyl which phenyl is unsubstituted or is substituted by $OR_4$.

4. A chemically amplified photoresist composition comprising
(a) a compound which cures upon the action of an acid or a compound whose solubility is increased upon the action of an acid; and
(b) as photosensitive acid donor, at least one compound of the formula I according to claim 1.

5. A chemically amplified photoresist composition according to claim 4, which is a positive resist.

6. A chemically amplified positive photoresist composition according to claim 5, comprising as component (a) at least one component selected from the group consisting of (a1), (a2) and (a3), wherein
- (a1) is a polymer having an acid-labile group which decomposes in the presence of an acid to increase the solubility in aqueous alkaline developer solution;
- (a2) is a monomeric or oligomeric dissolution inhibitor having an acid-labile group which decomposes in the presence of an acid to increase the solubility in aqueous alkaline developer solution; and
- (a3) is an alkali-soluble monomeric, oligomeric or polymeric compound; and
- (b) as photosensitive acid donor, at least one compound of formula I according to claim 1.

7. A chemically amplified photoresist composition according to claim 4, which is a negative resist.

8. A chemically amplified negative photoresist composition according to claim 7, comprising as component (a) at least one component selected from the group consisting of (a4), (a5) and (a6), wherein
- (a4) is an alkali-soluble resin as binder;
- (a6) is a solvent-developable resin as binder;
- (a5) is a component which is cationically or acid-catalytically polymerizable or cross-linkable with itself and/or with the other components;

and
- (b) as photosensitive acid donor, at least one compound of the formula I according to claim 1.

9. A chemically amplified photoresist composition according to claim 4, in addition to components (a) and (b), comprising further additives (c), further photosensitive acid donor compounds (b1), other photoinitiators (d), and/or sensitizers (e).

10. A process for the preparation of a photoresist by
(1) applying to a substrate a composition according to claim 4;
(2) post apply baking the composition at temperatures between 60° C. and 160° C.;
(3) image-wise irradiating with light of wavelengths between 10 nm and 1500 nm;
(4) optionally post exposure baking the composition at temperatures between 60° C. and 160° C.; and
(5) developing with a solvent or with an aqueous alkaline developer.

11. A composition comprising
(a) a compound which cures upon the action of an acid or a compound whose solubility is increased upon the action of an acid; and
(b) as photosensitive acid donor, at least one compound of the formula I according to claim 1.

12. A method of using compounds of formula I according to claim 1, the method comprising the step of adding the compounds of formula I as photosensitive acid donors into compositions that are crosslinked under the action of an acid or as dissolution enhancers into compositions wherein the solubility is increased under the action of an acid.

13. Process for crosslinking compounds that can be crosslinked under the action of an acid, which method comprises adding a compound of formula I according to claim 1 to the above-mentioned compounds and irradiating imagewise or over the whole area with light having a wavelength of 10-1500 nm.

14. Process according to claim 13 for the preparation of pigmented and non-pigmented surface coatings, adhesives, laminating adhesives, structural adhesives, pressure-sensitive adhesives, printing inks, printing plates, relief printing plates, planographic printing plates, intaglio printing plates, processless printing plates, screen printing stencils, dental compositions, colour filters, spacers, electroluminescence displays and liquid crystal displays (LCD), waveguides, optical switches, color proofing systems, resists, photoresists for electronics, electroplating resists, etch resists both for liquid and dry films, solder resist, photoresist materials for a UV and visible laser direct imaging system, photoresist materials for forming dielectric layers in a sequential build-up layer of a printed circuit board, image-recording materials, image-recording materials for recording holographic images, optical information storage or holographic data storage, decolorizing materials, decolorizing materials for image recording materials, image recording materials using microcapsules, magnetic recording materials, micromechanical parts, plating masks, etch masks, glass fiber cable coatings, microelectronic circuits.

15. Process according to claim 13 for the preparation of colour filters or chemically amplified resists.

16. A method of preparing pigmented and non-pigmented surface coatings, adhesives, laminating adhesives, structural adhesives, pressure-sensitive adhesives, printing inks, printing plates, relief printing plates, planographic printing plates, intaglio printing plates, processless printing plates, screen printing stencils, dental compositions, colour filters, spacers, electroluminescence displays and liquid crystal displays (LCD), waveguides, optical switches, color proofing systems, resists, photoresists for electronics, electroplating resists, etch resists both for liquid and dry films, solder resist, photoresist materials for a UV and visible laser direct imaging system, photoresist materials for forming dielectric layers in a sequential build-up layer of a printed circuit board, image-recording materials, image-recording materials for recording holographic images, optical information storage or holographic data storage, decolorizing materials, decolorizing materials for image recording materials, image recording materials using microcapsules, magnetic recording materials, micromechanical parts, plating masks, etch masks, glass fibre cable coatings, microelectronic circuits, the method comprising the step of using compounds of formula I according to claim 1 as photosensitive acid donors.

17. A color filter prepared by providing red, green and blue picture elements and a black matrix, all comprising a photosensitive resin and a pigment and/or dye on a transparent substrate and providing a transparent electrode either on the surface of the substrate or on the surface of the color filter layer, wherein said photosensitive resin comprises compounds of formula I according to claim 1 as photosensitive acid donors.

18. A method of preparing colour filters or chemically amplified resists, the method comprising the step of using compounds of formula I according to claim 1 as photosensitive acid donors.

* * * * *